(12) United States Patent
Wakita et al.

(10) Patent No.: US 8,754,061 B2
(45) Date of Patent: *Jun. 17, 2014

(54) NUCLEIC ACID CONSTRUCT CONTAINING A NUCLEIC ACID DERIVED FROM THE GENOME OF HEPATITIS C VIRUS (HCV) OF GENOTYPE 2A, AND A CELL HAVING SUCH NUCLEIC ACID CONSTRUCT INTRODUCED THEREIN

(71) Applicants: Toray Industries, Inc., Tokyo (JP); Tokyo Metropolitan Institute of Medical Science, Tokyo (JP); Ralf Bartenschlager, Schriesheim (DE)

(72) Inventors: Takaji Wakita, Tokyo (JP); Takanobu Kato, Aichi (JP); Tomoko Date, Kanagawa (JP)

(73) Assignees: Toray Industries, Inc., Tokyo (JP); Tokyo Metropolitan Institute of Medical Science, Tokyo (JP); Ralf Bartenschlager, Schriesheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/733,793

(22) Filed: Jan. 3, 2013

(65) Prior Publication Data

US 2013/0183754 A1 Jul. 18, 2013

Related U.S. Application Data

(62) Division of application No. 12/958,318, filed on Dec. 1, 2010, now Pat. No. 8,383,371, which is a division of application No. 10/558,155, filed as application No. PCT/JP03/15038 on Nov. 25, 2003, now Pat. No. 7,935,676.

(30) Foreign Application Priority Data

May 26, 2003 (JP) ................................. 2003-148242
Sep. 19, 2003 (JP) ................................. 2003-329115

(51) Int. Cl.
*A61K 48/00* (2006.01)
*C12N 15/11* (2006.01)

(52) U.S. Cl.
USPC .......... 514/44 R; 435/235.1; 435/325; 435/5; 435/6.1; 536/23.1

(58) Field of Classification Search
None
See application file for complete search history.

(56) References Cited

U.S. PATENT DOCUMENTS 6,630,343 B1  10/2003  Bartenschlager
7,935,676 B2   5/2011  Wakita et al.

FOREIGN PATENT DOCUMENTS

| CA | 2303526 A1 | 10/2000 |
| EP | 1043399 A2 | 10/2003 |
| JP | 2001-017187 A | 1/2001 |
| JP | 2002-171978 A | 6/2002 |
| WO | WO-00/75338 A2 | 12/2000 |

OTHER PUBLICATIONS

Wakita, T. et al., "Idenshigata 2a no C-gata Kan'en Virus RNA Replicon no Juritsu", Dai 25 Kai The Molecular Biology Society of Japan Nenkai Program Koen Yoshishu, Nov. 25, 2002, p. 386.
Ikeda, M. et al., J. Virol., (Mar. 2002), vol. 76, No. 6, pp. 2997 to 3006.
Friebe, P. et al., J. Virol., (2001), vol. 75, No. 24, pp. 12047 to 12057.
Lohmann, V. et al., Science, (1999), vol. 285 pp. 110 to 113.
Kato et al.; "Sequence Analysis of Hepatitis C Virus Isolated from a Fulminant Hepatitis Patient"; Jornal of Medical Virology, vol. 64, No. 3, 2001, pp. 334-339; XP 002986251.
Date Tomoko et al.; "Genotype 2a hepatitis C virus subjenomic replion can replicate in HepG2 and IMY-N9 cells"; The Journal of Biological Chemistry, vol. 279, No. 21, May 21, 2004, pp. 22371-22376; XP-002391334.
Kato Takanobu et al.; "Efficient replication of the genotype 2a hepatitis C virus subenomic replicion"; Gastroenterology 2003, vol. 125, No. 6, pp. 1808-1817; XP-002391335.
Kato T. et al, Hepatology, (Oct. 2003) vol. 38, No. 4 Suppl. 1, pp. 469A.
Japanese Office Action issued Oct. 6, 2009 related to JP 2004-572138.

*Primary Examiner* — Doug Schultz
(74) *Attorney, Agent, or Firm* — Birch, Stewart, Kolasch & Birch, LLP

(57) ABSTRACT

The present invention relates to a replicon RNA comprising a nucleotide sequence at least containing the 5' untranslated region, the nucleotide sequence encoding NS3 protein, NS4A protein, NS4B protein, NS5A protein and NS5B protein, and the 3' untranslated region on the genomic RNA of hepatitis C virus of genotype 2a.

11 Claims, 25 Drawing Sheets
(11 of 25 Drawing Sheet(s) Filed in Color)

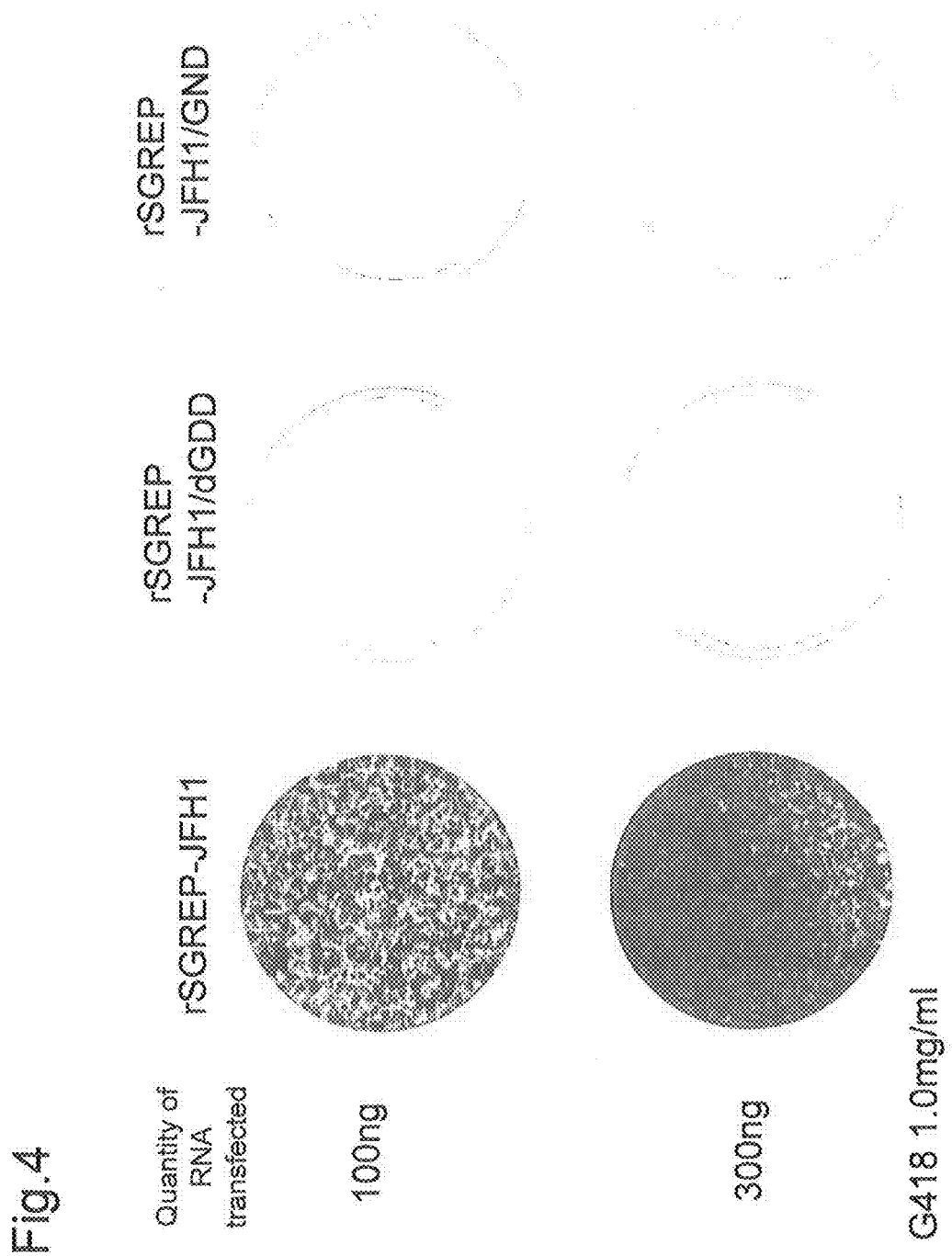

SEQUENCE LISTING

<160> NUMBER OF SEQ ID NOS: 41

<210> SEQ ID NO 1
<211> LENGTH: 8024
<212> TYPE: RNA
<213> ORGANISM: Artificial Sequence
<220> FEATURE:
<223> OTHER INFORMATION: HCV-derived synthetically created RNA replicon rSGREP-JFH1 sequence

<400> SEQUENCE: 1

```
accugcccu aauaggggcg acacuccgcc augaaucacu ccccugugag gaacuacugu      60
cuucacgcag aaagcgccua gccauggcgu uaguaugagu gucguacagc cuccaggccc     120
cccccucccg ggagagccau aguggucugc ggaaccggug aguacaccgg aauugccggg     180
aagacugggu ccuuucuugg auaaacccac ucuaugcccg gccauuuggg cgugcccccg     240
caagacugcu agccgaguag cguuggguug cgaaaggccu ugugguacug ccugauaggg     300
cgcuugcgag ugccccggga ggucucguag accgugcacc augagcacaa auccuaaacc     360
ucaaagaaaa accaaaagaa acaccaaccg ucgcccaaug auugaacaag auggauugca     420
cgcagguucu ccggccgcuu ggguggagag gcuauucggc uaugacuggg cacaacagac     480
aaucggcugc ucugaugccg ccguguuccg gcugucagcg caggggcgcc cgguucuuuu     540
ugucaagacc gaccuguccg gugcccugaa ugaacugcag gacgaggcag cgcggcuauc     600
guggcuggcc acgacgggcg uuccuugcgc agcugugcuc gacguuguca cugaagcggg     660
aagggacugg cugcuauugg gcgaagugcc ggggcaggau cuccugucau cucaccuugc     720
uccugccgag aaaguaucca ucauggcuga ugcaaugcgg cggcugcaua cgcuugaucc     780
ggcuaccugc ccauucgacc accaagcgaa acaucgcauc gagcgagcac guacucggau     840
ggaagccggu cuugucgauc aggaugaucu ggacgaagag caucaggggc ucgcgccagc     900
cgaacuguuc gccaggcuca aggcgcgcau gcccgacggc gaggaucucg ucgugaccca     960
uggcgaugcc ugcuugccga auaucauggu ggaaaauggc cgcuuuucug gauucaucga    1020
cuguggccgg cuggguguggg cggaccgcua ucaggacaua gcguuggcua cccgugauau    1080
ugcugaagag cuuggcggcg aaugggcuga ccgcuuccuc gugcuuuacg guaucgccgc    1140
ucccgauucg cagcgcaucg ccuucuaucg ccuucuugac gaguucuucu gaguuuaaac    1200
ccucucccuc cccccccccu aacguuacug gccgaagccg cuuggaauaa ggccggugug    1260
cguuugucua uauguuauuu uccaccauau ugccgucuuu uggcaaugug agggcccgga    1320
aaccuggccc ugucuucuug acgagcauuc cuaggggucu uuccccucuc gccaaaggaa    1380
ugcaaggucu guugaauguc gugaaggaag caguuccucu ggaagcuucu ugaagacaaa    1440
caacgucugu agcgacccuu ugcaggcagc ggaacccccc accuggcgac aggugccucu    1500
gcggccaaaa gccacgugua uaagauacac cugcaaaggc ggcacaaccc cagugccacg    1560
uugugaguug gauaguugug gaaagaguca aauggcucuc cucaagcgua uucaacaagg    1620
ggcugaagga ugcccagaag guaccccauu guaugggauc ugaucugggg ccucggugca    1680
caugcuuuac auguguuuag ucgagguuaa aaaaacgucu aggccccccg aaccacgggg    1740
acgugguuuu ccuuugaaaa acacgaugau accauggcuc ccaucacugc uuaugcccag    1800
caaacacgag gccuccuggg cgccauagug gugaguauga cggggcguga caggacagaa    1860
caggccgggg aaguccaaau ccuguccaca gucucucagu ccuuccucgg aacaaccauc    1920
ucggggguuu uguggacugu uuaccacgga gcuggcaaca agacucuagc cggcuuacgg    1980
```

```
gguccgguca cgcagaugua cucgagugcu gaggggggacu ugguaggcug gcccagcccc    2040
ccugggacca agucuuugga gccgugcaag uguggagccg ucgaccauau ucggucacg     2100 cggaacgcug augucauccc ggcucggaga cgcggggaca agcggggagc auugcucucc    2160
ccgagaccca uuucgaccuu aaggggucc ucggggggc cggugcucug cccuagggc      2220 cacgucguug ggcucuuccg agcagcugug ugcucucggg gcguggccaa auccaucgau    2280
uucauccccg uugagacacu cgacguuguu acaaggucuc ccacuuucag ugacaacagc    2340
acgccaccgg cugugcccca gaccuaucag gucgggacu ugcaugcucc aacuggcagu    2400
ggaaagagca ccaaggcccc ugucgcguau gccgcccagg gguacaaagu acagugcuu    2460 aaccccucgg uagcugccac ccugggguuu gggcgcuacc uaccaaggc acauggcauc    2520 aaucccaaca uuaggacugg agucaggacc gugaugaccg ggggagccau cacguacucc    2580
acauauggca aauuucucgc cgaugggggc ugcgcuagcg cgccuauga caucaucaua    2640 ugcgaugaau gccacgcgu ggaugcuacc uccauucucg gcaucggaac gguccuugau     2700
caagcagaga cagccggggu cagacuaacu gucuggcua cggccacacc ccccgggucaa    2760 gugacaaccc cccauccga uauagaagag guaggccucg ggcgggaggg ugagaucccc     2820
uucuauggga gggcgauucc ccuauccugc aucaaaggag ggagacaccu gauuuucugc    2880
cacucaaaga aaaagugugua cgagcucgcg gcggcccuuc ggggcauggg cuugaaugcc    2940
guggcauacu auagagggguu ggacgucucc auaauaccag cucaggggaga ugugggguc    3000 gucgccaccg acgcccucau gacgggguac acuggagacu ugaccccguu gaucgacug    3060 aauguagcgg ucacccaagc ugucgacuuc agccuggacc ccaccuucac uauaaccaca    3120
cagacugucc cacaagacgc ugucucacgc agucagcgcc gcgggcgcac agguagagga    3180
agacagggca cuuuaaggua uguuccacu ggugaacgag ccucaggaau guuugacagu    3240
guagugcuuu gugagugcua cgacgcaggg gcugcgguggu acgaucucac accagcggag    3300
accaccguca ggcuuagagc guauuucaac acgcccggcc uacccgugug ucaagaccau    3360
cuugaauuuu gggaggcagu uuucaccggc cucacacaca uagacgccca cuuccucucc    3420
caaacaaagc aagcggggga gaacuucgcg uaccuaguag ccuaccaagc uacggugugc    3480
gccagagcca aggccccucc ccgguccugg gacgccaugu ggaagugcc ggcccgacuc    3540 aagccuacgc uugcgggccc cacaccucuc cguguaccguu ugggccccuau uaccaaugag    3600 gucacccuca cacacccugg gacgaaguac aucgccacau gcaugcaagc ugaccuugag    3660
gucaugacca gcacgugggu ccuagcugga ggaguccugg cagccgucgc cgcauauugc    3720
cuggcgacug gaugucguuuc caucaucggc cgcuugcacg ucaaccagcg agucgucguu    3780
gcgccggaua aggaggucuu guaugaggcu uuugaugaga uggaggaaug cgccucuagg    3840
gcggcucuca ucgaagaggg gcagcgggaua gccgagaugu ugaagccaa gauccaaggc    3900 uugcugcagc aggccucuaa gcaggcccag gacauacaac ccgcuaugca ggcuucaugg    3960
cccaaagugg aacaauuuug ggcagagacac auguggaacu ucauuagcgg cauccaauac    4020
cucgcaggau ugucaacacu gccagggaac cccgcguggg cuuccaugau ggcauucagu    4080
gccgcccuca ccaguccguu gucgaccagu accaccaucc uucucaacau caugggaggc    4140
ugguuagcgu cccagaucgc accacccgcg ggggccaccg gcuuugucgu cagugggccug    4200 gugggggcug ccguggggca cauaggccug gguaaggugc ugguggacau ccuggcagga    4260 uaugugcgg gcauuucggg ggccucguc gcauucaaga ucaugucugg cgagaagccc    4320
ucuauggaag augucaucaa ucuacugccu ggggauccugu cuccgggagc ccugguggug    4380
```

```
ggggucaucu gcgcggccau ucugcgccgc cacgugggac cggggagggg cgcgguccaa      4440
uggaugaaca ggcuuauugc cuuugcuucc agaggaaacc acgucgcccc uacucacuac      4500
gugacggagu cggaugcguc gcagcgugug acccaacuac uuggcucucu uacuauaacc      4560
agccuacuca gaagacucca caauuggaua acugaggacu gccccauccc augcuccgga      4620
uccuggcucc gcgacgugug ggacuggguu ugcaccaucu ugacagacuu caaaaauugg      4680
cugaccucua aauuguuccc caagcugccc ggccuccccu ucaucucuug ucaaagggg       4740 uacaagggug uguggccgg cacuggcauc augaccacgc gcugcccuug cggcgccaac       4800
aucucuggca auguccgccu gggcucuaug aggaucacag gccuaaaaac cugcaugaac      4860
accuggcagg ggaccuuucc uaucaauugc uacacggagg ccagugcgc gccgaaaccc       4920 cccacgaacu acaagaccgc caucuggagg guggcggccu cggaguacgc ggaggugacg      4980 cagcauggu cguacuccua guaacagga cugaccacug acaaucugaa aauuccuugc        5040
caacuaccuu cuccagaguu uuucuccugg uggacgguy ugcagauca uagguuugca        5100 cccacaccaa agccguuuuu ccgggaugag gucucguucu gcguugggcu uaauuccuau      5160
gcugucgggu cccagcuucc cuguaaaccu gagcccgacg cagacguauu gaggucaug       5220 cuaacagauc cgccccacau cacggcggag acugcggcgc ggcgcuuggc acggggauca     5280
ccuccaucug aggcgagcuc ucagugagc cagcuaucag caccgucgcu gcgggccacc       5340
ugcaccaccc acagcaacac cuaugacgug gacauggucg augccaaccu gcucauggag      5400
ggcggugugg cucagacaga gccugagucc agggugcccg uucugacuu ucucgagcca      5460 auggccgagg aagagagcga ccuugagccc ucaauaccau cggagugcau gcuccccagg      5520
agcggguuuc cacgggccuu accggcuugg gcacggccug acuacaaccc gccgcucgug       5580
gaaucgugga ggaggccaga uuaccaaccg cccaccguug cugguuguge cucccccccc      5640 cccaagaagg ccccgacgcc ucccccaagg agacgccgga cagugggucu gagcgagagc      5700
accauaucag aagcccucca gcaacuggcc aucaagaccu uggccagcc cccuucgagc       5760 ggugaugcag gcucguccac ggggcgggc gccgccgaau ccggcggucc gacgucccu        5820 ggugagccgg ccccucaga gacaagguucc gccuccucua ugccccccu cgaggggag        5880 ccuggagauc cggaccugga gucugaucag guagagcuuc aaccuccccc ccagggggg       5940 ggggguagcuc ccgguucggg cucggggucu uggucuacuu gcuccgagga ggacgauacc     6000
accgugugcu gcuccaugua uacuccuugg accgggcuc uaauaacuccc cuguagcccc      6060 gaagaggaaa aguugccaau caacccuuug aguaacucgc uguugcgaua ccauaacaag      6120
guguacugua caacaucaaa gagcgcccuca cagagggcua aaaagguaac uuuugacagg     6180
acgcaagugc ucgacgccca uuaugacuca gucuuaaagg acaucaagcu agcggcuucc      6240
aaggucagcg caaggcuccu caccuuggag gaggcgugcc aguugacucc accccauucu      6300
gcaagaucca aguauggauu cggggccaag gagguccgca gcuugccgg gagggccguu      6360 aaccacauca aguccgugug gaaaggaccuc ugaagacc cacaaacacc aauucccaca      6420 accaucaug ccaaaaauga ggguucgc gugaccccg ccaagggggg uaagaaacca         6480
gcucgccuca ucguuuaccc ugaccucggc gucgggucu gcgagaaaau ggcccuuau        6540 gacauuacac aaaagcuucc ucaggcgcua augggagcuu ccuauggcuu ccaguacucc      6600 ccugccccaac ggguggagua ucucuugaaa gcaugggcgg aaaagaagga cccaugggu     6660 uuucgauug uacccgaug cuucgacuca ccgucacug agagagacau caggaccgag        6720
gaguccauau accaggccug cuccccugccc gaggaggccc gcacugccau acacucgcug     6780
```

-continued acugagagac uuuacguagg agggcccaug uucaacagca agggucaaac cugcgguuac 6840
agacguugcc gcgccagcgg ggugcuaacc acuagcaugg guaacaccau cacaugcuau 6900
gugaaagccc uagcggccug caaggcugcg ggauaguug cgcccacaau gcugguaugc 6960
ggcgaugacc uaguagucau cucagaaagc caggggacug aggaggacga gcggaaccug 7020
agagccuuca cggaggccau gaccagguac ucugccccuc cuggugaucc ccccagaccg 7080
gaauaugacc uggagcuaau aacauccugu uccucaaaug ugucuguggc guugggcccg 7140
cggggccgcc gcagauacua ccugaccaga gacccaacca cuccacucgc ccgggcugcc 7200
ugggaaacag uuagacacuc cccuaucaau ucauggcugg gaaacaucau ccaguaugcu 7260
ccaaccauau ggguucgcau gguccuaaug acacacuucu ucuccauucu caugguccaa 7320
gacacccugg accagaaccu caacuuugag auguauggau caguauacuc cgugaauccu 7380
uuggaccuuc cagccauaau ugagagguua cacgggcuug acgccuuuuc uaugcacaca 7440
uacucucacc acgaacugac gcggguggcu ucagcccuca gaaaacuugg ggcgccaccc 7500
cucagggugu ggaagagucg ggcucgcgca gucagggcgu cccucaucuc ccguggaggg 7560
aaagcggccg uuugcggccg auaucucuuc aauugggcgg ugaagaccaa gcucaaacuc 7620
acuccauugc cggaggcgcg ccuacuggac uuauccaguu gguucaccgu cggcgccggc 7680
gggggcgaca uuuuucacag cgugucgcgc gcccgacccc gcucauuacu cuucggccua 7740
cuccuacuuu ucguaggggu aggccucuuc cuacuccccg cucgguagag cggcacacac 7800
uagguacacu ccauagcuaa cuguuccuuu uuuuuuuuuu uuuuuuuuuu uuuuuuuuuu 7860
uuuuuuuuuu cuuuuuuuuu uuuuucccuc uuucuucccu ucucaucuua uucuacuuuc 7920
uuucuuggug gcuccaucuu agcccuaguc acggcuagcu gugaaagguc cgugagccgc 7980
augacugcag agagugccgu aacuggucuc ucugcagauc augu 8024

<210> SEQ ID NO 2
<211> LENGTH: 8024
<212> TYPE: RNA
<213> ORGANISM: Artificial Sequence
<220> FEATURE:
<223> OTHER INFORMATION: HCV-derived synthetically created RNA Replicon rSGREP-JCH1

<400> SEQUENCE: 2
acccgccccu aauaggggcg acacuccgcc augaaucacu ccccugugag gaacuacugu 60
cuucacgcag aaagcgucua gccauggcgu uaguaugagu gucguacagc cuccaggccc 120
cccccucccg ggagagccau aguggucugc ggaaccggug aguacaccgg aauugccggg 180
aagacugggu ccuuucuugg auaaacccac ucuaugcccg gccauuuggg cgugcccccg 240
caagacugcu agccgaguag cguugggguug cgaaaggccu ugugguacug ccugauaggg 300
ugcuugcgag ugccccggga ggucucguag accgugcacc augagcacaa aucccaaacc 360
ucaaagaaaa accaaaagaa acacuaaccg ucgcccaaug auugaacaag auggauugca 420
cgcagguucu ccggccgcuu ggguggagag gcuauucggc uaugacuggg cacaacagac 480
aaucggcugc ucugaugccg ccguguuccg gcugucagcg caggggcgcc cgguucuuuu 540
ugucaagacc gaccuguccg gugcccugaa ugaacugcag gacgaggcag cgcggcuauc 600
guggcuggcc acgacgggcg uuccuugcgc agcugugcuc gacguuguca cugaagcggg 660
aagggacugg cugcuauugg gcgaagugcc ggggcaggau cuccugucau cucaccuugc 720
uccugccgag aaaguaucca ucauggcuga ugcaaugcgg cggcugcaua cgcuugaucc 780

-continued

| | |
|---|---|
| ggcuaccugc ccauucgacc accaagcgaa acaucgcauc gagcgagcac guacucggau | 840 |
| ggaagccggu cuugucgauc aggaugaucu ggacgaagag caucggggc ucgcgccagc | 900 |
| cgaacuguuc gccaggcuca aggcgcgcau gcccgacggc gaggaucucg ucgugaccca | 960 |
| uggcgaugcc ugcuugccga auaucauggu ggaaaauggc cgcuuuucug gauucaucga | 1020 |
| cuguggccgg cugggugugg cggaccgcua ucaggacaua gcguuggcua cccgugauau | 1080 |
| ugcugaagag cuuggcggcg aaugggcuga ccgcuuccuc gugcuuuacg guaucgccgc | 1140 |
| ucccgauucg cagcgcaucg ccuucuaucg ccuucuugac gaguucuucu gaguuuaaac | 1200 |
| ccucccccuc cccccccccu aacguuacug gccgaagccg cuuggaauaa ggccggugug | 1260 |
| cguuugucua uauguuauuu uccaccauau ugccgucuuu ggcaaugug agggcccgga | 1320 |
| aaccuggccc ugucuucuug acgagcauuc cuagggguc uuccccucuc gccaaaggaa | 1380 |
| ugcaaggucu guugaauguc gugaaggaag caguuccucu ggaagcuucu ugaagacaaa | 1440 |
| caacgucugu agcgacccuu gcaggcagc ggaaccccc accuggcgac aggugccucu | 1500 |
| gcggccaaaa gccacgugua aagauacac cugcaaaggc ggcacaaccc cagugccacg | 1560 |
| uugugaguug gauaguugug gaaagaguca aauggcucuc cucaagcgua uucaacaagg | 1620 |
| ggcugaagga ugcccagaag guaccccauu guaugggauc ugaucggggg ccucggugca | 1680 |
| caugcuuuac augguguuag ucgagguuaa aaaaacgucu aggccccccg aaccacgggg | 1740 |
| acguggauuu ccuugaaaa acacgauaau accauggccc ccaucaccgc uuacgcccag | 1800 |
| cagacacgag gucucuuggg cucuauagug gugagcauga cggggcguga caagacagaa | 1860 |
| caggccgggg agguccaagu ccuguccaca gucacucagu ccuuccucgg aacauccauu | 1920 |
| ucggggucu uauggacugu uuaccacgga gcuggcaaca agacacuagc cggcucgcgg | 1980 |
| ggcccgguca cgcagaugua cucgagcgcc gagggggacu uggucgggug gcccagcccu | 2040 |
| ccugggacca aaucuuugga gccgugauacg uguggagcgg ucgaccugua uuugucacg | 2100 |
| cggaacgcug augucauccc ggcucgaaga cgcggggaca agcggggagc gcugcucucc | 2160 |
| ccgagacccc uuucgaccuu gaaggggucc ucgggggggac cugugcuuug cccuagggc | 2220 |
| cacgcugucg gaaucuuccg ggcagcgug ugcucucggg guguggcuaa guccauagau | 2280 |
| uucauccccg uugagacgcu cgacaucguc acgcggcucuc ccaccuuuag ugacaacagc | 2340 |
| acaccaccag cuguqcccca gaccuaucag gugggguacu ugcacgcccc cacuggcagu | 2400 |
| ggaaaaagca ccaaggucc cgucgcguac gccgcccagg gguauaaagu gcuggugcuc | 2460 |
| aaucccucgg uggcugccac ccugggauuu ggggcguacu ugccaaggc acauggcauc | 2520 |
| aaccccaaca uuaggacugg agcagaacu gugacgaccg gggagcccau acauacucc | 2580 |
| acguauggua aauuccucgc cgaugggggc ugcgcaggcg gcgccauga caucaucaua | 2640 |
| ugcgaugaau gccacucugu ggaugcuacc acuauucucg gcaucgggac aguccuugac | 2700 |
| caagcagaga cagccggggu caggcuaacu guacuggcca cggccacgcc ccccgggucg | 2760 |
| gugacaaccc cccaucccaa uauagaggag guagcccucg acaggaggg ugagauccc | 2820 |
| uucuaugga gggcguuucc ccugucuuac aucaagggag ggaggcacuu gauuuucugc | 2880 |
| cacucaaaga aaagugugac gagcucgca acggcccuuc gggggcaugg cuugaacgcu | 2940 |
| guggcauauu acagagggu ggacgucccc auaauaccaa ucaaggaga uguggugc | 3000 |
| guugccaccg acgcccucau gacggggau acuggagacu uugacccgu gaucgacgc | 3060 |
| aacguagcgg ucacccaggc cguagacuuc agccuggacc ccaccuucac uauaaccaca | 3120 |
| cagacuguc cgcaagacgc ugucucacgu agucagcgcc gagggcgcac ggguagagga | 3180 |

| | |
|---|---|
| agacugggca uuuauaggua uguuccacu ggugagcgag ccucaggaau guuugacagu | 3240 |
| guaguacucu gugagugcua cgacgcagga gcugcuuggu augagcucuc accaguggag | 3300 |
| acgaccguca ggcucagggc guauuucaac acgccuggcu ugccugugug ccaggaccac | 3360 |
| cuugaguuuu gggaggcagu uuucaccggc cucacacaca uagacgcuca uuccuuucc | 3420 |
| cagacaaagc agucggggga aaauuucgca acuuaguag ccaucaggc cacagugugc | 3480 |
| gccagggcca aagcgccccc cccguccugg gacgucaugu ggaagugcuu gacucgacuc | 3540 |
| aagcccacgc uuguggggcc uacaccucuc cuguaccguu ugggcucugu uaccaacgag | 3600 |
| gucacccuua cacaccccgu gacaaaauac aucgccacau gcaugcaagc ugaccucgag | 3660 |
| gucaugacca gcacgugggu ccuggcuggg ggagucuuag cagccgucgc cgcguauugc | 3720 |
| uuagcgaccg ggguguguuuc caucauuggc cguuuacaca ucaaccagcg agcugucguc | 3780 |
| gcuccggaca aggagguccu cuaugaggcu uuugaugaga uggaggaaug ugccuccaga | 3840 |
| gcggcucucc uugaagaggg gcagcggaua gccgagaugc ugaaguccaa gauccaaggc | 3900 |
| uuauugcagc aagccucuaa acaggcccag gacauacaac ccgcugugca agcuucgugg | 3960 |
| cccaagaugg agcaauucug ggccaaacau augggaaacu caugaagcgg cauucaguac | 4020 |
| cucgcaggac ugucaacacu gccagggaac ccugcugugg cuuccaugau ggcauucagc | 4080 |
| gccgcccuca ccagccguu gucaacuagc accaccaucc uucuuaacau ucugggggc | 4140 |
| uggcuggcgu cccaaauugc gccacccgcg ggggccacug gcuuuguugu cagugggccug | 4200 |
| gugggagcug cuguuggcag cauaggcuug gguaaagugc ugguggacau ccuggcaggg | 4260 |
| uauggugcgg gcauuucggg ggcccucguc gcguuuaaga ucaugucugg cgagaagccc | 4320 |
| uccauggagg augucaucaa cuugcugccu gggauucugu uccaggugc ucugguggug | 4380 |
| ggagucaucu gcgcggccau ucugcgccgc caugugggac cggggggaagg cgcgguccaa | 4440 |
| uggaugaaca ggcuuaucgc cuucgcuucc agaggaaacc acgucgcccc uacucacuac | 4500 |
| gugacggagu cggaugcguc gcagcugucc acccaacugc uuggcucucu cacuauaacu | 4560 |
| agucuacuca ggagacuuca caacuggauc acugaggauu gccccauccc augcgccggc | 4620 |
| ucguggcucc gcgaugugug ggacggguc uguaccaucc uaacagacuu uaagaacugg | 4680 |
| cugaccucca agcuguuccc aaagaugccu ggccucccu uuaucucuug ccaaaagggg | 4740 |
| uacaagggcg uguggccgg cacuggcauc augaccacac gaugcccug cggcgccaac | 4800 |
| aucucuggca acguccgcuu gggcucuaug agaaucacag acccaaaaac cugcaugaac | 4860 |
| accuggcagg ggaccuuucc uaucaauugu auacagaag gccagugcuu gccgaaaccc | 4920 |
| gcguuaaacu ucaagaccgc caucuggaga gugguggccu cagauacgc ggaagugacg | 4980 |
| cagcacggau cauaugccua uauaacaggg cugaccacug acaacuuaaa aguccccuugc | 5040 |
| caacucccu cuccagaguu uuucucuugg guggacggag uacaaauucca uaggucccgcc | 5100 |
| cccacaccaa agccguuuuu ccgggaugag gucucguuca gcguugggcu caauucauuu | 5160 |
| gucgucgggu cucagcuucc cugugacccu gagcccgaca cugaggauagu gaugucccaug | 5220 |
| cuaacagacc caucccauau cacgcgcgag gcugcagcgc ggcguuuagc gcggggguca | 5280 |
| cccccaucug aggcaagcuc cucagcgagc cagcugucgg cgccaucgcu gcgagccacc | 5340 |
| ugcaccaccc acgguaggac cuaugaugug gacaugguggg augccaaccu guucaugggg | 5400 |
| ggcggcguga uucggauaga gucugaguccc aaaguggucg uucggacuc ccucgacuca | 5460 |
| augaccgagg aagagggcga ccuugagccu ucaguaccau cggaguauau gcuccccagg | 5520 |
| aagagguucc caccggccuu accggcuugg gcgcggccug auuacaaccc accgcuugug | 5580 |

```
gaaucgugga agaggccaga uuaccaacca cccacuguug cgggcugugc ucuccccccc    5640
cccaaaaaga ccccgacgcc uccuccaagg agacgccgga cagugggucu gagcgagagc    5700
accauaggag augcccucca acagcuggcc aucaagaccu uuggccagcc cccccccaagc    5760 ggcgauucag gccuuuccac gggggcggac gccgccgacu ccggcgaucg gacaccccccu    5820 gacgaguugg cucuuucgga gacagguucu accuccucca ugcccccccu cgaggggggag    5880 ccuggggacc cagaccugga gccugagcag guagagcuuc aaccuccucc cagggggggg    5940
gaggcagcuc ccggcucgga cucgggaucc uggucuacuu gcuccgagga ggaugacucc    6000
gucgugugcu gcuccauguc auauuccugg accggggcuc uaauaacucc uuguagcccc    6060
gaagaggaaa aguugccaau uaacuccuug agcaacucgc guuugcgauaa ccauaacaag    6120 guauacugua cuacaucaaa gagugccuca cuaagggcua aaaagguaac uuuugauagg    6180
augcaagugc ucgacgccua uuaugauuca gucuuaaagg acaucaagcu agcggccucc    6240
aaggucagcg caaggcuccu caccuuagag gaggcgugcc aauugacccc acccccacucu    6300 gcaagaucca aguauggguu uggggcuaag gagguccgca gcuuguccgg gagggccguc    6360
aaccacauca aguccgugug gaaggaccuc uuggaagacu cacaaacacc aauuccuaca    6420
accaucaugg ccaaaaauga ggguuucugc guggaccccg ccaagggggg uaaaaaacca    6480
gcucgccuua ucguuuaccc ugaccucggc gucagggucu gcgagaagau ggcccuuuau    6540
gaugucacac aaaagcuucc ucaggcggug auggggggcuu cuuauggcuu ccaguacucc    6600
cccgcucagc ggguggaguu ucucuugaag gcauggggcgg aaaagagaga cccuauggguu    6660 uuuucguaug auacccgaug cuuugacuca accgucacug agagagacau caggacugag    6720
gaguccauau accaggccug cucccuuaccc gaggaggccc gaacugccau acacucgcug    6780
acugagagac ucuaugugggg agggcccaug uucaacagca agggccaguc cugcgggguac    6840 aggcguugcc gcgccagcgg ggugcuuacc acuaguaugg ggaacaccau cacaugcuau    6900
guaaaagccc uagcggcuug caaggcugcg gggauaauug cgcccacgau gcugguaugc    6960
ggcgacgacu uggucgucau ucagaaaagc caggggacug aggaggacga gcggaaccug    7020
agagccuuca cggaggcuau gaccagguau ucugccccuc cuggugaccc ccccagaccg    7080
gaauaugacc uggagcuaau aacaucuugu uccucaaacg ugucuguggc acuuggccca    7140
cagggccgcc gcagauacua ccugaccaga gaccccacca cuucaauugc ccgggcugcc    7200
ugggaaacag uuagacacuc cccugucaau cauggcuggg aaacaucau ccaguacgcu    7260 ccaaccauau ggguucgcau ggccugaug acacacuucu ucuccauucu cauggccag    7320 gacacccuag accagaaccu uaacuuugaa auguacggau cgguguacuc cgugagccu    7380 cuggaccucc cagccauaau ugaaagguua cacgggcuug acgccuucuc ucugcacaca    7440
uacacucccc acgaacugac gcggguggcu ucagcccuca gaaaacuugg ggcgccaccc    7500
cucagagcgu ggaagagucg ggcgcgugca guuagggcgu ccccucaucuc ccgugggggg    7560 agggcggccg uuugcggucg guaccucuuc aacugggcgg ugaagaccaa gcucaaacuc    7620
acuccuuugc cggaggcacg ccuccuggau uugccaguu gguuuaccgu cggcgccggc    7680
gggggcgaca uuuaucacag cgugucgcgu gcccgacccc gccauuacu ccuuagccua    7740 cuccuacuuu cuguagggu aggcucuuc cuacucccg cucgauagag cggcacacau    7800
uagcuacacu ccauagcuaa cuguuccuuu uuuuuuuuuu uuuuuuuuuu uuuuuuuuuu    7860
uuuuuuuuuu cuuuuuuuuu uuuucccuc uuucuucccu ucucaucuua uucuacuuuc    7920
uuucuuggug gcuccaucuu agcccuaguc acggcuagcu gugaaaagguc cgugagccgc    7980
```

```
augacugcag agagugccgu aacuggucuc ucugcagauc augu                    8024
```

<210> SEQ ID NO 3
<211> LENGTH: 9678
<212> TYPE: DNA
<213> ORGANISM: Hepatitis C virus
<220> FEATURE:
<221> NAME/KEY: CDS
<222> LOCATION: (341)..(9442)

<400> SEQUENCE: 3

```
acctgcccct aatagggcg acactccgcc atgaatcact ccctgtgag gaactactgt    60 cttcacgcag aaagcgccta gccatggcgt tagtatgagt gtcgtacagc ctccaggccc   120
ccccctcccg ggagagccat agtggtctgc ggaaccggtg agtacaccgg aattgccggg   180
aagactgggt cctttcttgg ataaacccac tctatgcccg ccatttggg cgtgcccccg    240 caagactgct agccgagtag cgttgggttg cgaaaggcct tgtggtactg cctgataggg   300
cgcttgcgag tgccccggga ggtctcgtag accgtgcacc atg agc aca aat cct    355
                                              Met Ser Thr Asn Pro
                                                1               5 aaa cct caa aga aaa acc aaa aga aac acc aac cgt cgc cca gaa gac    403
Lys Pro Gln Arg Lys Thr Lys Arg Asn Thr Asn Arg Arg Pro Glu Asp
             10                  15                  20 gtt aag ttc ccg ggc ggc ggc cag atc gtt ggc gga gta tac ttg ttg    451
Val Lys Phe Pro Gly Gly Gly Gln Ile Val Gly Gly Val Tyr Leu Leu
         25                  30                  35 ccg cgc agg ggc ccc agg ttg ggt gtg cgc acg aca agg aaa act tcg    499
Pro Arg Arg Gly Pro Arg Leu Gly Val Arg Thr Thr Arg Lys Thr Ser
     40                  45                  50 gag cgg tcc cag cca cgt ggg aga cgc cag ccc atc ccc aaa gat cgg    547
Glu Arg Ser Gln Pro Arg Gly Arg Arg Gln Pro Ile Pro Lys Asp Arg
 55                  60                  65 cgc tcc act ggc aag gcc tgg gga aaa cca ggt cgc ccc tgg ccc cta    595
Arg Ser Thr Gly Lys Ala Trp Gly Lys Pro Gly Arg Pro Trp Pro Leu
     70                  75                  80                  85 tat ggg aat gag gga ctc ggc tgg gca gga tgg ctc ctg tcc ccc cga    643
Tyr Gly Asn Glu Gly Leu Gly Trp Ala Gly Trp Leu Leu Ser Pro Arg
             90                  95                 100 ggc tct cgc ccc tcc tgg ggc ccc act gac ccc cgg cat agg tcg cgc    691
Gly Ser Arg Pro Ser Trp Gly Pro Thr Asp Pro Arg His Arg Ser Arg
        105                 110                 115 aac gtg ggt aaa gtc atc gac acc cta acg tgt ggc ttt gcc gac ctc    739
Asn Val Gly Lys Val Ile Asp Thr Leu Thr Cys Gly Phe Ala Asp Leu
    120                 125                 130 atg ggg tac atc ccc gtc gta ggc gcc ccg ctt agt ggc gcc gcc aga    787
Met Gly Tyr Ile Pro Val Val Gly Ala Pro Leu Ser Gly Ala Ala Arg
135                 140                 145 gct gtc gcg cac ggc gtg aga gtc ctg gag gac ggg gtt aat tat gca    835
Ala Val Ala His Gly Val Arg Val Leu Glu Asp Gly Val Asn Tyr Ala
150                 155                 160                 165 aca ggg aac cta ccc ggt ttc ccc ttt tct atc ttc ttg ctg gcc ctg    883
Thr Gly Asn Leu Pro Gly Phe Pro Phe Ser Ile Phe Leu Leu Ala Leu
                170                 175                 180 ttg tcc tgc atc acc gtt ccg gtc tct gct gcc cag gtg aag aat acc    931
Leu Ser Cys Ile Thr Val Pro Val Ser Ala Ala Gln Val Lys Asn Thr
            185                 190                 195 agt agc agc tac atg gtg acc aat gac tgc tcc aat gac agc atc act    979
Ser Ser Ser Tyr Met Val Thr Asn Asp Cys Ser Asn Asp Ser Ile Thr
        200                 205                 210 tgg cag ctc gag gct gcg gtt ctc cac gtc ccc ggg tgc gtc ccg tgc   1027
```

|   |   |   |   |   |   |   |   |   |   |   |   |   |   |   |
|---|---|---|---|---|---|---|---|---|---|---|---|---|---|---|
| Trp | Gln | Leu | Glu | Ala | Ala | Val | Leu | His | Val | Pro | Gly | Cys | Val | Pro | Cys |
|  | 215 |  |  |  | 220 |  |  |  | 225 |  |  |  |  |  |

```
gag aga gtg ggg aat acg tca cgg tgt tgg gtg cca gtc tcg cca aac        1075
Glu Arg Val Gly Asn Thr Ser Arg Cys Trp Val Pro Val Ser Pro Asn
230             235                 240                 245 atg gct gtg cgg cag ccc ggt gcc ctc acg cag ggt ctg cgg acg cac        1123
Met Ala Val Arg Gln Pro Gly Ala Leu Thr Gln Gly Leu Arg Thr His
            250                 255                 260 atc gat atg gtt gtg atg tcc gcc acc ttc tgc tct gct ctc tac gtg        1171
Ile Asp Met Val Val Met Ser Ala Thr Phe Cys Ser Ala Leu Tyr Val
                265                 270                 275 ggg gac ctc tgt ggc ggg gtg atg ctc gcg gcc cag gtg ttc atc gtc        1219
Gly Asp Leu Cys Gly Gly Val Met Leu Ala Ala Gln Val Phe Ile Val
        280                 285                 290 tcg ccg cag tac cac tgg ttt gtg caa gaa tgc aat tgc tcc atc tac        1267
Ser Pro Gln Tyr His Trp Phe Val Gln Glu Cys Asn Cys Ser Ile Tyr
    295                 300                 305 cct ggc acc atc act gga cac cgc atg gca tgg gac atg atg atg aac        1315
Pro Gly Thr Ile Thr Gly His Arg Met Ala Trp Asp Met Met Met Asn
310                 315                 320                 325 tgg tcg ccc acg gcc acc atg atc ctg gcg tac gtg atg cgc gtc ccc        1363
Trp Ser Pro Thr Ala Thr Met Ile Leu Ala Tyr Val Met Arg Val Pro
            330                 335                 340 gag gtc atc ata gac atc gtt agc ggg gct cac tgg ggc gtc atg ttc        1411
Glu Val Ile Ile Asp Ile Val Ser Gly Ala His Trp Gly Val Met Phe
                345                 350                 355 ggc ttg gcc tac ttc tct atg cag gga gcg tgg gcg aag gtc att gtc        1459
Gly Leu Ala Tyr Phe Ser Met Gln Gly Ala Trp Ala Lys Val Ile Val
        360                 365                 370 atc ctt ctg ctg gcc gct ggg gtg gac gcg ggc acc acc acc gtt gga        1507
Ile Leu Leu Leu Ala Ala Gly Val Asp Ala Gly Thr Thr Thr Val Gly
    375                 380                 385 ggc gct gtt gca cgt tcc acc aac gtg att gcc ggc gtg ttc agc cat        1555
Gly Ala Val Ala Arg Ser Thr Asn Val Ile Ala Gly Val Phe Ser His
390                 395                 400                 405 ggc cct cag cag aac att cag ctc att aac acc aac ggc agt tgg cac        1603
Gly Pro Gln Gln Asn Ile Gln Leu Ile Asn Thr Asn Gly Ser Trp His
            410                 415                 420 atc aac cgt act gcc ttg aat tgc aat gac tcc ttg aac acc ggc ttt        1651
Ile Asn Arg Thr Ala Leu Asn Cys Asn Asp Ser Leu Asn Thr Gly Phe
                425                 430                 435 ctc gcg gcc ttg ttc tac acc aac cgc ttt aac tcg tca ggg tgt cca        1699
Leu Ala Ala Leu Phe Tyr Thr Asn Arg Phe Asn Ser Ser Gly Cys Pro
        440                 445                 450 ggg cgc ctg tcc gcc tgc cgc aac atc gag gct ttc cgg ata ggg tgg        1747
Gly Arg Leu Ser Ala Cys Arg Asn Ile Glu Ala Phe Arg Ile Gly Trp
    455                 460                 465 ggc acc cta cag tac gag gat aat gtc acc aat cca gag gat atg agg        1795
Gly Thr Leu Gln Tyr Glu Asp Asn Val Thr Asn Pro Glu Asp Met Arg
470                 475                 480                 485 ccg tac tgc tgg cac tac ccc cca aag ccg tgt ggc gta gtc ccc gcg        1843
Pro Tyr Cys Trp His Tyr Pro Pro Lys Pro Cys Gly Val Val Pro Ala
            490                 495                 500 agg tct gtg tgt ggc cca gtg tac tgt ttc acc ccc agc ccg gta gta        1891
Arg Ser Val Cys Gly Pro Val Tyr Cys Phe Thr Pro Ser Pro Val Val
                505                 510                 515 gtg ggc acg acc gac aga cgt gga gtg ccc acc tac aca tgg gga gag        1939
Val Gly Thr Thr Asp Arg Arg Gly Val Pro Thr Tyr Thr Trp Gly Glu
        520                 525                 530 aat gag aca gat gtc ttc cta ctg aac agc acc cga ccg ccg cag ggc        1987
Asn Glu Thr Asp Val Phe Leu Leu Asn Ser Thr Arg Pro Pro Gln Gly
```

```
                Asn Glu Thr Asp Val Phe Leu Leu Asn Ser Thr Arg Pro Pro Gln Gly
                            535                 540                 545 tca tgg ttc ggc tgc acg tgg atg aac tcc act ggt ttc acc aag act                    2035
Ser Trp Phe Gly Cys Thr Trp Met Asn Ser Thr Gly Phe Thr Lys Thr
550                 555                 560                 565 tgt ggc gcg cca cct tgc cgc acc aga gct gac ttc aac gcc agc acg                    2083
Cys Gly Ala Pro Pro Cys Arg Thr Arg Ala Asp Phe Asn Ala Ser Thr
                570                 575                 580 gac ttg ttg tgc cct acg gat tgt ttt agg aag cat cct gat gcc act                    2131
Asp Leu Leu Cys Pro Thr Asp Cys Phe Arg Lys His Pro Asp Ala Thr
            585                 590                 595 tat att aag tgt ggt tct ggg ccc tgg ctc aca cca aag tgc ctg gtc                    2179
Tyr Ile Lys Cys Gly Ser Gly Pro Trp Leu Thr Pro Lys Cys Leu Val
        600                 605                 610 cac tac cct tac aga ctc tgg cat tac ccc tgc aca gtc aat ttt acc                    2227
His Tyr Pro Tyr Arg Leu Trp His Tyr Pro Cys Thr Val Asn Phe Thr
    615                 620                 625 atc ttc aag ata aga atg tat gta ggg ggg gtt gag cac agg ctc acg                    2275
Ile Phe Lys Ile Arg Met Tyr Val Gly Gly Val Glu His Arg Leu Thr
630                 635                 640                 645 gcc gca tgc aac ttc act cgt ggg gat cgc tgc gac ttg gag gac agg                    2323
Ala Ala Cys Asn Phe Thr Arg Gly Asp Arg Cys Asp Leu Glu Asp Arg
                650                 655                 660 gac agg agt cag ctg tct cct ctg ttg cac tct acc acg gaa tgg gcc                    2371
Asp Arg Ser Gln Leu Ser Pro Leu Leu His Ser Thr Thr Glu Trp Ala
            665                 670                 675 atc ctg ccc tgc acc tac tca gac tta ccc gct ttg tca act ggt ctt                    2419
Ile Leu Pro Cys Thr Tyr Ser Asp Leu Pro Ala Leu Ser Thr Gly Leu
        680                 685                 690 ctc cac ctt cac cag aac atc gtg gac gta caa tac atg tat ggc ctc                    2467
Leu His Leu His Gln Asn Ile Val Asp Val Gln Tyr Met Tyr Gly Leu
    695                 700                 705 tca cct gct atc aca aaa tac gtc gtt cga tgg gag tgg gtg gta ctc                    2515
Ser Pro Ala Ile Thr Lys Tyr Val Val Arg Trp Glu Trp Val Val Leu
710                 715                 720                 725 tta ttc ctg ctc tta gcg gac gcc aga gtc tgc gcc tgc ttg tgg atg                    2563
Leu Phe Leu Leu Leu Ala Asp Ala Arg Val Cys Ala Cys Leu Trp Met
                730                 735                 740 ctc atc ttg ttg ggc cag gcc gaa gca gca ttg gag aag ttg gtc gtc                    2611
Leu Ile Leu Leu Gly Gln Ala Glu Ala Ala Leu Glu Lys Leu Val Val
            745                 750                 755 ttg cac gct gcg agt gcg gct aac tgc cat ggc ctc cta tat ttt gcc                    2659
Leu His Ala Ala Ser Ala Ala Asn Cys His Gly Leu Leu Tyr Phe Ala
        760                 765                 770 atc ttc ttc gtg gca gct tgg cac atc agg ggt cgg gtg gtc ccc ttg                    2707
Ile Phe Phe Val Ala Ala Trp His Ile Arg Gly Arg Val Val Pro Leu
    775                 780                 785 acc acc tat tgc ctc act ggc cta tgg ccc ttc tgc cta ctg ctc atg                    2755
Thr Thr Tyr Cys Leu Thr Gly Leu Trp Pro Phe Cys Leu Leu Leu Met
790                 795                 800                 805 gca ctg ccc cgg cag gct tat gcc tat gac gca cct gtg cac gga cag                    2803
Ala Leu Pro Arg Gln Ala Tyr Ala Tyr Asp Ala Pro Val His Gly Gln
                810                 815                 820 ata ggc gtg ggt ttg ttg ata ttg atc acc ctc ttc aca ctc acc ccg                    2851
Ile Gly Val Gly Leu Leu Ile Leu Ile Thr Leu Phe Thr Leu Thr Pro
            825                 830                 835 ggg tat aag acc ctc ctc ggc cag tgt ctg tgg tgg ttg tgc tat ctc                    2899
Gly Tyr Lys Thr Leu Leu Gly Gln Cys Leu Trp Trp Leu Cys Tyr Leu
        840                 845                 850 ctg acc ctg ggg gaa gcc atg att cag gag tgg gta cca ccc atg cag                    2947
```

| | | |
|---|---|---|
| Leu Thr Leu Gly Glu Ala Met Ile Gln Glu Trp Val Pro Pro Met Gln<br>855                            860                        865 | |
| gtg cgc ggc ggc cgc gat ggc atc gcg tgg gcc gtc act ata ttc tgc<br>Val Arg Gly Gly Arg Asp Gly Ile Ala Trp Ala Val Thr Ile Phe Cys<br>870                        875                    880                  885 | 2995 |
| ccg ggt gtg gtg ttt gac att acc aaa tgg ctt ttg gcg ttg ctt ggg<br>Pro Gly Val Val Phe Asp Ile Thr Lys Trp Leu Leu Ala Leu Leu Gly<br>890                        895                            900 | 3043 |
| cct gct tac ctc tta agg gcc gct ttg aca cat gtg ccg tac ttc gtc<br>Pro Ala Tyr Leu Leu Arg Ala Ala Leu Thr His Val Pro Tyr Phe Val<br>                  905                        910                        915 | 3091 |
| aga gct cac gct ctg ata agg gta tgc gct ttg gtg aag cag ctc gcg<br>Arg Ala His Ala Leu Ile Arg Val Cys Ala Leu Val Lys Gln Leu Ala<br>920                        925                    930 | 3139 |
| ggg ggt agg tat gtt cag gtg gcg cta ttg gcc ctt ggc agg tgg act<br>Gly Gly Arg Tyr Val Gln Val Ala Leu Leu Ala Leu Gly Arg Trp Thr<br>935                        940                    945 | 3187 |
| ggc acc tac atc tat gac cac ctc aca cct atg tcg gac tgg gcc gct<br>Gly Thr Tyr Ile Tyr Asp His Leu Thr Pro Met Ser Asp Trp Ala Ala<br>950                        955                    960                  965 | 3235 |
| agc ggc ctg cgc gac tta gcg gtc gcc gtg gaa ccc atc atc ttc agt<br>Ser Gly Leu Arg Asp Leu Ala Val Ala Val Glu Pro Ile Ile Phe Ser<br>                  970                        975                        980 | 3283 |
| ccg atg gag aag aag gtc atc gtc tgg gga gcg gag acg gct gca tgt<br>Pro Met Glu Lys Lys Val Ile Val Trp Gly Ala Glu Thr Ala Ala Cys<br>985                        990                            995 | 3331 |
| ggg gac att cta cat gga ctt ccc gtg tcc gcc cga ctc ggc cag gag<br>Gly Asp Ile Leu His Gly Leu Pro Val Ser Ala Arg Leu Gly Gln Glu<br>      1000                   1005                  1010 | 3379 |
| atc ctc ctc ggc cca gct gat ggc tac acc tcc aag ggg tgg aag ctc<br>Ile Leu Leu Gly Pro Ala Asp Gly Tyr Thr Ser Lys Gly Trp Lys Leu<br>1015                  1020                  1025 | 3427 |
| ctt gct ccc atc act gct tat gcc cag caa aca cga ggc ctc ctg ggc<br>Leu Ala Pro Ile Thr Ala Tyr Ala Gln Gln Thr Arg Gly Leu Leu Gly<br>1030                  1035                  1040                  1045 | 3475 |
| gcc ata gtg gtg agt atg acg ggg cgt gac agg aca gaa cag gcc ggg<br>Ala Ile Val Val Ser Met Thr Gly Arg Asp Arg Thr Glu Gln Ala Gly<br>      1050                   1055                  1060 | 3523 |
| gaa gtc caa atc ctg tcc aca gtc tct cag tcc ttc ctc gga aca acc<br>Glu Val Gln Ile Leu Ser Thr Val Ser Gln Ser Phe Leu Gly Thr Thr<br>1065                  1070                  1075 | 3571 |
| atc tcg ggg gtt ttg tgg act gtt tac cac gga gct ggc aac aag act<br>Ile Ser Gly Val Leu Trp Thr Val Tyr His Gly Ala Gly Asn Lys Thr<br>1080                  1085                  1090 | 3619 |
| cta gcc ggc tta cgg ggt ccg gtc acg cag atg tac tcg agt gct gag<br>Leu Ala Gly Leu Arg Gly Pro Val Thr Gln Met Tyr Ser Ser Ala Glu<br>1095                  1100                  1105 | 3667 |
| ggg gac ttg gta ggc tgg ccc agc ccc cct ggg acc aag tct ttg gag<br>Gly Asp Leu Val Gly Trp Pro Ser Pro Pro Gly Thr Lys Ser Leu Glu<br>1110                  1115                  1120                  1125 | 3715 |
| ccg tgc aag tgt gga gcc gtc gac cta tat ctg gtc acg cgg aac gct<br>Pro Cys Lys Cys Gly Ala Val Asp Leu Tyr Leu Val Thr Arg Asn Ala<br>      1130                   1135                  1140 | 3763 |
| gat gtc atc ccg gct cgg aga cgc ggg gac aag cgg gga gca ttg ctc<br>Asp Val Ile Pro Ala Arg Arg Arg Gly Asp Lys Arg Gly Ala Leu Leu<br>1145                  1150                  1155 | 3811 |
| tcc ccg aga ccc att tcg acc ttg aag ggg tcc tcg ggg ggg ccg gtg<br>Ser Pro Arg Pro Ile Ser Thr Leu Lys Gly Ser Ser Gly Gly Pro Val<br>1160                  1165                  1170 | 3859 |
| ctc tgc cct agg ggc cac gtc gtt ggg ctc ttc cga gca gct gtg tgc | 3907 |

```
                 Leu Cys Pro Arg Gly His Val Val Gly Leu Phe Arg Ala Ala Val Cys
                     1175                1180                1185 tct cgg ggc gtg gcc aaa tcc atc gat ttc atc ccc gtt gag aca ctc                    3955
Ser Arg Gly Val Ala Lys Ser Ile Asp Phe Ile Pro Val Glu Thr Leu
1190                1195                1200                1205 gac gtt gtt aca agg tct ccc act ttc agt gac aac agc acg cca ccg                    4003
Asp Val Val Thr Arg Ser Pro Thr Phe Ser Asp Asn Ser Thr Pro Pro
        1210                1215                1220 gct gtg ccc cag acc tat cag gtc ggg tac ttg cat gct cca act ggc                    4051
Ala Val Pro Gln Thr Tyr Gln Val Gly Tyr Leu His Ala Pro Thr Gly
            1225                1230                1235 agt gga aag agc acc aag gtc cct gtc gcg tat gcc gcc cag ggg tac                    4099
Ser Gly Lys Ser Thr Lys Val Pro Val Ala Tyr Ala Ala Gln Gly Tyr
    1240                1245                1250 aaa gta cta gtg ctt aac ccc tcg gta gct gcc acc ctg ggg ttt ggg                    4147
Lys Val Leu Val Leu Asn Pro Ser Val Ala Ala Thr Leu Gly Phe Gly
1255                1260                1265 gcg tac cta tcc aag gca cat ggc atc aat ccc aac att agg act gga                    4195
Ala Tyr Leu Ser Lys Ala His Gly Ile Asn Pro Asn Ile Arg Thr Gly
1270                1275                1280                1285 gtc agg acc gtg atg acc ggg gag gcc atc acg tac tcc aca tat ggc                    4243
Val Arg Thr Val Met Thr Gly Glu Ala Ile Thr Tyr Ser Thr Tyr Gly
        1290                1295                1300 aaa ttt ctc gcc gat ggg ggc tgc gct agc ggc gcc tat gac atc atc                    4291
Lys Phe Leu Ala Asp Gly Gly Cys Ala Ser Gly Ala Tyr Asp Ile Ile
            1305                1310                1315 ata tgc gat gaa tgc cac gct gtg gat gct acc tcc att ctc ggc atc                    4339
Ile Cys Asp Glu Cys His Ala Val Asp Ala Thr Ser Ile Leu Gly Ile
        1320                1325                1330 gga acg gtc ctt gat caa gca gag aca gcc ggg gtc aga cta act gtg                    4387
Gly Thr Val Leu Asp Gln Ala Glu Thr Ala Gly Val Arg Leu Thr Val
    1335                1340                1345 ctg gct acg gcc aca ccc ccc ggg tca gtg aca acc ccc cat ccc gat                    4435
Leu Ala Thr Ala Thr Pro Pro Gly Ser Val Thr Thr Pro His Pro Asp
1350                1355                1360                1365 ata gaa gag gta ggc ctc ggg cgg gag ggt gag atc ccc ttc tat ggg                    4483
Ile Glu Glu Val Gly Leu Gly Arg Glu Gly Glu Ile Pro Phe Tyr Gly
        1370                1375                1380 agg gcg att ccc cta tcc tgc atc aag gga ggg aga cac ctg att ttc                    4531
Arg Ala Ile Pro Leu Ser Cys Ile Lys Gly Gly Arg His Leu Ile Phe
            1385                1390                1395 tgc cac tca aag aaa aag tgt gac gag ctc gcg gcg gcc ctt cgg ggc                    4579
Cys His Ser Lys Lys Lys Cys Asp Glu Leu Ala Ala Ala Leu Arg Gly
        1400                1405                1410 atg ggc ttg aat gcc gtg gca tac tat aga ggg ttg gac gtc tcc ata                    4627
Met Gly Leu Asn Ala Val Ala Tyr Tyr Arg Gly Leu Asp Val Ser Ile
    1415                1420                1425 ata cca gct cag gga gat gtg gtg gtc gtc gcc acc gac gcc ctc atg                    4675
Ile Pro Ala Gln Gly Asp Val Val Val Val Ala Thr Asp Ala Leu Met
1430                1435                1440                1445 acg ggg tac act gga gac ttt gac tcc gtg atc gac tgc aat gta gcg                    4723
Thr Gly Tyr Thr Gly Asp Phe Asp Ser Val Ile Asp Cys Asn Val Ala
        1450                1455                1460 gtc acc caa gct gtc gac ttc agc ctg gac ccc acc ttc act ata acc                    4771
Val Thr Gln Ala Val Asp Phe Ser Leu Asp Pro Thr Phe Thr Ile Thr
            1465                1470                1475 aca cag act gtc cca caa gac gct gtc tca cgc agt cag cgc cgc ggg                    4819
Thr Gln Thr Val Pro Gln Asp Ala Val Ser Arg Ser Gln Arg Arg Gly
        1480                1485                1490 cgc aca ggt aga gga aga cag ggc act tat agg tat gtt tcc act ggt                    4867
```

```
                Arg Thr Gly Arg Gly Arg Gln Gly Thr Tyr Arg Tyr Val Ser Thr Gly
                    1495                1500                1505 gaa cga gcc tca gga atg ttt gac agt gta gtg ctt tgt gag tgc tac        4915
Glu Arg Ala Ser Gly Met Phe Asp Ser Val Val Leu Cys Glu Cys Tyr
1510                1515                1520                1525 gac gca ggg gct gcg tgg tac gat ctc aca cca gcg gag acc acc gtc        4963
Asp Ala Gly Ala Ala Trp Tyr Asp Leu Thr Pro Ala Glu Thr Thr Val
            1530                1535                1540 agg ctt aga gcg tat ttc aac acg ccc ggc cta ccc gtg tgt caa gac        5011
Arg Leu Arg Ala Tyr Phe Asn Thr Pro Gly Leu Pro Val Cys Gln Asp
        1545                1550                1555 cat ctt gaa ttt tgg gag gca gtt ttc acc ggc ctc aca cac ata gac        5059
His Leu Glu Phe Trp Glu Ala Val Phe Thr Gly Leu Thr His Ile Asp
    1560                1565                1570 gcc cac ttc ctc tcc caa aca aag caa gcg ggg gag aac ttc gcg tac        5107
Ala His Phe Leu Ser Gln Thr Lys Gln Ala Gly Glu Asn Phe Ala Tyr
1575                1580                1585 cta gta gcc tac caa gct acg gtg tgc gcc aga gcc aag gcc cct ccc        5155
Leu Val Ala Tyr Gln Ala Thr Val Cys Ala Arg Ala Lys Ala Pro Pro
1590                1595                1600                1605 ccg tcc tgg gac gcc atg tgg aag tgc ctg gcc cga ctc aag cct acg        5203
Pro Ser Trp Asp Ala Met Trp Lys Cys Leu Ala Arg Leu Lys Pro Thr
            1610                1615                1620 ctt gcg ggc ccc aca cct ctc ctg tac cgt ttg ggc cct att acc aat        5251
Leu Ala Gly Pro Thr Pro Leu Leu Tyr Arg Leu Gly Pro Ile Thr Asn
        1625                1630                1635 gag gtc acc ctc aca cac cct ggg acg aag tac atc gcc aca tgc atg        5299
Glu Val Thr Leu Thr His Pro Gly Thr Lys Tyr Ile Ala Thr Cys Met
    1640                1645                1650 caa gct gac ctt gag gtc atg acc agc acg tgg gtc cta gct gga gga        5347
Gln Ala Asp Leu Glu Val Met Thr Ser Thr Trp Val Leu Ala Gly Gly
1655                1660                1665 gtc ctg gca gcc gtc gcc gca tat tgc ctg gcg act gga tgc gtt tcc        5395
Val Leu Ala Ala Val Ala Ala Tyr Cys Leu Ala Thr Gly Cys Val Ser
1670                1675                1680                1685 atc atc ggc cgc ttg cac gtc aac cag cga gtc gtc gtt gcg ccg gat        5443
Ile Ile Gly Arg Leu His Val Asn Gln Arg Val Val Val Ala Pro Asp
            1690                1695                1700 aag gag gtc ctg tat gag gct ttt gat gag atg gag gaa tgc gcc tct        5491
Lys Glu Val Leu Tyr Glu Ala Phe Asp Glu Met Glu Glu Cys Ala Ser
        1705                1710                1715 agg gcg gct ctc atc gaa gag ggg cag cgg ata gcc gag atg ttg aag        5539
Arg Ala Ala Leu Ile Glu Glu Gly Gln Arg Ile Ala Glu Met Leu Lys
    1720                1725                1730 tcc aag atc caa ggc ttg ctg cag cag gcc tct aag cag gcc cag gac        5587
Ser Lys Ile Gln Gly Leu Leu Gln Gln Ala Ser Lys Gln Ala Gln Asp
1735                1740                1745 ata caa ccc gct atg cag gct tca tgg ccc aaa gtg gaa caa ttt tgg        5635
Ile Gln Pro Ala Met Gln Ala Ser Trp Pro Lys Val Glu Gln Phe Trp
1750                1755                1760                1765 gcc aga cac atg tgg aac ttc att agc ggc atc caa tac ctc gca gga        5683
Ala Arg His Met Trp Asn Phe Ile Ser Gly Ile Gln Tyr Leu Ala Gly
            1770                1775                1780 ttg tca aca ctg cca ggg aac ccc gcg gtg gct tcc atg atg gca ttc        5731
Leu Ser Thr Leu Pro Gly Asn Pro Ala Val Ala Ser Met Met Ala Phe
        1785                1790                1795 agt gcc gcc ctc acc agt ccg ttg tcg acc agt acc atc ctt ctc            5779
Ser Ala Ala Leu Thr Ser Pro Leu Ser Thr Ser Thr Ile Leu Leu
    1800                1805                1810 aac atc atg gga ggc tgg tta gcg tcc cag atc gca cca ccc gcg ggg        5827
```

```
                Asn Ile Met Gly Gly Trp Leu Ala Ser Gln Ile Ala Pro Pro Ala Gly
                    1815                1820                1825 gcc acc ggc ttt gtc gtc agt ggc ctg gtg ggg gct gcc gtg ggc agc        5875
Ala Thr Gly Phe Val Val Ser Gly Leu Val Gly Ala Ala Val Gly Ser
1830            1835                1840                1845 ata ggc ctg ggt aag gtg ctg gtg gac atc ctg gca gga tat ggt gcg        5923
Ile Gly Leu Gly Lys Val Leu Val Asp Ile Leu Ala Gly Tyr Gly Ala
        1850                1855                1860 ggc att tcg ggg gcc ctc gtc gca ttc aag atc atg tct ggc gag aag        5971
Gly Ile Ser Gly Ala Leu Val Ala Phe Lys Ile Met Ser Gly Glu Lys
            1865                1870                1875 ccc tct atg gaa gat gtc atc aat cta ctg cct ggg atc ctg tct ccg        6019
Pro Ser Met Glu Asp Val Ile Asn Leu Leu Pro Gly Ile Leu Ser Pro
        1880                1885                1890 gga gcc ctg gtg gtg ggg gtc atc tgc gcg gcc att ctg cgc cgc cac        6067
Gly Ala Leu Val Val Gly Val Ile Cys Ala Ala Ile Leu Arg Arg His
    1895                1900                1905 gtg gga ccg ggg gag ggc gcg gtc caa tgg atg aac agg ctt att gcc        6115
Val Gly Pro Gly Glu Gly Ala Val Gln Trp Met Asn Arg Leu Ile Ala
1910            1915                1920                1925 ttt gct tcc aga gga aac cac gtc gcc cct act cac tac gtg acg gag        6163
Phe Ala Ser Arg Gly Asn His Val Ala Pro Thr His Tyr Val Thr Glu
                1930                1935                1940 tcg gat gcg tcg cag cgt gtg acc caa cta ctt ggc tct ctt act ata        6211
Ser Asp Ala Ser Gln Arg Val Thr Gln Leu Leu Gly Ser Leu Thr Ile
            1945                1950                1955 acc agc cta ctc aga aga ctc cac aat tgg ata act gag gac tgc ccc        6259
Thr Ser Leu Leu Arg Arg Leu His Asn Trp Ile Thr Glu Asp Cys Pro
        1960                1965                1970 atc cca tgc tcc gga tcc tgg ctc cgc gac gtg tgg gac tgg gtt tgc        6307
Ile Pro Cys Ser Gly Ser Trp Leu Arg Asp Val Trp Asp Trp Val Cys
    1975                1980                1985 acc atc ttg aca gac ttc aaa aat tgg ctg acc tct aaa ttg ttc ccc        6355
Thr Ile Leu Thr Asp Phe Lys Asn Trp Leu Thr Ser Lys Leu Phe Pro
1990            1995                2000                2005 aag ctg ccc ggc ctc ccc ttc atc tct tgt caa aag ggg tac aag ggt        6403
Lys Leu Pro Gly Leu Pro Phe Ile Ser Cys Gln Lys Gly Tyr Lys Gly
                2010                2015                2020 gtg tgg gcc ggc act ggc atc atg acc acg cgc tgc cct tgc ggc gcc        6451
Val Trp Ala Gly Thr Gly Ile Met Thr Thr Arg Cys Pro Cys Gly Ala
            2025                2030                2035 aac atc tct ggc aat gtc cgc ctg ggc tct atg agg atc aca ggg cct        6499
Asn Ile Ser Gly Asn Val Arg Leu Gly Ser Met Arg Ile Thr Gly Pro
        2040                2045                2050 aaa acc tgc atg aac acc tgg cag ggg acc ttt cct atc aat tgc tac        6547
Lys Thr Cys Met Asn Thr Trp Gln Gly Thr Phe Pro Ile Asn Cys Tyr
    2055                2060                2065 acg gag ggc cag tgc gcg ccg aaa ccc ccc acg aac tac aag acc gcc        6595
Thr Glu Gly Gln Cys Ala Pro Lys Pro Pro Thr Asn Tyr Lys Thr Ala
2070            2075                2080                2085 atc tgg agg gtg gcg gcc tcg gag tac gcg gag gtg acg cag cat ggg        6643
Ile Trp Arg Val Ala Ala Ser Glu Tyr Ala Glu Val Thr Gln His Gly
                2090                2095                2100 tcg tac tcc tat gta aca gga ctg acc act gac aat ctg aaa att cct        6691
Ser Tyr Ser Tyr Val Thr Gly Leu Thr Thr Asp Asn Leu Lys Ile Pro
            2105                2110                2115 tgc caa cta cct tct cca gag ttt ttc tcc tgg gtg gac ggt gtg cag        6739
Cys Gln Leu Pro Ser Pro Glu Phe Phe Ser Trp Val Asp Gly Val Gln
        2120                2125                2130 atc cat agg ttt gca ccc aca cca aag ccg ttt ttc cgg gat gag gtc        6787
```

```
                Ile His Arg Phe Ala Pro Thr Pro Lys Pro Phe Phe Arg Asp Glu Val
                    2135                2140                2145 tcg ttc tgc gtt ggg ctt aat tcc tat gct gtc ggg tcc cag ctt ccc         6835
Ser Phe Cys Val Gly Leu Asn Ser Tyr Ala Val Gly Ser Gln Leu Pro
2150                2155                2160                2165 tgt gaa cct gag ccc gac gca gac gta ttg agg tcc atg cta aca gat         6883
Cys Glu Pro Glu Pro Asp Ala Asp Val Leu Arg Ser Met Leu Thr Asp
                2170                2175                2180 ccg ccc cac atc acg gcg gag act gcg gcg cgg cgc ttg gca cgg gga         6931
Pro Pro His Ile Thr Ala Glu Thr Ala Ala Arg Arg Leu Ala Arg Gly
            2185                2190                2195 tca cct cca tct gag gcg agc tcc tca gtg agc cag cta tca gca ccg         6979
Ser Pro Pro Ser Glu Ala Ser Ser Ser Val Ser Gln Leu Ser Ala Pro
        2200                2205                2210 tcg ctg cgg gcc acc tgc acc acc cac agc aac acc tat gac gtg gac         7027
Ser Leu Arg Ala Thr Cys Thr Thr His Ser Asn Thr Tyr Asp Val Asp
    2215                2220                2225 atg gtc gat gca aac ctg ctc atg gag ggc ggt gtg gct cag aca gag         7075
Met Val Asp Ala Asn Leu Leu Met Glu Gly Gly Val Ala Gln Thr Glu
2230                2235                2240                2245 cct gag tcc agg gtg ccc gtt ctg gac ttt ctc gag cca atg gcc gag         7123
Pro Glu Ser Arg Val Pro Val Leu Asp Phe Leu Glu Pro Met Ala Glu
                2250                2255                2260 gaa gag agc gac ctt gag ccc tca ata cca tcg gag tgc atg ctc ccc         7171
Glu Glu Ser Asp Leu Glu Pro Ser Ile Pro Ser Glu Cys Met Leu Pro
            2265                2270                2275 agg agc ggg ttt cca cgg gcc tta ccg gct tgg gca cgg cct gac tac         7219
Arg Ser Gly Phe Pro Arg Ala Leu Pro Ala Trp Ala Arg Pro Asp Tyr
        2280                2285                2290 aac ccg ccg ctc gtg gaa tcg tgg agg agg cca gat tac caa ccg ccc         7267
Asn Pro Pro Leu Val Glu Ser Trp Arg Arg Pro Asp Tyr Gln Pro Pro
    2295                2300                2305 acc gtt gct ggt tgt gct ctc ccc ccc ccc aag aag gcc ccg acg cct         7315
Thr Val Ala Gly Cys Ala Leu Pro Pro Pro Lys Lys Ala Pro Thr Pro
2310                2315                2320                2325 ccc cca agg aga cgc cgg aca gtg ggt ctg agc gag agc acc ata tca         7363
Pro Pro Arg Arg Arg Arg Thr Val Gly Leu Ser Glu Ser Thr Ile Ser
                2330                2335                2340 gaa gcc ctc cag caa ctg gcc atc aag acc ttt ggc cag ccc ccc tcg         7411
Glu Ala Leu Gln Gln Leu Ala Ile Lys Thr Phe Gly Gln Pro Pro Ser
            2345                2350                2355 agc ggt gat gca ggc tcg tcc acg ggg gcg ggc gcc gcc gaa tcc ggc         7459
Ser Gly Asp Ala Gly Ser Ser Thr Gly Ala Gly Ala Ala Glu Ser Gly
        2360                2365                2370 ggt ccg acg tcc cct ggt gag ccg gcc ccc tca gag aca ggt tcc gcc         7507
Gly Pro Thr Ser Pro Gly Glu Pro Ala Pro Ser Glu Thr Gly Ser Ala
    2375                2380                2385 tcc tct atg ccc ccc ctc gag ggg gag cct gga gat ccg gac ctg gag         7555
Ser Ser Met Pro Pro Leu Glu Gly Glu Pro Gly Asp Pro Asp Leu Glu
2390                2395                2400                2405 tct gat cag gta gag ctt caa cct ccc ccc cag ggg ggg ggg gta gct         7603
Ser Asp Gln Val Glu Leu Gln Pro Pro Pro Gln Gly Gly Gly Val Ala
                2410                2415                2420 ccc ggt tcg ggc tcg ggg tct tgg tct act tgc tcc gag gag gac gat         7651
Pro Gly Ser Gly Ser Gly Ser Trp Ser Thr Cys Ser Glu Glu Asp Asp
            2425                2430                2435 acc acc gtg tgc tgc tcc atg tca tac tcc tgg acc ggg gct cta ata         7699
Thr Thr Val Cys Cys Ser Met Ser Tyr Ser Trp Thr Gly Ala Leu Ile
        2440                2445                2450 act ccc tgt agc ccc gaa gag gaa aag ttg cca atc aac cct ttg agt         7747
```

-continued

| | | |
|---|---|---|
| Thr Pro Cys Ser Pro Glu Glu Glu Lys Leu Pro Ile Asn Pro Leu Ser<br>    2455                 2460                 2465 | | |
| aac tcg ctg ttg cga tac cat aac aag gtg tac tgt aca aca tca aag<br>Asn Ser Leu Leu Arg Tyr His Asn Lys Val Tyr Cys Thr Thr Ser Lys<br>2470                 2475                 2480                 2485 | 7795 | |
| agc gcc tca cag agg gct aaa aag gta act ttt gac agg acg caa gtg<br>Ser Ala Ser Gln Arg Ala Lys Lys Val Thr Phe Asp Arg Thr Gln Val<br>                2490                 2495                 2500 | 7843 | |
| ctc gac gcc cat tat gac tca gtc tta aag gac atc aag cta gcg gct<br>Leu Asp Ala His Tyr Asp Ser Val Leu Lys Asp Ile Lys Leu Ala Ala<br>            2505                 2510                 2515 | 7891 | |
| tcc aag gtc agc gca agg ctc ctc acc ttg gag gag gcg tgc cag ttg<br>Ser Lys Val Ser Ala Arg Leu Leu Thr Leu Glu Glu Ala Cys Gln Leu<br>2520                 2525                 2530 | 7939 | |
| act cca ccc cat tct gca aga tcc aag tat gga ttc ggg gcc aag gag<br>Thr Pro Pro His Ser Ala Arg Ser Lys Tyr Gly Phe Gly Ala Lys Glu<br>            2535                 2540                 2545 | 7987 | |
| gtc cgc agc ttg tcc ggg agg gcc gtt aac cac atc aag tcc gtg tgg<br>Val Arg Ser Leu Ser Gly Arg Ala Val Asn His Ile Lys Ser Val Trp<br>2550                 2555                 2560                 2565 | 8035 | |
| aag gac ctc ctg gaa gac cca caa aca cca att ccc aca acc atc atg<br>Lys Asp Leu Leu Glu Asp Pro Gln Thr Pro Ile Pro Thr Thr Ile Met<br>                2570                 2575                 2580 | 8083 | |
| gcc aaa aat gag gtg ttc tgc gtg gac ccc gcc aag ggg ggt aag aaa<br>Ala Lys Asn Glu Val Phe Cys Val Asp Pro Ala Lys Gly Gly Lys Lys<br>            2585                 2590                 2595 | 8131 | |
| cca gct cgc ctc atc gtt tac cct gac ctc ggc gtc cgg gtc tgc gag<br>Pro Ala Arg Leu Ile Val Tyr Pro Asp Leu Gly Val Arg Val Cys Glu<br>        2600                 2605                 2610 | 8179 | |
| aaa atg gcc ctc tat gac att aca caa aag ctt cct cag gcg gta atg<br>Lys Met Ala Leu Tyr Asp Ile Thr Gln Lys Leu Pro Gln Ala Val Met<br>    2615                 2620                 2625 | 8227 | |
| gga gct tcc tat ggc ttc cag tac tcc cct gcc caa cgg gtg gag tat<br>Gly Ala Ser Tyr Gly Phe Gln Tyr Ser Pro Ala Gln Arg Val Glu Tyr<br>2630                 2635                 2640                 2645 | 8275 | |
| ctc ttg aaa gca tgg gcg gaa aag aag gac ccc atg ggt ttt tcg tat<br>Leu Leu Lys Ala Trp Ala Glu Lys Lys Asp Pro Met Gly Phe Ser Tyr<br>                2650                 2655                 2660 | 8323 | |
| gat acc cga tgc ttc gac tca acc gtc act gag aga gac atc agg acc<br>Asp Thr Arg Cys Phe Asp Ser Thr Val Thr Glu Arg Asp Ile Arg Thr<br>            2665                 2670                 2675 | 8371 | |
| gag gag tcc ata tac cag gcc tgc tcc ctg ccc gag gag gcc cgc act<br>Glu Glu Ser Ile Tyr Gln Ala Cys Ser Leu Pro Glu Glu Ala Arg Thr<br>        2680                 2685                 2690 | 8419 | |
| gcc ata cac tcg ctg act gag aga ctt tac gta gga ggg ccc atg ttc<br>Ala Ile His Ser Leu Thr Glu Arg Leu Tyr Val Gly Gly Pro Met Phe<br>    2695                 2700                 2705 | 8467 | |
| aac agc aag ggt caa acc tgc ggt tac aga cgt tgc cgc gcc agc ggg<br>Asn Ser Lys Gly Gln Thr Cys Gly Tyr Arg Arg Cys Arg Ala Ser Gly<br>2710                 2715                 2720                 2725 | 8515 | |
| gtg cta acc act agc atg ggt aac acc atc aca tgc tat gtg aaa gcc<br>Val Leu Thr Thr Ser Met Gly Asn Thr Ile Thr Cys Tyr Val Lys Ala<br>                2730                 2735                 2740 | 8563 | |
| cta gcg gcc tgc aag gct gcg ggg ata gtt gcg ccc aca atg ctg gta<br>Leu Ala Ala Cys Lys Ala Ala Gly Ile Val Ala Pro Thr Met Leu Val<br>            2745                 2750                 2755 | 8611 | |
| tgc ggc gat gac cta gta gtc atc tca gaa agc cag ggg act gag gag<br>Cys Gly Asp Asp Leu Val Val Ile Ser Glu Ser Gln Gly Thr Glu Glu<br>        2760                 2765                 2770 | 8659 | |
| gac gag cgg aac ctg aga gcc ttc acg gag gcc atg acc agg tac tct | 8707 | |

-continued

```
              Asp Glu Arg Asn Leu Arg Ala Phe Thr Glu Ala Met Thr Arg Tyr Ser
                  2775                2780                2785 gcc cct cct ggt gat ccc ccc aga ccg gaa tat gac ctg gag cta ata           8755
Ala Pro Pro Gly Asp Pro Pro Arg Pro Glu Tyr Asp Leu Glu Leu Ile
2790                2795                2800                2805 aca tcc tgt tcc tca aat gtg tct gtg gcg ttg ggc ccg cgg ggc cgc           8803
Thr Ser Cys Ser Ser Asn Val Ser Val Ala Leu Gly Pro Arg Gly Arg
                2810                2815                2820 cgc aga tac tac ctg acc aga gac cca acc act cca ctc gcc cgg gct           8851
Arg Arg Tyr Tyr Leu Thr Arg Asp Pro Thr Thr Pro Leu Ala Arg Ala
            2825                2830                2835 gcc tgg gaa aca gtt aga cac tcc cct atc aat tca tgg ctg gga aac           8899
Ala Trp Glu Thr Val Arg His Ser Pro Ile Asn Ser Trp Leu Gly Asn
2840                2845                2850 atc atc cag tat gct cca acc ata tgg gtt cgc atg gtc cta atg aca           8947
Ile Ile Gln Tyr Ala Pro Thr Ile Trp Val Arg Met Val Leu Met Thr
        2855                2860                2865 cac ttc ttc tcc att ctc atg gtc caa gac acc ctg gac cag aac ctc           8995
His Phe Phe Ser Ile Leu Met Val Gln Asp Thr Leu Asp Gln Asn Leu
2870                2875                2880                2885 aac ttt gag atg tat gga tca gta tac tcc gtg aat cct ttg gac ctt           9043
Asn Phe Glu Met Tyr Gly Ser Val Tyr Ser Val Asn Pro Leu Asp Leu
                2890                2895                2900 cca gcc ata att gag agg tta cac ggg ctt gac gcc ttt tct atg cac           9091
Pro Ala Ile Ile Glu Arg Leu His Gly Leu Asp Ala Phe Ser Met His
            2905                2910                2915 aca tac tct cac cac gaa ctg acg cgg gtg gct tca gcc ctc aga aaa           9139
Thr Tyr Ser His His Glu Leu Thr Arg Val Ala Ser Ala Leu Arg Lys
2920                2925                2930 ctt ggg gcg cca ccc ctc agg gtg tgg aag agt cgg gct cgc gca gtc           9187
Leu Gly Ala Pro Pro Leu Arg Val Trp Lys Ser Arg Ala Arg Ala Val
        2935                2940                2945 agg gcg tcc ctc atc tcc cgt gga ggg aaa gcg gcc gtt tgc ggc cga           9235
Arg Ala Ser Leu Ile Ser Arg Gly Gly Lys Ala Ala Val Cys Gly Arg
2950                2955                2960                2965 tat ctc ttc aat tgg gcg gtg aag acc aag ctc aaa ctc act cca ttg           9283
Tyr Leu Phe Asn Trp Ala Val Lys Thr Lys Leu Lys Leu Thr Pro Leu
                2970                2975                2980 ccg gag gcg cgc cta ctg gac tta tcc agt tgg ttc acc gtc ggc gcc           9331
Pro Glu Ala Arg Leu Leu Asp Leu Ser Ser Trp Phe Thr Val Gly Ala
            2985                2990                2995 ggc ggg ggc gac att ttt cac agc gtg tcg cgc gcc cga ccc cgc tca           9379
Gly Gly Gly Asp Ile Phe His Ser Val Ser Arg Ala Arg Pro Arg Ser
3000                3005                3010 tta ctc ttc ggc cta ctc cta ctt ttc gta ggg gta ggc ctc ttc cta           9427
Leu Leu Phe Gly Leu Leu Leu Leu Phe Val Gly Val Gly Leu Phe Leu
        3015                3020                3025 ctc ccc gct cgg tag agcggcacac actaggtaca ctccatagct aactgttcct           9482
Leu Pro Ala Arg
3030 tttttttttt tttttttttt tttttttttt tttttttttt ttcttttttt tttttttccc         9542 tctttcttcc cttctcatct tattctactt tctttcttgg tggctccatc ttagccctag         9602 tcacggctag ctgtgaaagg tccgtgagcc gcatgactgc agagagtgcc gtaactggtc         9662 tctctgcaga tcatgt                                                         9678

<210> SEQ ID NO 4
<211> LENGTH: 3033
<212> TYPE: PRT
<213> ORGANISM: Hepatitis C virus
```

<400> SEQUENCE: 4

```
Met Ser Thr Asn Pro Lys Pro Gln Arg Lys Thr Lys Arg Asn Thr Asn
 1               5                  10                  15

Arg Arg Pro Glu Asp Val Lys Phe Pro Gly Gly Gly Gln Ile Val Gly
            20                  25                  30

Gly Val Tyr Leu Leu Pro Arg Arg Gly Pro Arg Leu Gly Val Arg Thr
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ala Trp Gly Lys Pro Gly
65                  70                  75                  80

Arg Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
130                 135                 140

Ser Gly Ala Ala Arg Ala Val Ala His Gly Val Arg Val Leu Glu Asp
145                 150                 155                 160

Gly Val Asn Tyr Ala Thr Gly Asn Leu Pro Gly Phe Pro Phe Ser Ile
                165                 170                 175

Phe Leu Leu Ala Leu Leu Ser Cys Ile Thr Val Pro Val Ser Ala Ala
            180                 185                 190

Gln Val Lys Asn Thr Ser Ser Tyr Met Val Thr Asn Asp Cys Ser
        195                 200                 205

Asn Asp Ser Ile Thr Trp Gln Leu Glu Ala Ala Val Leu His Val Pro
    210                 215                 220

Gly Cys Val Pro Cys Glu Arg Val Gly Asn Thr Ser Arg Cys Trp Val
225                 230                 235                 240

Pro Val Ser Pro Asn Met Ala Val Arg Gln Pro Gly Ala Leu Thr Gln
                245                 250                 255

Gly Leu Arg Thr His Ile Asp Met Val Val Met Ser Ala Thr Phe Cys
            260                 265                 270

Ser Ala Leu Tyr Val Gly Asp Leu Cys Gly Gly Val Met Leu Ala Ala
        275                 280                 285

Gln Val Phe Ile Val Ser Pro Gln Tyr His Trp Phe Val Gln Glu Cys
290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Val Met Arg Val Pro Glu Val Ile Ile Asp Ile Val Ser Gly Ala His
            340                 345                 350

Trp Gly Val Met Phe Gly Leu Ala Tyr Phe Ser Met Gln Gly Ala Trp
        355                 360                 365

Ala Lys Val Ile Val Ile Leu Leu Ala Ala Gly Val Asp Ala Gly
370                 375                 380

Thr Thr Thr Val Gly Gly Ala Val Ala Arg Ser Thr Asn Val Ile Ala
385                 390                 395                 400

Gly Val Phe Ser His Gly Pro Gln Gln Asn Ile Gln Leu Ile Asn Thr
                405                 410                 415
```

```
Asn Gly Ser Trp His Ile Asn Arg Thr Ala Leu Asn Cys Asn Asp Ser
            420                 425                 430
Leu Asn Thr Gly Phe Leu Ala Ala Leu Phe Tyr Thr Asn Arg Phe Asn
        435                 440                 445
Ser Ser Gly Cys Pro Gly Arg Leu Ser Ala Cys Arg Asn Ile Glu Ala
    450                 455                 460
Phe Arg Ile Gly Trp Gly Thr Leu Gln Tyr Glu Asp Asn Val Thr Asn
465                 470                 475                 480
Pro Glu Asp Met Arg Pro Tyr Cys Trp His Tyr Pro Pro Lys Pro Cys
                485                 490                 495
Gly Val Val Pro Ala Arg Ser Val Cys Gly Pro Val Tyr Cys Phe Thr
            500                 505                 510
Pro Ser Pro Val Val Gly Thr Thr Asp Arg Arg Gly Val Pro Thr
        515                 520                 525
Tyr Thr Trp Gly Glu Asn Glu Thr Asp Val Phe Leu Leu Asn Ser Thr
    530                 535                 540
Arg Pro Pro Gln Gly Ser Trp Phe Gly Cys Thr Trp Met Asn Ser Thr
545                 550                 555                 560
Gly Phe Thr Lys Thr Cys Gly Ala Pro Pro Cys Arg Thr Arg Ala Asp
                565                 570                 575
Phe Asn Ala Ser Thr Asp Leu Leu Cys Pro Thr Asp Cys Phe Arg Lys
            580                 585                 590
His Pro Asp Ala Thr Tyr Ile Lys Cys Gly Ser Gly Pro Trp Leu Thr
        595                 600                 605
Pro Lys Cys Leu Val His Tyr Pro Tyr Arg Leu Trp His Tyr Pro Cys
    610                 615                 620
Thr Val Asn Phe Thr Ile Phe Lys Ile Arg Met Tyr Val Gly Gly Val
625                 630                 635                 640
Glu His Arg Leu Thr Ala Ala Cys Asn Phe Thr Arg Gly Asp Arg Cys
                645                 650                 655
Asp Leu Glu Asp Arg Asp Arg Ser Gln Leu Ser Pro Leu Leu His Ser
            660                 665                 670
Thr Thr Glu Trp Ala Ile Leu Pro Cys Thr Tyr Ser Asp Leu Pro Ala
        675                 680                 685
Leu Ser Thr Gly Leu Leu His Leu His Gln Asn Ile Val Asp Val Gln
    690                 695                 700
Tyr Met Tyr Gly Leu Ser Pro Ala Ile Thr Lys Tyr Val Val Arg Trp
705                 710                 715                 720
Glu Trp Val Val Leu Leu Phe Leu Leu Leu Ala Asp Ala Arg Val Cys
                725                 730                 735
Ala Cys Leu Trp Met Leu Ile Leu Leu Gly Gln Ala Glu Ala Ala Leu
            740                 745                 750
Glu Lys Leu Val Val Leu His Ala Ala Ser Ala Ala Asn Cys His Gly
        755                 760                 765
Leu Leu Tyr Phe Ala Ile Phe Phe Val Ala Trp His Ile Arg Gly
    770                 775                 780
Arg Val Val Pro Leu Thr Thr Tyr Cys Leu Thr Gly Leu Trp Pro Phe
785                 790                 795                 800
Cys Leu Leu Leu Met Ala Leu Pro Arg Gln Ala Tyr Ala Tyr Asp Ala
                805                 810                 815
Pro Val His Gly Gln Ile Gly Val Gly Leu Leu Ile Leu Ile Thr Leu
            820                 825                 830
Phe Thr Leu Thr Pro Gly Tyr Lys Thr Leu Leu Gly Gln Cys Leu Trp
```

```
                835              840              845
Trp Leu Cys Tyr Leu Leu Thr Leu Gly Glu Ala Met Ile Gln Glu Trp
    850              855              860
Val Pro Pro Met Gln Val Arg Gly Gly Arg Asp Gly Ile Ala Trp Ala
865              870              875              880
Val Thr Ile Phe Cys Pro Gly Val Val Phe Asp Ile Thr Lys Trp Leu
                885              890              895
Leu Ala Leu Leu Gly Pro Ala Tyr Leu Arg Ala Ala Leu Thr His
        900              905              910
Val Pro Tyr Phe Val Arg Ala His Ala Leu Ile Arg Val Cys Ala Leu
        915              920              925
Val Lys Gln Leu Ala Gly Gly Arg Tyr Val Gln Val Ala Leu Leu Ala
    930              935              940
Leu Gly Arg Trp Thr Gly Thr Tyr Ile Tyr Asp His Leu Thr Pro Met
945              950              955              960
Ser Asp Trp Ala Ala Ser Gly Leu Arg Asp Leu Ala Val Ala Val Glu
                965              970              975
Pro Ile Ile Phe Ser Pro Met Glu Lys Lys Val Ile Val Trp Gly Ala
            980              985              990
Glu Thr Ala Ala Cys Gly Asp Ile Leu His Gly Leu Pro Val Ser Ala
        995             1000             1005
Arg Leu Gly Gln Glu Ile Leu Leu Gly Pro Ala Asp Gly Tyr Thr Ser
   1010             1015             1020
Lys Gly Trp Lys Leu Leu Ala Pro Ile Thr Ala Tyr Ala Gln Gln Thr
1025             1030             1035             1040
Arg Gly Leu Leu Gly Ala Ile Val Val Ser Met Thr Gly Arg Asp Arg
            1045             1050             1055
Thr Glu Gln Ala Gly Glu Val Gln Ile Leu Ser Thr Val Ser Gln Ser
        1060             1065             1070
Phe Leu Gly Thr Thr Ile Ser Gly Val Leu Trp Thr Val Tyr His Gly
    1075             1080             1085
Ala Gly Asn Lys Thr Leu Ala Gly Leu Arg Gly Pro Val Thr Gln Met
    1090             1095             1100
Tyr Ser Ser Ala Glu Gly Asp Leu Val Gly Trp Pro Ser Pro Pro Gly
1105             1110             1115             1120
Thr Lys Ser Leu Glu Pro Cys Lys Cys Gly Ala Val Asp Leu Tyr Leu
            1125             1130             1135
Val Thr Arg Asn Ala Asp Val Ile Pro Ala Arg Arg Arg Gly Asp Lys
        1140             1145             1150
Arg Gly Ala Leu Leu Ser Pro Arg Pro Ile Ser Thr Leu Lys Gly Ser
    1155             1160             1165
Ser Gly Gly Pro Val Leu Cys Pro Arg Gly His Val Val Gly Leu Phe
   1170             1175             1180
Arg Ala Ala Val Cys Ser Arg Gly Val Ala Lys Ser Ile Asp Phe Ile
1185             1190             1195             1200
Pro Val Glu Thr Leu Asp Val Val Thr Arg Ser Pro Thr Phe Ser Asp
            1205             1210             1215
Asn Ser Thr Pro Pro Ala Val Pro Gln Thr Tyr Gln Val Gly Tyr Leu
        1220             1225             1230
His Ala Pro Thr Gly Ser Gly Lys Ser Thr Lys Val Pro Val Ala Tyr
        1235             1240             1245
Ala Ala Gln Gly Tyr Lys Val Leu Val Leu Asn Pro Ser Val Ala Ala
    1250             1255             1260
```

-continued

```
Thr Leu Gly Phe Gly Ala Tyr Leu Ser Lys Ala His Gly Ile Asn Pro
1265                1270                1275                1280

Asn Ile Arg Thr Gly Val Arg Thr Val Met Thr Gly Glu Ala Ile Thr
            1285                1290                1295

Tyr Ser Thr Tyr Gly Lys Phe Leu Ala Asp Gly Gly Cys Ala Ser Gly
        1300                1305                1310

Ala Tyr Asp Ile Ile Cys Asp Glu Cys His Ala Val Asp Ala Thr
    1315                1320                1325

Ser Ile Leu Gly Ile Gly Thr Val Leu Asp Gln Ala Glu Thr Ala Gly
1330                1335                1340

Val Arg Leu Thr Val Leu Ala Thr Ala Thr Pro Pro Gly Ser Val Thr
1345                1350                1355                1360

Thr Pro His Pro Asp Ile Glu Glu Val Gly Leu Gly Arg Glu Gly Glu
            1365                1370                1375

Ile Pro Phe Tyr Gly Arg Ala Ile Pro Leu Ser Cys Ile Lys Gly Gly
        1380                1385                1390

Arg His Leu Ile Phe Cys His Ser Lys Lys Cys Asp Glu Leu Ala
    1395                1400                1405

Ala Ala Leu Arg Gly Met Gly Leu Asn Ala Val Ala Tyr Tyr Arg Gly
1410                1415                1420

Leu Asp Val Ser Ile Ile Pro Ala Gln Gly Asp Val Val Val Ala
1425                1430                1435                1440

Thr Asp Ala Leu Met Thr Gly Tyr Thr Gly Asp Phe Asp Ser Val Ile
            1445                1450                1455

Asp Cys Asn Val Ala Val Thr Gln Ala Val Asp Phe Ser Leu Asp Pro
        1460                1465                1470

Thr Phe Thr Ile Thr Thr Gln Thr Val Pro Gln Asp Ala Val Ser Arg
    1475                1480                1485

Ser Gln Arg Arg Gly Arg Thr Gly Arg Gly Gln Gly Thr Tyr Arg
1490                1495                1500

Tyr Val Ser Thr Gly Glu Arg Ala Ser Gly Met Phe Asp Ser Val Val
1505                1510                1515                1520

Leu Cys Glu Cys Tyr Asp Ala Gly Ala Ala Trp Tyr Asp Leu Thr Pro
            1525                1530                1535

Ala Glu Thr Thr Val Arg Leu Arg Ala Tyr Phe Asn Thr Pro Gly Leu
        1540                1545                1550

Pro Val Cys Gln Asp His Leu Glu Phe Trp Glu Ala Val Phe Thr Gly
    1555                1560                1565

Leu Thr His Ile Asp Ala His Phe Leu Ser Gln Thr Lys Gln Ala Gly
1570                1575                1580

Glu Asn Phe Ala Tyr Leu Val Ala Tyr Gln Ala Thr Val Cys Ala Arg
1585                1590                1595                1600

Ala Lys Ala Pro Pro Pro Ser Trp Asp Ala Met Trp Lys Cys Leu Ala
            1605                1610                1615

Arg Leu Lys Pro Thr Leu Ala Gly Pro Thr Pro Leu Leu Tyr Arg Leu
        1620                1625                1630

Gly Pro Ile Thr Asn Glu Val Thr Leu Thr His Pro Gly Thr Lys Tyr
    1635                1640                1645

Ile Ala Thr Cys Met Gln Ala Asp Leu Glu Val Met Thr Ser Thr Trp
1650                1655                1660

Val Leu Ala Gly Gly Val Leu Ala Ala Val Ala Ala Tyr Cys Leu Ala
1665                1670                1675                1680

Thr Gly Cys Val Ser Ile Ile Gly Arg Leu His Val Asn Gln Arg Val
            1685                1690                1695
```

Val Val Ala Pro Asp Lys Glu Val Leu Tyr Glu Ala Phe Asp Glu Met
        1700                1705                1710

Glu Glu Cys Ala Ser Arg Ala Ala Leu Ile Glu Glu Gly Gln Arg Ile
        1715                1720                1725

Ala Glu Met Leu Lys Ser Lys Ile Gln Gly Leu Gln Gln Ala Ser
    1730                1735                1740

Lys Gln Ala Gln Asp Ile Gln Pro Ala Met Gln Ala Ser Trp Pro Lys
1745                1750                1755                1760

Val Glu Gln Phe Trp Ala Arg His Met Trp Asn Phe Ile Ser Gly Ile
        1765                1770                1775

Gln Tyr Leu Ala Gly Leu Ser Thr Leu Pro Gly Asn Pro Ala Val Ala
    1780                1785                1790

Ser Met Met Ala Phe Ser Ala Ala Leu Thr Ser Pro Leu Ser Thr Ser
    1795                1800                1805

Thr Thr Ile Leu Leu Asn Ile Met Gly Gly Trp Leu Ala Ser Gln Ile
    1810                1815                1820

Ala Pro Pro Ala Gly Ala Thr Gly Phe Val Val Ser Gly Leu Val Gly
1825                1830                1835                1840

Ala Ala Val Gly Ser Ile Gly Leu Gly Lys Val Leu Val Asp Ile Leu
        1845                1850                1855

Ala Gly Tyr Gly Ala Gly Ile Ser Gly Ala Leu Val Ala Phe Lys Ile
        1860                1865                1870

Met Ser Gly Glu Lys Pro Ser Met Glu Asp Val Ile Asn Leu Leu Pro
    1875                1880                1885

Gly Ile Leu Ser Pro Gly Ala Leu Val Val Gly Val Ile Cys Ala Ala
    1890                1895                1900

Ile Leu Arg Arg His Val Gly Pro Gly Glu Gly Ala Val Gln Trp Met
1905                1910                1915                1920

Asn Arg Leu Ile Ala Phe Ala Ser Arg Gly Asn His Val Ala Pro Thr
        1925                1930                1935

His Tyr Val Thr Glu Ser Asp Ala Ser Gln Arg Val Thr Gln Leu Leu
    1940                1945                1950

Gly Ser Leu Thr Ile Thr Ser Leu Leu Arg Arg Leu His Asn Trp Ile
    1955                1960                1965

Thr Glu Asp Cys Pro Ile Pro Cys Ser Gly Ser Trp Leu Arg Asp Val
    1970                1975                1980

Trp Asp Trp Val Cys Thr Ile Leu Thr Asp Phe Lys Asn Trp Leu Thr
1985                1990                1995                2000

Ser Lys Leu Phe Pro Lys Leu Pro Gly Leu Pro Phe Ile Ser Cys Gln
        2005                2010                2015

Lys Gly Tyr Lys Gly Val Trp Ala Gly Thr Gly Ile Met Thr Thr Arg
        2020                2025                2030

Cys Pro Cys Gly Ala Asn Ile Ser Gly Asn Val Arg Leu Gly Ser Met
    2035                2040                2045

Arg Ile Thr Gly Pro Lys Thr Cys Met Asn Thr Trp Gln Gly Thr Phe
2050                2055                2060

Pro Ile Asn Cys Tyr Thr Glu Gly Gln Cys Ala Pro Lys Pro Pro Thr
2065                2070                2075                2080

Asn Tyr Lys Thr Ala Ile Trp Arg Val Ala Ala Ser Glu Tyr Ala Glu
        2085                2090                2095

Val Thr Gln His Gly Ser Tyr Ser Tyr Val Thr Gly Leu Thr Thr Asp
    2100                2105                2110

Asn Leu Lys Ile Pro Cys Gln Leu Pro Ser Pro Glu Phe Phe Ser Trp

```
                2115                2120                2125
Val Asp Gly Val Gln Ile His Arg Phe Ala Pro Thr Pro Lys Pro Phe
    2130                2135                2140

Phe Arg Asp Glu Val Ser Phe Cys Val Gly Leu Asn Ser Tyr Ala Val
2145                2150                2155                2160

Gly Ser Gln Leu Pro Cys Glu Pro Glu Pro Asp Ala Asp Val Leu Arg
            2165                2170                2175

Ser Met Leu Thr Asp Pro Pro His Ile Thr Ala Glu Thr Ala Ala Arg
        2180                2185                2190

Arg Leu Ala Arg Gly Ser Pro Pro Ser Glu Ala Ser Ser Ser Val Ser
            2195                2200                2205

Gln Leu Ser Ala Pro Ser Leu Arg Ala Thr Cys Thr Thr His Ser Asn
    2210                2215                2220

Thr Tyr Asp Val Asp Met Val Asp Ala Asn Leu Leu Met Glu Gly Gly
2225                2230                2235                2240

Val Ala Gln Thr Glu Pro Glu Ser Arg Val Pro Val Leu Asp Phe Leu
            2245                2250                2255

Glu Pro Met Ala Glu Glu Glu Ser Asp Leu Glu Pro Ser Ile Pro Ser
        2260                2265                2270

Glu Cys Met Leu Pro Arg Ser Gly Phe Pro Arg Ala Leu Pro Ala Trp
            2275                2280                2285

Ala Arg Pro Asp Tyr Asn Pro Pro Leu Val Glu Ser Trp Arg Arg Pro
    2290                2295                2300

Asp Tyr Gln Pro Pro Thr Val Ala Gly Cys Ala Leu Pro Pro Pro Lys
2305                2310                2315                2320

Lys Ala Pro Thr Pro Pro Pro Arg Arg Arg Arg Thr Val Gly Leu Ser
            2325                2330                2335

Glu Ser Thr Ile Ser Glu Ala Leu Gln Gln Leu Ala Ile Lys Thr Phe
        2340                2345                2350

Gly Gln Pro Pro Ser Ser Gly Asp Ala Gly Ser Ser Thr Gly Ala Gly
            2355                2360                2365

Ala Ala Glu Ser Gly Gly Pro Thr Ser Pro Gly Glu Pro Ala Pro Ser
    2370                2375                2380

Glu Thr Gly Ser Ala Ser Ser Met Pro Pro Leu Glu Gly Glu Pro Gly
2385                2390                2395                2400

Asp Pro Asp Leu Glu Ser Asp Gln Val Glu Leu Gln Pro Pro Pro Gln
            2405                2410                2415

Gly Gly Gly Val Ala Pro Gly Ser Gly Ser Gly Ser Trp Ser Thr Cys
        2420                2425                2430

Ser Glu Glu Asp Asp Thr Thr Val Cys Cys Ser Met Ser Tyr Ser Trp
            2435                2440                2445

Thr Gly Ala Leu Ile Thr Pro Cys Ser Pro Glu Glu Glu Lys Leu Pro
    2450                2455                2460

Ile Asn Pro Leu Ser Asn Ser Leu Leu Arg Tyr His Asn Lys Val Tyr
2465                2470                2475                2480

Cys Thr Thr Ser Lys Ser Ala Ser Gln Arg Ala Lys Lys Val Thr Phe
            2485                2490                2495

Asp Arg Thr Gln Val Leu Asp Ala His Tyr Asp Ser Val Leu Lys Asp
        2500                2505                2510

Ile Lys Leu Ala Ala Ser Lys Val Ser Ala Arg Leu Leu Thr Leu Glu
            2515                2520                2525

Glu Ala Cys Gln Leu Thr Pro Pro His Ser Ala Arg Ser Lys Tyr Gly
    2530                2535                2540
```

```
Phe Gly Ala Lys Glu Val Arg Ser Leu Ser Gly Arg Ala Val Asn His
2545                2550                2555                2560

Ile Lys Ser Val Trp Lys Asp Leu Leu Glu Asp Pro Gln Thr Pro Ile
            2565                2570                2575

Pro Thr Thr Ile Met Ala Lys Asn Glu Val Phe Cys Val Asp Pro Ala
        2580                2585                2590

Lys Gly Gly Lys Lys Pro Ala Arg Leu Ile Val Tyr Pro Asp Leu Gly
    2595                2600                2605

Val Arg Val Cys Glu Lys Met Ala Leu Tyr Asp Ile Thr Gln Lys Leu
   2610                2615                2620

Pro Gln Ala Val Met Gly Ala Ser Tyr Gly Phe Gln Tyr Ser Pro Ala
2625                2630                2635                2640

Gln Arg Val Glu Tyr Leu Leu Lys Ala Trp Ala Glu Lys Lys Asp Pro
            2645                2650                2655

Met Gly Phe Ser Tyr Asp Thr Arg Cys Phe Asp Ser Thr Val Thr Glu
        2660                2665                2670

Arg Asp Ile Arg Thr Glu Glu Ser Ile Tyr Gln Ala Cys Ser Leu Pro
    2675                2680                2685

Glu Glu Ala Arg Thr Ala Ile His Ser Leu Thr Glu Arg Leu Tyr Val
   2690                2695                2700

Gly Gly Pro Met Phe Asn Ser Lys Gly Gln Thr Cys Gly Tyr Arg Arg
2705                2710                2715                2720

Cys Arg Ala Ser Gly Val Leu Thr Thr Ser Met Gly Asn Thr Ile Thr
            2725                2730                2735

Cys Tyr Val Lys Ala Leu Ala Ala Cys Lys Ala Ala Gly Ile Val Ala
        2740                2745                2750

Pro Thr Met Leu Val Cys Gly Asp Asp Leu Val Val Ile Ser Glu Ser
    2755                2760                2765

Gln Gly Thr Glu Glu Asp Glu Arg Asn Leu Arg Ala Phe Thr Glu Ala
   2770                2775                2780

Met Thr Arg Tyr Ser Ala Pro Pro Gly Asp Pro Pro Arg Pro Glu Tyr
2785                2790                2795                2800

Asp Leu Glu Leu Ile Thr Ser Cys Ser Ser Asn Val Ser Val Ala Leu
            2805                2810                2815

Gly Pro Arg Gly Arg Arg Arg Tyr Tyr Leu Thr Arg Asp Pro Thr Thr
        2820                2825                2830

Pro Leu Ala Arg Ala Ala Trp Glu Thr Val Arg His Ser Pro Ile Asn
    2835                2840                2845

Ser Trp Leu Gly Asn Ile Ile Gln Tyr Ala Pro Thr Ile Trp Val Arg
   2850                2855                2860

Met Val Leu Met Thr His Phe Phe Ser Ile Leu Met Val Gln Asp Thr
2865                2870                2875                2880

Leu Asp Gln Asn Leu Asn Phe Glu Met Tyr Gly Ser Val Tyr Ser Val
            2885                2890                2895

Asn Pro Leu Asp Leu Pro Ala Ile Ile Glu Arg Leu His Gly Leu Asp
        2900                2905                2910

Ala Phe Ser Met His Thr Tyr Ser His His Glu Leu Thr Arg Val Ala
    2915                2920                2925

Ser Ala Leu Arg Lys Leu Gly Ala Pro Pro Leu Arg Val Trp Lys Ser
   2930                2935                2940

Arg Ala Arg Ala Val Arg Ala Ser Leu Ile Ser Arg Gly Gly Lys Ala
2945                2950                2955                2960

Ala Val Cys Gly Arg Tyr Leu Phe Asn Trp Ala Val Lys Thr Lys Leu
            2965                2970                2975
```

```
Lys Leu Thr Pro Leu Pro Glu Ala Arg Leu Leu Asp Leu Ser Ser Trp
        2980                2985                2990

Phe Thr Val Gly Ala Gly Gly Gly Asp Ile Phe His Ser Val Ser Arg
        2995                3000                3005

Ala Arg Pro Arg Ser Leu Leu Phe Gly Leu Leu Leu Phe Val Gly
    3010                3015                3020

Val Gly Leu Phe Leu Leu Pro Ala Arg
3025                3030

<210> SEQ ID NO 5
<211> LENGTH: 9674
<212> TYPE: DNA
<213> ORGANISM: Hepatitis C virus
<220> FEATURE:
<221> NAME/KEY: CDS
<222> LOCATION: (341)..(9442)

<400> SEQUENCE: 5
acccgcccct aatagggcg acactccgcc atgaatcact ccctgtgag gaactactgt      60 cttcacgcag aaagcgtcta gccatggcgt tagtatgagt gtcgtacagc ctccaggccc    120 cccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
tgcttgcgag tgccccggga ggtctcgtag accgtgcacc atg agc aca aat ccc     355
                                               Met Ser Thr Asn Pro
                                                 1               5 aaa cct caa aga aaa acc aaa aga aac act aac cgt cgc cca caa gac    403
Lys Pro Gln Arg Lys Thr Lys Arg Asn Thr Asn Arg Arg Pro Gln Asp
         10                  15                  20 gtt aag ttt ccg ggc ggc ggc cag atc gtt ggc gga gta tac ttg ttg    451
Val Lys Phe Pro Gly Gly Gly Gln Ile Val Gly Gly Val Tyr Leu Leu
     25                  30                  35 ccg cgc agg ggc ccc agg ttg ggt gtg cgc gcg aca agg aag gct tcg    499
Pro Arg Arg Gly Pro Arg Leu Gly Val Arg Ala Thr Arg Lys Ala Ser
 40                  45                  50 gag cgg tcc cag cca cgt ggg agg cgc cag ccc atc ccc aaa cat cgg    547
Glu Arg Ser Gln Pro Arg Gly Arg Arg Gln Pro Ile Pro Lys His Arg
 55                  60                  65 cgc tcc act ggc aag tcc tgg ggg aag cca gga tac ccc tgg ccc ctg    595
Arg Ser Thr Gly Lys Ser Trp Gly Lys Pro Gly Tyr Pro Trp Pro Leu
 70                  75                  80                  85 tat ggg aat gag ggg ctc ggt tgg gca gga tgg ctc ctg tcc cct cga    643
Tyr Gly Asn Glu Gly Leu Gly Trp Ala Gly Trp Leu Leu Ser Pro Arg
             90                  95                 100 ggt tcc cgt ccc tca tgg ggc ccc aat gac ccc cgg cat agg tcg cgc    691
Gly Ser Arg Pro Ser Trp Gly Pro Asn Asp Pro Arg His Arg Ser Arg
        105                 110                 115 aat gtg ggt aag gtc atc gat acc cta acg tgc ggc ttt gcc gac ctc    739
Asn Val Gly Lys Val Ile Asp Thr Leu Thr Cys Gly Phe Ala Asp Leu
    120                 125                 130 ttg ggg tac gtc ccc gtc gta ggc gcc ccg ctt agt ggc gtt gcc agt    787
Leu Gly Tyr Val Pro Val Val Gly Ala Pro Leu Ser Gly Val Ala Ser
135                 140                 145 gct ctc gcg cac ggc gtg aga gtc ctg gag gac ggg gtt aat ttt gca    835
Ala Leu Ala His Gly Val Arg Val Leu Glu Asp Gly Val Asn Phe Ala
150                 155                 160                 165 aca ggg aac tta cct ggt tgc tcc ttt tct atc ttc ttg ctg gcc cta    883
Thr Gly Asn Leu Pro Gly Cys Ser Phe Ser Ile Phe Leu Leu Ala Leu
```

-continued

```
                    170                 175                 180
ctg tcc tgc atc act act ccg gtc tct gct gtc caa gtg aag aac acc       931
Leu Ser Cys Ile Thr Thr Pro Val Ser Ala Val Gln Val Lys Asn Thr
            185                 190                 195 agc aac gcc tat atg gcg act aac gac tgt tcc aat gac agc atc act       979
Ser Asn Ala Tyr Met Ala Thr Asn Asp Cys Ser Asn Asp Ser Ile Thr
                200                 205                 210 tgg cag ctt gag gcc gca gtc ctc cat gtc ccc ggg tgc gtc ccg tgc      1027
Trp Gln Leu Glu Ala Ala Val Leu His Val Pro Gly Cys Val Pro Cys
    215                 220                 225 gag aaa atg ggg aac aca tca cgg tgc tgg ata cca gtc tca cca aac      1075
Glu Lys Met Gly Asn Thr Ser Arg Cys Trp Ile Pro Val Ser Pro Asn
230                 235                 240                 245 gtg gct gtg cgg cag cct ggc gcc ctc acg cgg ggc ttg cgg acg cac      1123
Val Ala Val Arg Gln Pro Gly Ala Leu Thr Arg Gly Leu Arg Thr His
                250                 255                 260 atc gac atg gtc gtg ttg tcc gcc acg ctc tgc tcc gct ctc tac gtg      1171
Ile Asp Met Val Val Leu Ser Ala Thr Leu Cys Ser Ala Leu Tyr Val
                265                 270                 275 ggg gac ctc tgt ggc ggg gtg atg ctc gcg tcc cag atg ttc att gtc      1219
Gly Asp Leu Cys Gly Gly Val Met Leu Ala Ser Gln Met Phe Ile Val
            280                 285                 290 tcg ccg cag cac cac tgg ttc gtg cag gaa tgc aat tgc tcc atc tac      1267
Ser Pro Gln His His Trp Phe Val Gln Glu Cys Asn Cys Ser Ile Tyr
    295                 300                 305 cct ggc gcc atc act ggg cac cgt atg gca tgg gac atg atg atg aac      1315
Pro Gly Ala Ile Thr Gly His Arg Met Ala Trp Asp Met Met Met Asn
310                 315                 320                 325 tgg tcg ccc acg acc acc atg atc ctg gcg tac gtg atg cgc gtt ccc      1363
Trp Ser Pro Thr Thr Thr Met Ile Leu Ala Tyr Val Met Arg Val Pro
                330                 335                 340 gag gtc atc ata gac atc att agc gga gct cac tgg ggc gtc atg ttt      1411
Glu Val Ile Ile Asp Ile Ile Ser Gly Ala His Trp Gly Val Met Phe
                345                 350                 355 ggc ctg gcc tac ttc tct atg cag gga gcg tgg gcg aag gtc gtt gtc      1459
Gly Leu Ala Tyr Phe Ser Met Gln Gly Ala Trp Ala Lys Val Val Val
            360                 365                 370 atc ctc ctg ctg gcc tct ggg gtg gac gcg tac acc acg acg act ggg      1507
Ile Leu Leu Leu Ala Ser Gly Val Asp Ala Tyr Thr Thr Thr Thr Gly
    375                 380                 385 agc gct gct ggg cgc act acc agt agc ctg gcc agc gcc ttc tcc cct      1555
Ser Ala Ala Gly Arg Thr Thr Ser Ser Leu Ala Ser Ala Phe Ser Pro
390                 395                 400                 405 ggc gct cgg cag aac att cag ctc att aat acc aat ggt agc tgg cac      1603
Gly Ala Arg Gln Asn Ile Gln Leu Ile Asn Thr Asn Gly Ser Trp His
                410                 415                 420 atc aac cgc acc gcc ctg aat tgc aac gat tcc ttg cac acc ggc ttc      1651
Ile Asn Arg Thr Ala Leu Asn Cys Asn Asp Ser Leu His Thr Gly Phe
                425                 430                 435 ttc acg gcc ctg ttc tac atc cat aag ttc aac tcg tcg gga tgt ccc      1699
Phe Thr Ala Leu Phe Tyr Ile His Lys Phe Asn Ser Ser Gly Cys Pro
            440                 445                 450 gag cgc ctg tcc gcc tgt cgc aac atc gag gac ttc cgg ata gga tgg      1747
Glu Arg Leu Ser Ala Cys Arg Asn Ile Glu Asp Phe Arg Ile Gly Trp
    455                 460                 465 ggc gcc ctg caa tac gac gac aat gtc acc aat cca gaa gat atg agg      1795
Gly Ala Leu Gln Tyr Asp Asp Asn Val Thr Asn Pro Glu Asp Met Arg
470                 475                 480                 485 cca tat tgc tgg cac tac cca cca aaa cag tgt ggc gta gtc ccc gca      1843
Pro Tyr Cys Trp His Tyr Pro Pro Lys Gln Cys Gly Val Val Pro Ala
```

-continued

| | | | | | | | | | | | | | | | |
|---|---|---|---|---|---|---|---|---|---|---|---|---|---|---|---|
| | | | | 490 | | | | | 495 | | | | | 500 | |
| ggg | acc | gtg | tgc | ggc | cca | gtg | tac | tgt | ttc | acc | cct | agc | ccg | gtg | gta | 1891 |
| Gly | Thr | Val | Cys | Gly | Pro | Val | Tyr | Cys | Phe | Thr | Pro | Ser | Pro | Val | Val | |
| | | | 505 | | | | | 510 | | | | | 515 | | | |
| gtg | ggc | acg | acc | gat | aga | ctt | gga | gtg | cct | act | tac | acg | tgg | gga | gag | 1939 |
| Val | Gly | Thr | Thr | Asp | Arg | Leu | Gly | Val | Pro | Thr | Tyr | Thr | Trp | Gly | Glu | |
| | | 520 | | | | | 525 | | | | | 530 | | | | |
| aat | gag | aca | gat | gtc | ttc | cta | ttg | aac | agc | acc | cga | cca | ccg | tcg | ggg | 1987 |
| Asn | Glu | Thr | Asp | Val | Phe | Leu | Leu | Asn | Ser | Thr | Arg | Pro | Pro | Ser | Gly | |
| 535 | | | | | 540 | | | | | 545 | | | | | | |
| tca | tgg | ttt | ggc | tgc | acg | tgg | atg | aac | tcc | act | ggc | ttc | acc | aag | acc | 2035 |
| Ser | Trp | Phe | Gly | Cys | Thr | Trp | Met | Asn | Ser | Thr | Gly | Phe | Thr | Lys | Thr | |
| 550 | | | | | 555 | | | | | 560 | | | | | 565 | |
| tgc | ggc | gca | cca | ccc | tgc | cgc | act | aga | gct | gac | ttc | aat | acc | agc | aca | 2083 |
| Cys | Gly | Ala | Pro | Pro | Cys | Arg | Thr | Arg | Ala | Asp | Phe | Asn | Thr | Ser | Thr | |
| | | | 570 | | | | | 575 | | | | | 580 | | | |
| gat | ctg | ttg | tgc | ccc | acg | gac | tgt | ttt | aga | aaa | cat | cct | gaa | gcc | act | 2131 |
| Asp | Leu | Leu | Cys | Pro | Thr | Asp | Cys | Phe | Arg | Lys | His | Pro | Glu | Ala | Thr | |
| | | 585 | | | | | 590 | | | | | 595 | | | | |
| tac | atc | aaa | tgt | ggt | tcc | ggg | cct | tgg | ctc | acg | cca | aag | tgt | ctg | gtt | 2179 |
| Tyr | Ile | Lys | Cys | Gly | Ser | Gly | Pro | Trp | Leu | Thr | Pro | Lys | Cys | Leu | Val | |
| | | 600 | | | | | 605 | | | | | 610 | | | | |
| gac | tac | ccc | tac | agg | ctc | tgg | cat | tac | cct | tgc | aca | gtc | aat | tac | tcc | 2227 |
| Asp | Tyr | Pro | Tyr | Arg | Leu | Trp | His | Tyr | Pro | Cys | Thr | Val | Asn | Tyr | Ser | |
| 615 | | | | | 620 | | | | | 625 | | | | | | |
| acc | ttc | aag | atc | agg | atg | tat | gtg | ggg | gga | gtt | gag | cac | agg | ctc | atg | 2275 |
| Thr | Phe | Lys | Ile | Arg | Met | Tyr | Val | Gly | Gly | Val | Glu | His | Arg | Leu | Met | |
| 630 | | | | | 635 | | | | | 640 | | | | | 645 | |
| gcc | gcg | tgc | aat | ttc | act | cgt | ggg | gat | cgc | tgc | aac | ttg | gag | gat | agg | 2323 |
| Ala | Ala | Cys | Asn | Phe | Thr | Arg | Gly | Asp | Arg | Cys | Asn | Leu | Glu | Asp | Arg | |
| | | | | 650 | | | | | 655 | | | | | 660 | | |
| gac | aga | agt | caa | cag | act | cct | ctg | ttg | cac | tcc | acc | acg | gaa | tgg | gcc | 2371 |
| Asp | Arg | Ser | Gln | Gln | Thr | Pro | Leu | Leu | His | Ser | Thr | Thr | Glu | Trp | Ala | |
| | | | 665 | | | | | 670 | | | | | 675 | | | |
| att | ttg | ccc | tgc | tct | ttc | tca | gac | ttg | ccc | gct | ttg | tcg | act | ggt | ctt | 2419 |
| Ile | Leu | Pro | Cys | Ser | Phe | Ser | Asp | Leu | Pro | Ala | Leu | Ser | Thr | Gly | Leu | |
| | | 680 | | | | | 685 | | | | | 690 | | | | |
| ctc | cac | ctc | cac | caa | aat | atc | gtg | gac | gta | caa | tat | atg | tat | ggc | ctg | 2467 |
| Leu | His | Leu | His | Gln | Asn | Ile | Val | Asp | Val | Gln | Tyr | Met | Tyr | Gly | Leu | |
| | 695 | | | | | 700 | | | | | 705 | | | | | |
| tca | cct | gcc | ctc | aca | caa | tat | atc | gtt | cga | tgg | gag | tgg | gta | gta | ctc | 2515 |
| Ser | Pro | Ala | Leu | Thr | Gln | Tyr | Ile | Val | Arg | Trp | Glu | Trp | Val | Val | Leu | |
| 710 | | | | | 715 | | | | | 720 | | | | | 725 | |
| tta | ttc | ctg | ctc | cta | gcg | gac | gcc | agg | gtc | tgc | gcc | tgc | ttg | tgg | atg | 2563 |
| Leu | Phe | Leu | Leu | Leu | Ala | Asp | Ala | Arg | Val | Cys | Ala | Cys | Leu | Trp | Met | |
| | | | 730 | | | | | 735 | | | | | 740 | | | |
| ctc | atc | ttg | ctg | ggc | caa | gcc | gaa | gca | gca | ctg | gag | aag | ctg | gtc | gtc | 2611 |
| Leu | Ile | Leu | Leu | Gly | Gln | Ala | Glu | Ala | Ala | Leu | Glu | Lys | Leu | Val | Val | |
| | | | 745 | | | | | 750 | | | | | 755 | | | |
| ttg | cac | gct | gcg | agc | gca | gct | agc | tgc | aat | ggc | ttc | ctg | tat | ttt | gtc | 2659 |
| Leu | His | Ala | Ala | Ser | Ala | Ala | Ser | Cys | Asn | Gly | Phe | Leu | Tyr | Phe | Val | |
| | | | 760 | | | | | 765 | | | | | 770 | | | |
| atc | ttt | ctc | gtg | gct | gct | tgg | cac | atc | aag | ggt | agg | gtg | gtc | ccc | ttg | 2707 |
| Ile | Phe | Leu | Val | Ala | Ala | Trp | His | Ile | Lys | Gly | Arg | Val | Val | Pro | Leu | |
| 775 | | | | | 780 | | | | | 785 | | | | | | |
| gct | gct | tat | tcc | ctt | act | ggc | ctg | tgg | ccg | ttc | tgc | cta | ctg | ctc | cta | 2755 |
| Ala | Ala | Tyr | Ser | Leu | Thr | Gly | Leu | Trp | Pro | Phe | Cys | Leu | Leu | Leu | Leu | |
| 790 | | | | | 795 | | | | | 800 | | | | | 805 | |
| gca | ctg | ccc | cag | cag | gct | tac | gcc | tat | gat | gca | tct | gtg | cac | gga | cag | 2803 |
| Ala | Leu | Pro | Gln | Gln | Ala | Tyr | Ala | Tyr | Asp | Ala | Ser | Val | His | Gly | Gln | |

```
                      810                 815                 820
gtg ggc gcg gct ttg cta gta ctg att acc ctc ttt aca ctc acc ccg      2851
Val Gly Ala Ala Leu Leu Val Leu Ile Thr Leu Phe Thr Leu Thr Pro
                825                 830                 835 ggg tat aag acc ctt ctc agc cag tcc ctg tgg tgg ttg tgc tat ctc      2899
Gly Tyr Lys Thr Leu Leu Ser Gln Ser Leu Trp Trp Leu Cys Tyr Leu
                840                 845                 850 ctg acc ctg gcg gaa acc atg gtc cag gag tgg gca cca tcc atg cag      2947
Leu Thr Leu Ala Glu Thr Met Val Gln Glu Trp Ala Pro Ser Met Gln
            855                 860                 865 gcg cgc ggc ggc cgt gat ggc atc ata tgg gcc gcc acc ata ttt tgc      2995
Ala Arg Gly Gly Arg Asp Gly Ile Ile Trp Ala Ala Thr Ile Phe Cys
870                 875                 880                 885 ccg ggc gta gtg ttt gac ata acc aag tgg ctc tta gcg gtg ctt ggg      3043
Pro Gly Val Val Phe Asp Ile Thr Lys Trp Leu Leu Ala Val Leu Gly
                    890                 895                 900 cct ggt tac ctc cta aga ggt gct ttg acg cgc gtg cca tat ttc gtc      3091
Pro Gly Tyr Leu Leu Arg Gly Ala Leu Thr Arg Val Pro Tyr Phe Val
                905                 910                 915 aga gcc cac gct ctg ctg aga atg tgc act atg gtg agg cac ctc gcg      3139
Arg Ala His Ala Leu Leu Arg Met Cys Thr Met Val Arg His Leu Ala
            920                 925                 930 ggg ggt agg tac gtc cag atg gcg cta tta gcc ctt ggc agg tgg act      3187
Gly Gly Arg Tyr Val Gln Met Ala Leu Leu Ala Leu Gly Arg Trp Thr
        935                 940                 945 ggc act tac atc tat gac cac ctc acc cct atg tcg gat tgg gct gct      3235
Gly Thr Tyr Ile Tyr Asp His Leu Thr Pro Met Ser Asp Trp Ala Ala
950                 955                 960                 965 agc ggc ctg cgg gac ttg gcg gtc gct gtg gag cct atc atc ttc agt      3283
Ser Gly Leu Arg Asp Leu Ala Val Ala Val Glu Pro Ile Ile Phe Ser
                970                 975                 980 ccg atg gag aag aaa gtc atc gtt tgg gga gcg gag acg gct gcg tgc      3331
Pro Met Glu Lys Lys Val Ile Val Trp Gly Ala Glu Thr Ala Ala Cys
            985                 990                 995 ggg gac atc ttg cac gga ctt ccc gtg tcc gcc cga ctc ggt cgg gag      3379
Gly Asp Ile Leu His Gly Leu Pro Val Ser Ala Arg Leu Gly Arg Glu
        1000                1005                1010 atc ctc ctt ggc cca gct gat ggc tac acc tcc aag ggg tgg aag ctt      3427
Ile Leu Leu Gly Pro Ala Asp Gly Tyr Thr Ser Lys Gly Trp Lys Leu
    1015                1020                1025 ctc gcc ccc atc acc gct tac gcc cag cag aca cga ggt ctc ttg ggc      3475
Leu Ala Pro Ile Thr Ala Tyr Ala Gln Gln Thr Arg Gly Leu Leu Gly
1030                1035                1040                1045 tct ata gtg gtg agc atg acg ggg cgt gac aag aca gaa cag gcc ggg      3523
Ser Ile Val Val Ser Met Thr Gly Arg Asp Lys Thr Glu Gln Ala Gly
                1050                1055                1060 gag gtc caa gtc ctg tcc aca gtc act cag tcc ttc ctc gga aca tcc      3571
Glu Val Gln Val Leu Ser Thr Val Thr Gln Ser Phe Leu Gly Thr Ser
            1065                1070                1075 att tcg ggg gtc tta tgg act gtt tac cac gga gct ggc aac aag aca      3619
Ile Ser Gly Val Leu Trp Thr Val Tyr His Gly Ala Gly Asn Lys Thr
        1080                1085                1090 cta gcc ggc tcg cgg ggc ccg gtc acg cag atg tac tcg agc gcc gag      3667
Leu Ala Gly Ser Arg Gly Pro Val Thr Gln Met Tyr Ser Ser Ala Glu
    1095                1100                1105 ggg gac ttg gtc ggg tgg ccc agc cct cct ggg acc aaa tct ttg gag      3715
Gly Asp Leu Val Gly Trp Pro Ser Pro Pro Gly Thr Lys Ser Leu Glu
1110                1115                1120                1125 ccg tgt acg tgt gga gcg gtc gac ctg tat ttg gtc acg cgg aac gct      3763
Pro Cys Thr Cys Gly Ala Val Asp Leu Tyr Leu Val Thr Arg Asn Ala
```

```
                1130            1135            1140
gat gtc atc ccg gct cga aga cgc ggg gac aag cgg gga gcg ctg ctc    3811
Asp Val Ile Pro Ala Arg Arg Arg Gly Asp Lys Arg Gly Ala Leu Leu
        1145            1150            1155 tcc ccg aga ccc ctt tcg acc ttg aag ggg tcc tcg ggg gga cct gtg    3859
Ser Pro Arg Pro Leu Ser Thr Leu Lys Gly Ser Ser Gly Gly Pro Val
    1160            1165            1170 ctt tgc cct agg ggc cac gct gtc gga atc ttc cgg gca gct gtg tgc    3907
Leu Cys Pro Arg Gly His Ala Val Gly Ile Phe Arg Ala Ala Val Cys
    1175            1180            1185 tct cgg ggt gtg gct aag tcc ata gat ttc atc ccc gtt gag acg ctc    3955
Ser Arg Gly Val Ala Lys Ser Ile Asp Phe Ile Pro Val Glu Thr Leu
1190            1195            1200            1205 gac atc gtc acg cgg tct ccc acc ttt agt gac aac agc aca cca cca    4003
Asp Ile Val Thr Arg Ser Pro Thr Phe Ser Asp Asn Ser Thr Pro Pro
        1210            1215            1220 gct gtg ccc cag acc tat cag gtg ggg tac ttg cac gcc ccc act ggc    4051
Ala Val Pro Gln Thr Tyr Gln Val Gly Tyr Leu His Ala Pro Thr Gly
    1225            1230            1235 agt gga aaa agc acc aag gtc ccc gtc gcg tac gcc gcc cag ggg tat    4099
Ser Gly Lys Ser Thr Lys Val Pro Val Ala Tyr Ala Ala Gln Gly Tyr
    1240            1245            1250 aaa gtg ctg gtg ctc aat ccc tcg gtg gct gcc acc ctg gga ttt ggg    4147
Lys Val Leu Val Leu Asn Pro Ser Val Ala Ala Thr Leu Gly Phe Gly
    1255            1260            1265 gcg tac ttg tcc aag gca cat ggc atc aac ccc aac att agg act gga    4195
Ala Tyr Leu Ser Lys Ala His Gly Ile Asn Pro Asn Ile Arg Thr Gly
1270            1275            1280            1285 gtc aga act gtg acg acc ggg gag ccc att aca tac tcc acg tat ggt    4243
Val Arg Thr Val Thr Thr Gly Glu Pro Ile Thr Tyr Ser Thr Tyr Gly
        1290            1295            1300 aaa ttc ctc gcc gat ggg ggc tgc gca ggc ggc gcc tat gac atc atc    4291
Lys Phe Leu Ala Asp Gly Gly Cys Ala Gly Gly Ala Tyr Asp Ile Ile
    1305            1310            1315 ata tgc gat gaa tgc cac tct gtg gat gct acc act att ctc ggc atc    4339
Ile Cys Asp Glu Cys His Ser Val Asp Ala Thr Thr Ile Leu Gly Ile
    1320            1325            1330 ggg aca gtc ctt gac caa gca gag aca gcc ggg gtc agg cta act gta    4387
Gly Thr Val Leu Asp Gln Ala Glu Thr Ala Gly Val Arg Leu Thr Val
    1335            1340            1345 ctg gcc acg gcc acg ccc ccc ggg tcg gtg aca acc ccc cat ccc aat    4435
Leu Ala Thr Ala Thr Pro Pro Gly Ser Val Thr Thr Pro His Pro Asn
1350            1355            1360            1365 ata gag gag gta gcc ctc gga cag gag ggt gag atc ccc ttc tat ggg    4483
Ile Glu Glu Val Ala Leu Gly Gln Glu Gly Glu Ile Pro Phe Tyr Gly
        1370            1375            1380 agg gcg ttt ccc ctg tct tac atc aag gga ggg agg cac ttg att ttc    4531
Arg Ala Phe Pro Leu Ser Tyr Ile Lys Gly Gly Arg His Leu Ile Phe
    1385            1390            1395 tgc cac tca aag aaa aag tgt gac gag ctc gca acg gcc ctt cgg ggc    4579
Cys His Ser Lys Lys Lys Cys Asp Glu Leu Ala Thr Ala Leu Arg Gly
    1400            1405            1410 atg ggc ttg aac gct gtg gca tat tac aga ggg ttg gac gtc tcc ata    4627
Met Gly Leu Asn Ala Val Ala Tyr Tyr Arg Gly Leu Asp Val Ser Ile
    1415            1420            1425 ata cca act caa gga gat gtg gtg gtc gtt gcc acc gac gcc ctc atg    4675
Ile Pro Thr Gln Gly Asp Val Val Val Val Ala Thr Asp Ala Leu Met
1430            1435            1440            1445 acg ggg tat act gga gac ttt gac tcc gtg atc gac tgc aac gta gcg    4723
Thr Gly Tyr Thr Gly Asp Phe Asp Ser Val Ile Asp Cys Asn Val Ala
```

```
                1450                1455                1460
gtc acc cag gcc gta gac ttc agc ctg gac ccc acc ttc act ata acc        4771
Val Thr Gln Ala Val Asp Phe Ser Leu Asp Pro Thr Phe Thr Ile Thr
            1465                1470                1475 aca cag act gtc ccg caa gac gct gtc tca cgt agt cag cgc cga ggg        4819
Thr Gln Thr Val Pro Gln Asp Ala Val Ser Arg Ser Gln Arg Arg Gly
            1480                1485                1490 cgc acg ggt aga gga aga ctg ggc att tat agg tat gtt tcc act ggt        4867
Arg Thr Gly Arg Gly Arg Leu Gly Ile Tyr Arg Tyr Val Ser Thr Gly
        1495                1500                1505 gag cga gcc tca gga atg ttt gac agt gta gta ctc tgt gag tgc tac        4915
Glu Arg Ala Ser Gly Met Phe Asp Ser Val Val Leu Cys Glu Cys Tyr
1510                1515                1520                1525 gac gca gga gct gct tgg tat gag ctc tca cca gtg gag acg acc gtc        4963
Asp Ala Gly Ala Ala Trp Tyr Glu Leu Ser Pro Val Glu Thr Thr Val
            1530                1535                1540 agg ctc agg gcg tat ttc aac acg cct ggc ttg cct gtg tgc cag gac        5011
Arg Leu Arg Ala Tyr Phe Asn Thr Pro Gly Leu Pro Val Cys Gln Asp
        1545                1550                1555 cac ctt gag ttt tgg gag gca gtt ttc acc ggc ctc aca cac ata gac        5059
His Leu Glu Phe Trp Glu Ala Val Phe Thr Gly Leu Thr His Ile Asp
    1560                1565                1570 gct cat ttc ctt tcc cag aca aag cag tcg ggg gaa aat ttc gca tac        5107
Ala His Phe Leu Ser Gln Thr Lys Gln Ser Gly Glu Asn Phe Ala Tyr
1575                1580                1585 tta gta gcc tat cag gcc aca gtg tgc gcc agg gcc aaa gcg ccc ccc        5155
Leu Val Ala Tyr Gln Ala Thr Val Cys Ala Arg Ala Lys Ala Pro Pro
1590                1595                1600                1605 ccg tcc tgg gac gtc atg tgg aag tgc ttg act cga ctc aag ccc acg        5203
Pro Ser Trp Asp Val Met Trp Lys Cys Leu Thr Arg Leu Lys Pro Thr
            1610                1615                1620 ctt gtg ggc cct aca cct ctc ctg tac cgt ttg ggc tct gtt acc aac        5251
Leu Val Gly Pro Thr Pro Leu Leu Tyr Arg Leu Gly Ser Val Thr Asn
        1625                1630                1635 gag gtc acc ctt aca cac ccc gtg aca aaa tac atc gcc aca tgc atg        5299
Glu Val Thr Leu Thr His Pro Val Thr Lys Tyr Ile Ala Thr Cys Met
    1640                1645                1650 caa gct gac ctc gag gtc atg acc agc acg tgg gtc ctg gct ggg gga        5347
Gln Ala Asp Leu Glu Val Met Thr Ser Thr Trp Val Leu Ala Gly Gly
1655                1660                1665 gtc tta gca gcc gtc gcc gcg tat tgc tta gcg acc ggg tgt gtt tcc        5395
Val Leu Ala Ala Val Ala Ala Tyr Cys Leu Ala Thr Gly Cys Val Ser
1670                1675                1680                1685 atc att ggc cgt tta cac atc aac cag cga gct gtc gtc gct ccg gac        5443
Ile Ile Gly Arg Leu His Ile Asn Gln Arg Ala Val Val Ala Pro Asp
            1690                1695                1700 aag gag gtc ctc tat gag gct ttt gat gag atg gag gaa tgt gcc tcc        5491
Lys Glu Val Leu Tyr Glu Ala Phe Asp Glu Met Glu Glu Cys Ala Ser
        1705                1710                1715 aga gcg gct ctc ctt gaa gag ggg cag cgg ata gcc gag atg ctg aag        5539
Arg Ala Ala Leu Leu Glu Glu Gly Gln Arg Ile Ala Glu Met Leu Lys
    1720                1725                1730 tcc aag atc caa ggc tta ttg cag caa gcc tct aaa cag gcc cag gac        5587
Ser Lys Ile Gln Gly Leu Leu Gln Gln Ala Ser Lys Gln Ala Gln Asp
1735                1740                1745 ata caa ccc gct gtg caa gct tcg tgg ccc aag atg gag caa ttc tgg        5635
Ile Gln Pro Ala Val Gln Ala Ser Trp Pro Lys Met Glu Gln Phe Trp
1750                1755                1760                1765 gcc aaa cat atg tgg aac ttc ata agc ggc att cag tac ctc gca gga        5683
Ala Lys His Met Trp Asn Phe Ile Ser Gly Ile Gln Tyr Leu Ala Gly
```

-continued

```
                  1770              1775              1780
ctg tca aca ctg cca ggg aac cct gct gtg gct tcc atg atg gca ttc    5731
Leu Ser Thr Leu Pro Gly Asn Pro Ala Val Ala Ser Met Met Ala Phe
        1785              1790              1795 agc gcc gcc ctc acc agt ccg ttg tca act agc acc acc atc ctt ctt    5779
Ser Ala Ala Leu Thr Ser Pro Leu Ser Thr Ser Thr Thr Ile Leu Leu
    1800              1805              1810 aac att ctg ggg ggc tgg ctg gcg tcc caa att gcg cca ccc gcg ggg    5827
Asn Ile Leu Gly Gly Trp Leu Ala Ser Gln Ile Ala Pro Pro Ala Gly
    1815              1820              1825 gcc act ggc ttt gtt gtc agt ggc ctg gtg gga gct gct gtt ggc agc    5875
Ala Thr Gly Phe Val Val Ser Gly Leu Val Gly Ala Ala Val Gly Ser
1830              1835              1840              1845 ata ggc ttg ggt aaa gtg ctg gtg gac atc ctg gca ggg tat ggt gcg    5923
Ile Gly Leu Gly Lys Val Leu Val Asp Ile Leu Ala Gly Tyr Gly Ala
        1850              1855              1860 ggc att tcg ggg gcc ctc gtc gcg ttt aag atc atg tct ggc gag aag    5971
Gly Ile Ser Gly Ala Leu Val Ala Phe Lys Ile Met Ser Gly Glu Lys
    1865              1870              1875 ccc tcc atg gag gat gtc atc aac ttg ctg cct ggg att ctg tct cca    6019
Pro Ser Met Glu Asp Val Ile Asn Leu Leu Pro Gly Ile Leu Ser Pro
    1880              1885              1890 ggt gct ctg gtg gtg gga gtc atc tgc gcg gcc att ctg cgc cgc cat    6067
Gly Ala Leu Val Val Gly Val Ile Cys Ala Ala Ile Leu Arg Arg His
    1895              1900              1905 gtg gga ccg ggg gaa ggc gcg gtc caa tgg atg aac agg ctt atc gcc    6115
Val Gly Pro Gly Glu Gly Ala Val Gln Trp Met Asn Arg Leu Ile Ala
1910              1915              1920              1925 ttc gct tcc aga gga aac cac gtc gcc cct act cac tac gtg acg gag    6163
Phe Ala Ser Arg Gly Asn His Val Ala Pro Thr His Tyr Val Thr Glu
        1930              1935              1940 tcg gat gcg tcg cag cgt gtc acc caa ctg ctt ggc tct ctc act ata    6211
Ser Asp Ala Ser Gln Arg Val Thr Gln Leu Leu Gly Ser Leu Thr Ile
    1945              1950              1955 act agt cta ctc agg aga ctt cac aac tgg atc act gag gat tgc ccc    6259
Thr Ser Leu Leu Arg Arg Leu His Asn Trp Ile Thr Glu Asp Cys Pro
    1960              1965              1970 atc cca tgc gcc ggc tcg tgg ctc cgc gat gtg tgg gac tgg gtc tgt    6307
Ile Pro Cys Ala Gly Ser Trp Leu Arg Asp Val Trp Asp Trp Val Cys
    1975              1980              1985 acc atc cta aca gac ttt aag aac tgg ctg acc tcc aag ctg ttc cca    6355
Thr Ile Leu Thr Asp Phe Lys Asn Trp Leu Thr Ser Lys Leu Phe Pro
1990              1995              2000              2005 aag atg cct ggc ctc ccc ttt atc tct tgc caa aag ggg tac aag ggc    6403
Lys Met Pro Gly Leu Pro Phe Ile Ser Cys Gln Lys Gly Tyr Lys Gly
        2010              2015              2020 gtg tgg gcc ggc act ggc atc atg acc aca cga tgc ccc tgc ggc gcc    6451
Val Trp Ala Gly Thr Gly Ile Met Thr Thr Arg Cys Pro Cys Gly Ala
    2025              2030              2035 aac atc tct ggc aac gtc cgc ttg ggc tct atg aga atc aca gga ccc    6499
Asn Ile Ser Gly Asn Val Arg Leu Gly Ser Met Arg Ile Thr Gly Pro
    2040              2045              2050 aaa acc tgc atg aac acc tgg cag ggg acc ttt cct atc aat tgt tat    6547
Lys Thr Cys Met Asn Thr Trp Gln Gly Thr Phe Pro Ile Asn Cys Tyr
    2055              2060              2065 aca gaa ggc cag tgc ttg ccg aaa ccc gcg tta aac ttc aag acc gcc    6595
Thr Glu Gly Gln Cys Leu Pro Lys Pro Ala Leu Asn Phe Lys Thr Ala
2070              2075              2080              2085 atc tgg aga gtg gcg gcc tca gag tac gcg gaa gtg acg cag cac gga    6643
Ile Trp Arg Val Ala Ala Ser Glu Tyr Ala Glu Val Thr Gln His Gly
```

```
                2090              2095              2100
tca tat gcc tat ata aca ggg ctg acc act gac aac tta aaa gtc cct    6691
Ser Tyr Ala Tyr Ile Thr Gly Leu Thr Thr Asp Asn Leu Lys Val Pro
        2105              2110              2115 tgc caa ctc ccc tct cca gag ttt ttc tct tgg gtg gac gga gta caa    6739
Cys Gln Leu Pro Ser Pro Glu Phe Phe Ser Trp Val Asp Gly Val Gln
    2120              2125              2130 atc cat agg tcc gcc ccc aca cca aag ccg ttt ttc cgg gat gag gtc    6787
Ile His Arg Ser Ala Pro Thr Pro Lys Pro Phe Phe Arg Asp Glu Val
2135              2140              2145 tcg ttc agc gtt ggg ctc aat tca ttt gtc gtc ggg tct cag ctt ccc    6835
Ser Phe Ser Val Gly Leu Asn Ser Phe Val Val Gly Ser Gln Leu Pro
2150              2155              2160              2165 tgt gac cct gag ccc gac act gag gta gtg atg tcc atg cta aca gac    6883
Cys Asp Pro Glu Pro Asp Thr Glu Val Val Met Ser Met Leu Thr Asp
            2170              2175              2180 cca tcc cat atc acg gcg gag gct gca gcg cgg cgt tta gcg cgg ggg    6931
Pro Ser His Ile Thr Ala Glu Ala Ala Ala Arg Arg Leu Ala Arg Gly
    2185              2190              2195 tca ccc cca tct gag gca agc tcc tca gcg agc cag ctg tcg gcg cca    6979
Ser Pro Pro Ser Glu Ala Ser Ser Ala Ser Gln Leu Ser Ala Pro
2200              2205              2210 tcg ctg cga gcc acc tgc acc acc cac ggt agg acc tat gat gtg gac    7027
Ser Leu Arg Ala Thr Cys Thr Thr His Gly Arg Thr Tyr Asp Val Asp
    2215              2220              2225 atg gtg gat gcc aac ctg ttc atg ggg ggc ggc gtg att cgg ata gag    7075
Met Val Asp Ala Asn Leu Phe Met Gly Gly Gly Val Ile Arg Ile Glu
2230              2235              2240              2245 tct gag tcc aaa gtg gtc gtt ctg gac tcc ctc gac tca atg acc gag    7123
Ser Glu Ser Lys Val Val Val Leu Asp Ser Leu Asp Ser Met Thr Glu
        2250              2255              2260 gaa gag ggc gac ctt gag cct tca gta cca tcg gag tat atg ctc ccc    7171
Glu Glu Gly Asp Leu Glu Pro Ser Val Pro Ser Glu Tyr Met Leu Pro
    2265              2270              2275 agg aag agg ttc cca ccg gcc tta ccg gct tgg gcg cgg cct gat tac    7219
Arg Lys Arg Phe Pro Pro Ala Leu Pro Ala Trp Ala Arg Pro Asp Tyr
2280              2285              2290 aac cca ccg ctt gtg gaa tcg tgg aag agg cca gat tac caa cca ccc    7267
Asn Pro Pro Leu Val Glu Ser Trp Lys Arg Pro Asp Tyr Gln Pro Pro
    2295              2300              2305 act gtt gcg ggc tgt gct ctc ccc ccc ccc aaa aag acc ccg acg cct    7315
Thr Val Ala Gly Cys Ala Leu Pro Pro Pro Lys Lys Thr Pro Thr Pro
2310              2315              2320              2325 cct cca agg aga cgc cgg aca gtg ggt ctg agc gag agc acc ata gga    7363
Pro Pro Arg Arg Arg Arg Thr Val Gly Leu Ser Glu Ser Thr Ile Gly
        2330              2335              2340 gat gcc ctc caa cag ctg gcc atc aag tcc ttt ggc cag ccc ccc cca    7411
Asp Ala Leu Gln Gln Leu Ala Ile Lys Ser Phe Gly Gln Pro Pro Pro
    2345              2350              2355 agc ggc gat tca ggc ctt tcc acg ggg gcg gac gcc gcc gac tcc ggc    7459
Ser Gly Asp Ser Gly Leu Ser Thr Gly Ala Asp Ala Ala Asp Ser Gly
2360              2365              2370 gat cgg aca ccc cct gac gag ttg gct ctt tcg gag aca ggt tct acc    7507
Asp Arg Thr Pro Pro Asp Glu Leu Ala Leu Ser Glu Thr Gly Ser Thr
    2375              2380              2385 tcc tcc atg ccc ccc ctc gag ggg gag cct ggg gac cca gac ctg gag    7555
Ser Ser Met Pro Pro Leu Glu Gly Glu Pro Gly Asp Pro Asp Leu Glu
2390              2395              2400              2405 cct gag cag gta gag ctt caa cct cct ccc cag ggg ggg gag gca gct    7603
Pro Glu Gln Val Glu Leu Gln Pro Pro Pro Gln Gly Gly Glu Ala Ala
```

```
                   2410              2415              2420
ccc ggc tcg gac tcg ggg tcc tgg tct act tgc tcc gag gag gat gac    7651
Pro Gly Ser Asp Ser Gly Ser Trp Ser Thr Cys Ser Glu Glu Asp Asp
        2425              2430              2435 tcc gtc gtg tgc tgc tcc atg tca tat tcc tgg acc ggg gct cta ata    7699
Ser Val Val Cys Cys Ser Met Ser Tyr Ser Trp Thr Gly Ala Leu Ile
        2440              2445              2450 act cct tgt agc ccc gaa gag gaa aag ttg cca att aac tcc ttg agc    7747
Thr Pro Cys Ser Pro Glu Glu Glu Lys Leu Pro Ile Asn Ser Leu Ser
        2455              2460              2465 aac tcg ctg ttg cga tac cat aac aag gta tac tgt act aca tca aag    7795
Asn Ser Leu Leu Arg Tyr His Asn Lys Val Tyr Cys Thr Thr Ser Lys
2470              2475              2480              2485 agt gcc tca cta agg gct aaa aag gta act ttt gat agg atg caa gtg    7843
Ser Ala Ser Leu Arg Ala Lys Lys Val Thr Phe Asp Arg Met Gln Val
        2490              2495              2500 ctc gac gcc tat tat gat tca gtc tta aag gac atc aag cta gcg gcc    7891
Leu Asp Ala Tyr Tyr Asp Ser Val Leu Lys Asp Ile Lys Leu Ala Ala
        2505              2510              2515 tcc aag gtc agc gca agg ctc ctc acc tta gag gag gcg tgc caa ttg    7939
Ser Lys Val Ser Ala Arg Leu Leu Thr Leu Glu Glu Ala Cys Gln Leu
        2520              2525              2530 acc cca ccc cac tct gca aga tcc aag tat ggg ttt ggg gct aag gag    7987
Thr Pro Pro His Ser Ala Arg Ser Lys Tyr Gly Phe Gly Ala Lys Glu
        2535              2540              2545 gtc cgc agc ttg tcc ggg agg gcc gtc aac cac atc aag tcc gtg tgg    8035
Val Arg Ser Leu Ser Gly Arg Ala Val Asn His Ile Lys Ser Val Trp
2550              2555              2560              2565 aag gac ctc ttg gaa gac tca caa aca cca att cct aca acc atc atg    8083
Lys Asp Leu Leu Glu Asp Ser Gln Thr Pro Ile Pro Thr Thr Ile Met
        2570              2575              2580 gcc aaa aat gag gtg ttc tgc gtg gac ccc gcc aag ggg ggt aaa aaa    8131
Ala Lys Asn Glu Val Phe Cys Val Asp Pro Ala Lys Gly Gly Lys Lys
        2585              2590              2595 cca gct cgc ctt atc gtt tac cct gac ctc ggc gtc agg gtc tgc gag    8179
Pro Ala Arg Leu Ile Val Tyr Pro Asp Leu Gly Val Arg Val Cys Glu
        2600              2605              2610 aag atg gcc ctt tat gat gtc aca caa aag ctt cct cag gcg gtg atg    8227
Lys Met Ala Leu Tyr Asp Val Thr Gln Lys Leu Pro Gln Ala Val Met
        2615              2620              2625 ggg gct tct tat ggc ttc cag tac tcc ccc gct cag cgg gtg gag ttt    8275
Gly Ala Ser Tyr Gly Phe Gln Tyr Ser Pro Ala Gln Arg Val Glu Phe
2630              2635              2640              2645 ctc ttg aag gca tgg gcg gaa aag aga gac cct atg ggt ttt tcg tat    8323
Leu Leu Lys Ala Trp Ala Glu Lys Arg Asp Pro Met Gly Phe Ser Tyr
        2650              2655              2660 gat acc cga tgc ttt gac tca acc gtc act gag aga gac atc agg act    8371
Asp Thr Arg Cys Phe Asp Ser Thr Val Thr Glu Arg Asp Ile Arg Thr
        2665              2670              2675 gag gag tcc ata tac cag gcc tgc tcc tta ccc gag gag gcc cga act    8419
Glu Glu Ser Ile Tyr Gln Ala Cys Ser Leu Pro Glu Glu Ala Arg Thr
        2680              2685              2690 gcc ata cac tcg ctg act gag aga ctc tat gtg gga ggg ccc atg ttc    8467
Ala Ile His Ser Leu Thr Glu Arg Leu Tyr Val Gly Gly Pro Met Phe
        2695              2700              2705 aac agc aag ggc cag tcc tgc ggg tac agg cgt tgc cgc gcc agc ggg    8515
Asn Ser Lys Gly Gln Ser Cys Gly Tyr Arg Arg Cys Arg Ala Ser Gly
        2710              2715              2720              2725 gtg ctt acc act agt atg ggg aac acc atc aca tgc tat gta aaa gcc    8563
Val Leu Thr Thr Ser Met Gly Asn Thr Ile Thr Cys Tyr Val Lys Ala
```

|  |  |
|---|---|
| cta gcg gct tgc aag gct gcg ggg ata att gcg ccc acg atg ctg gta<br>Leu Ala Ala Cys Lys Ala Ala Gly Ile Ile Ala Pro Thr Met Leu Val<br>2745     2750     2755 | 8611 |
| tgc ggc gac gac ttg gtc gtc atc tca gaa agc cag ggg act gag gag<br>Cys Gly Asp Asp Leu Val Val Ile Ser Glu Ser Gln Gly Thr Glu Glu<br>  2760     2765     2770 | 8659 |
| gac gag cgg aac ctg aga gcc ttc acg gag gct atg acc agg tat tct<br>Asp Glu Arg Asn Leu Arg Ala Phe Thr Glu Ala Met Thr Arg Tyr Ser<br>2775     2780     2785 | 8707 |
| gcc cct cct ggt gac ccc ccc aga ccg gaa tat gac ctg gag cta ata<br>Ala Pro Pro Gly Asp Pro Pro Arg Pro Glu Tyr Asp Leu Glu Leu Ile<br>2790     2795     2800     2805 | 8755 |
| aca tct tgt tcc tca aac gtg tct gtg gca ctt ggc cca cag ggc cgc<br>Thr Ser Cys Ser Ser Asn Val Ser Val Ala Leu Gly Pro Gln Gly Arg<br>  2810     2815     2820 | 8803 |
| cgc aga tac tac ctg acc aga gac ccc acc act tca att gcc cgg gct<br>Arg Arg Tyr Tyr Leu Thr Arg Asp Pro Thr Thr Ser Ile Ala Arg Ala<br>2825     2830     2835 | 8851 |
| gcc tgg gaa aca gtt aga cac tcc cct gtc aat tca tgg ctg gga aac<br>Ala Trp Glu Thr Val Arg His Ser Pro Val Asn Ser Trp Leu Gly Asn<br>2840     2845     2850 | 8899 |
| atc atc cag tac gct cca acc ata tgg gtt cgc atg gtc ctg atg aca<br>Ile Ile Gln Tyr Ala Pro Thr Ile Trp Val Arg Met Val Leu Met Thr<br>2855     2860     2865 | 8947 |
| cac ttc ttc tcc att ctc atg gcc cag gac acc cta gac cag aac ctt<br>His Phe Phe Ser Ile Leu Met Ala Gln Asp Thr Leu Asp Gln Asn Leu<br>2870     2875     2880     2885 | 8995 |
| aac ttt gaa atg tac gga tcg gtg tac tcc gtg agt cct ctg gac ctc<br>Asn Phe Glu Met Tyr Gly Ser Val Tyr Ser Val Ser Pro Leu Asp Leu<br>  2890     2895     2900 | 9043 |
| cca gcc ata att gaa agg tta cac ggg ctt gac gcc ttc tct ctg cac<br>Pro Ala Ile Ile Glu Arg Leu His Gly Leu Asp Ala Phe Ser Leu His<br>2905     2910     2915 | 9091 |
| aca tac act ccc cac gaa ctg acg cgg gtg gct tca gcc ctc aga aaa<br>Thr Tyr Thr Pro His Glu Leu Thr Arg Val Ala Ser Ala Leu Arg Lys<br>2920     2925     2930 | 9139 |
| ctt ggg gcg cca ccc ctc aga gcg tgg aag agt cgg gcg cgt gca gtt<br>Leu Gly Ala Pro Pro Leu Arg Ala Trp Lys Ser Arg Ala Arg Ala Val<br>2935     2940     2945 | 9187 |
| agg gcg tcc ctc atc tcc cgt ggg ggg agg gcg gcc gtt tgc ggt cgg<br>Arg Ala Ser Leu Ile Ser Arg Gly Gly Arg Ala Ala Val Cys Gly Arg<br>2950     2955     2960     2965 | 9235 |
| tac ctc ttc aac tgg gcg gtg aag acc aag ctc aaa ctc act cct ttg<br>Tyr Leu Phe Asn Trp Ala Val Lys Thr Lys Leu Lys Leu Thr Pro Leu<br>  2970     2975     2980 | 9283 |
| ccg gag gca cgc ctc ctg gat ttg tcc agt tgg ttt acc gtc ggc gcc<br>Pro Glu Ala Arg Leu Leu Asp Leu Ser Ser Trp Phe Thr Val Gly Ala<br>2985     2990     2995 | 9331 |
| ggc ggg ggc gac att tat cac agc gtg tcg cgt gcc cga ccc cgc cta<br>Gly Gly Gly Asp Ile Tyr His Ser Val Ser Arg Ala Arg Pro Arg Leu<br>3000     3005     3010 | 9379 |
| tta ctc ctt agc cta ctc cta ctt tct gta ggg gta ggc ctc ttc cta<br>Leu Leu Leu Ser Leu Leu Leu Leu Ser Val Gly Val Gly Leu Phe Leu<br>  3015     3020     3025 | 9427 |
| ctc ccc gct cga tag agcggcacac attagctaca ctccatagct aactgttcct<br>Leu Pro Ala Arg<br>3030 | 9482 |
| tttttttttt tttttttttt tttttttttt ttttttctt tttttttttt tttccctctt | 9542 |

-continued

```
tcttcccttc tcatcttatt ctactttctt tcttggtggc tccatcttag ccctggtcac    9602
ggctagctgt gaaaggtccg tgagccgcat gactgcagag agtgccgtaa ctggtctctc    9662
tgcagatcat gt                                                        9674
```

<210> SEQ ID NO 6
<211> LENGTH: 3033
<212> TYPE: PRT
<213> ORGANISM: Hepatitis C virus

<400> SEQUENCE: 6

```
Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Thr Arg Lys Ala Ser Glu Arg Ser Gln Pro Arg Gly Arg Arg Gln Pro
         50                  55                  60

Ile Pro Lys His Arg Arg Ser Thr Gly Lys Ser Trp Gly Lys Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Asn Asp Pro
                100                 105                 110

Arg His Arg Ser Arg Asn Val Gly Lys Val Ile Asp Thr Leu Thr Cys
            115                 120                 125

Gly Phe Ala Asp Leu Leu Gly Tyr Val Pro Val Val Gly Ala Pro Leu
        130                 135                 140

Ser Gly Val Ala Ser Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Val
                180                 185                 190

Gln Val Lys Asn Thr Ser Asn Ala Tyr Met Ala Thr Asn Asp Cys Ser
            195                 200                 205

Asn Asp Ser Ile Thr Trp Gln Leu Glu Ala Ala Val Leu His Val Pro
        210                 215                 220

Gly Cys Val Pro Cys Glu Lys Met Gly Asn Thr Ser Arg Cys Trp Ile
225                 230                 235                 240

Pro Val Ser Pro Asn Val Ala Val Arg Gln Pro Gly Ala Leu Thr Arg
                245                 250                 255

Gly Leu Arg Thr His Ile Asp Met Val Val Leu Ser Ala Thr Leu Cys
            260                 265                 270

Ser Ala Leu Tyr Val Gly Asp Leu Cys Gly Gly Val Met Leu Ala Ser
        275                 280                 285

Gln Met Phe Ile Val Ser Pro Gln His His Trp Phe Val Gln Glu Cys
    290                 295                 300

Asn Cys Ser Ile Tyr Pro Gly Ala Ile Thr Gly His Arg Met Ala Trp
305                 310                 315                 320

Asp Met Met Met Asn Trp Ser Pro Thr Thr Met Ile Leu Ala Tyr
                325                 330                 335

Val Met Arg Val Pro Glu Val Ile Asp Ile Ser Gly Ala His
            340                 345                 350
```

-continued

```
Trp Gly Val Met Phe Gly Leu Ala Tyr Phe Ser Met Gln Gly Ala Trp
            355                 360                 365

Ala Lys Val Val Val Ile Leu Leu Ala Ser Gly Val Asp Ala Tyr
370                 375                 380

Thr Thr Thr Thr Gly Ser Ala Ala Gly Arg Thr Thr Ser Ser Leu Ala
385                 390                 395                 400

Ser Ala Phe Ser Pro Gly Ala Arg Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Phe Thr Ala Leu Phe Tyr Ile His Lys Phe Asn
            435                 440                 445

Ser Ser Gly Cys Pro Glu Arg Leu Ser Ala Cys Arg Asn Ile Glu Asp
450                 455                 460

Phe Arg Ile Gly Trp Gly Ala Leu Gln Tyr Asp Asp Asn Val Thr Asn
465                 470                 475                 480

Pro Glu Asp Met Arg Pro Tyr Cys Trp His Tyr Pro Lys Gln Cys
                485                 490                 495

Gly Val Val Pro Ala Gly Thr Val Cys Gly Pro Val Tyr Cys Phe Thr
                500                 505                 510

Pro Ser Pro Val Val Val Gly Thr Thr Asp Arg Leu Gly Val Pro Thr
                515                 520                 525

Tyr Thr Trp Gly Glu Asn Glu Thr Asp Val Phe Leu Leu Asn Ser Thr
    530                 535                 540

Arg Pro Pro Ser Gly Ser Trp Phe Gly Cys Thr Trp Met Asn Ser Thr
545                 550                 555                 560

Gly Phe Thr Lys Thr Cys Gly Ala Pro Pro Cys Arg Thr Arg Ala Asp
                565                 570                 575

Phe Asn Thr Ser Thr Asp Leu Leu Cys Pro Thr Asp Cys Phe Arg Lys
                580                 585                 590

His Pro Glu Ala Thr Tyr Ile Lys Cys Gly Ser Gly Pro Trp Leu Thr
                595                 600                 605

Pro Lys Cys Leu Val Asp Tyr Pro Tyr Arg Leu Trp His Tyr Pro Cys
    610                 615                 620

Thr Val Asn Tyr Ser Thr Phe Lys Ile Arg Met Tyr Val Gly Gly Val
625                 630                 635                 640

Glu His Arg Leu Met Ala Ala Cys Asn Phe Thr Arg Gly Asp Arg Cys
                645                 650                 655

Asn Leu Glu Asp Arg Asp Arg Ser Gln Gln Thr Pro Leu Leu His Ser
                660                 665                 670

Thr Thr Glu Trp Ala Ile Leu Pro Cys Ser Phe Ser Asp Leu Pro Ala
            675                 680                 685

Leu Ser Thr Gly Leu Leu His Leu His Gln Asn Ile Val Asp Val Gln
    690                 695                 700

Tyr Met Tyr Gly Leu Ser Pro Ala Leu Thr Gln Tyr Ile Val Arg Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Leu Leu Gly Gln Ala Glu Ala Ala Leu
                740                 745                 750

Glu Lys Leu Val Val Leu His Ala Ala Ser Ala Ala Ser Cys Asn Gly
            755                 760                 765

Phe Leu Tyr Phe Val Ile Phe Leu Val Ala Ala Trp His Ile Lys Gly
770                 775                 780
```

```
Arg Val Val Pro Leu Ala Ala Tyr Ser Leu Thr Gly Leu Trp Pro Phe
785                 790                 795                 800

Cys Leu Leu Leu Leu Ala Leu Pro Gln Gln Ala Tyr Ala Tyr Asp Ala
                805                 810                 815

Ser Val His Gly Gln Val Gly Ala Ala Leu Leu Val Leu Ile Thr Leu
            820                 825                 830

Phe Thr Leu Thr Pro Gly Tyr Lys Thr Leu Leu Ser Gln Ser Leu Trp
        835                 840                 845

Trp Leu Cys Tyr Leu Leu Thr Leu Ala Glu Thr Met Val Gln Glu Trp
    850                 855                 860

Ala Pro Ser Met Gln Ala Arg Gly Gly Arg Asp Gly Ile Ile Trp Ala
865                 870                 875                 880

Ala Thr Ile Phe Cys Pro Gly Val Val Phe Asp Ile Thr Lys Trp Leu
                885                 890                 895

Leu Ala Val Leu Gly Pro Gly Tyr Leu Leu Arg Gly Ala Leu Thr Arg
            900                 905                 910

Val Pro Tyr Phe Val Arg Ala His Ala Leu Leu Arg Met Cys Thr Met
        915                 920                 925

Val Arg His Leu Ala Gly Gly Arg Tyr Val Gln Met Ala Leu Leu Ala
    930                 935                 940

Leu Gly Arg Trp Thr Gly Thr Tyr Ile Tyr Asp His Leu Thr Pro Met
945                 950                 955                 960

Ser Asp Trp Ala Ala Ser Gly Leu Arg Asp Leu Ala Val Ala Val Glu
                965                 970                 975

Pro Ile Ile Phe Ser Pro Met Glu Lys Lys Val Ile Val Trp Gly Ala
            980                 985                 990

Glu Thr Ala Ala Cys Gly Asp Ile Leu His Gly Leu Pro Val Ser Ala
        995                 1000                1005

Arg Leu Gly Arg Glu Ile Leu Leu Gly Pro Ala Asp Gly Tyr Thr Ser
    1010                1015                1020

Lys Gly Trp Lys Leu Leu Ala Pro Ile Thr Ala Tyr Ala Gln Gln Thr
1025                1030                1035                1040

Arg Gly Leu Leu Gly Ser Ile Val Val Ser Met Thr Gly Arg Asp Lys
                1045                1050                1055

Thr Glu Gln Ala Gly Glu Val Gln Val Leu Ser Thr Val Thr Gln Ser
            1060                1065                1070

Phe Leu Gly Thr Ser Ile Ser Gly Val Leu Trp Thr Val Tyr His Gly
        1075                1080                1085

Ala Gly Asn Lys Thr Leu Ala Gly Ser Arg Gly Pro Val Thr Gln Met
    1090                1095                1100

Tyr Ser Ser Ala Glu Gly Asp Leu Val Gly Trp Pro Ser Pro Pro Gly
1105                1110                1115                1120

Thr Lys Ser Leu Glu Pro Cys Thr Cys Gly Ala Val Asp Leu Tyr Leu
                1125                1130                1135

Val Thr Arg Asn Ala Asp Val Ile Pro Ala Arg Arg Arg Gly Asp Lys
            1140                1145                1150

Arg Gly Ala Leu Leu Ser Pro Arg Pro Leu Ser Thr Leu Lys Gly Ser
        1155                1160                1165

Ser Gly Gly Pro Val Leu Cys Pro Arg Gly His Ala Val Gly Ile Phe
    1170                1175                1180

Arg Ala Ala Val Cys Ser Arg Gly Val Ala Lys Ser Ile Asp Phe Ile
1185                1190                1195                1200

Pro Val Glu Thr Leu Asp Ile Val Thr Arg Ser Pro Thr Phe Ser Asp
```

-continued

```
                1205                1210                1215
Asn Ser Thr Pro Pro Ala Val Pro Gln Thr Tyr Gln Val Gly Tyr Leu
        1220                1225                1230
His Ala Pro Thr Gly Ser Gly Lys Ser Thr Lys Val Pro Val Ala Tyr
    1235                1240                1245
Ala Ala Gln Gly Tyr Lys Val Leu Val Leu Asn Pro Ser Val Ala Ala
1250                1255                1260
Thr Leu Gly Phe Gly Ala Tyr Leu Ser Lys Ala His Gly Ile Asn Pro
1265                1270                1275                1280
Asn Ile Arg Thr Gly Val Arg Thr Val Thr Thr Gly Glu Pro Ile Thr
        1285                1290                1295
Tyr Ser Thr Tyr Gly Lys Phe Leu Ala Asp Gly Gly Cys Ala Gly Gly
    1300                1305                1310
Ala Tyr Asp Ile Ile Ile Cys Asp Glu Cys His Ser Val Asp Ala Thr
    1315                1320                1325
Thr Ile Leu Gly Ile Gly Thr Val Leu Asp Gln Ala Glu Thr Ala Gly
    1330                1335                1340
Val Arg Leu Thr Val Leu Ala Thr Ala Thr Pro Pro Gly Ser Val Thr
1345                1350                1355                1360
Thr Pro His Pro Asn Ile Glu Glu Val Ala Leu Gly Gln Glu Gly Glu
            1365                1370                1375
Ile Pro Phe Tyr Gly Arg Ala Phe Pro Leu Ser Tyr Ile Lys Gly Gly
        1380                1385                1390
Arg His Leu Ile Phe Cys His Ser Lys Lys Lys Cys Asp Glu Leu Ala
        1395                1400                1405
Thr Ala Leu Arg Gly Met Gly Leu Asn Ala Val Ala Tyr Tyr Arg Gly
    1410                1415                1420
Leu Asp Val Ser Ile Ile Pro Thr Gln Gly Asp Val Val Val Val Ala
1425                1430                1435                1440
Thr Asp Ala Leu Met Thr Gly Tyr Thr Gly Asp Phe Asp Ser Val Ile
            1445                1450                1455
Asp Cys Asn Val Ala Val Thr Gln Ala Val Asp Phe Ser Leu Asp Pro
        1460                1465                1470
Thr Phe Thr Ile Thr Thr Gln Thr Val Pro Gln Asp Ala Val Ser Arg
    1475                1480                1485
Ser Gln Arg Arg Gly Arg Thr Gly Arg Gly Arg Leu Gly Ile Tyr Arg
    1490                1495                1500
Tyr Val Ser Thr Gly Glu Arg Ala Ser Gly Met Phe Asp Ser Val Val
1505                1510                1515                1520
Leu Cys Glu Cys Tyr Asp Ala Gly Ala Ala Trp Tyr Glu Leu Ser Pro
            1525                1530                1535
Val Glu Thr Thr Val Arg Leu Arg Ala Tyr Phe Asn Thr Pro Gly Leu
        1540                1545                1550
Pro Val Cys Gln Asp His Leu Glu Phe Trp Glu Ala Val Phe Thr Gly
        1555                1560                1565
Leu Thr His Ile Asp Ala His Phe Leu Ser Gln Thr Lys Gln Ser Gly
    1570                1575                1580
Glu Asn Phe Ala Tyr Leu Val Ala Tyr Gln Ala Thr Val Cys Ala Arg
1585                1590                1595                1600
Ala Lys Ala Pro Pro Pro Ser Trp Asp Val Met Trp Lys Cys Leu Thr
            1605                1610                1615
Arg Leu Lys Pro Thr Leu Val Gly Pro Thr Pro Leu Leu Tyr Arg Leu
        1620                1625                1630
```

```
Gly Ser Val Thr Asn Glu Val Thr Leu Thr His Pro Val Thr Lys Tyr
        1635                1640                1645

Ile Ala Thr Cys Met Gln Ala Asp Leu Glu Val Met Thr Ser Thr Trp
    1650                1655                1660

Val Leu Ala Gly Gly Val Leu Ala Ala Val Ala Ala Tyr Cys Leu Ala
1665                1670                1675                1680

Thr Gly Cys Val Ser Ile Ile Gly Arg Leu His Ile Asn Gln Arg Ala
            1685                1690                1695

Val Val Ala Pro Asp Lys Glu Val Leu Tyr Glu Ala Phe Asp Glu Met
                1700                1705                1710

Glu Glu Cys Ala Ser Arg Ala Ala Leu Leu Glu Glu Gly Gln Arg Ile
    1715                1720                1725

Ala Glu Met Leu Lys Ser Lys Ile Gln Gly Leu Leu Gln Gln Ala Ser
        1730                1735                1740

Lys Gln Ala Gln Asp Ile Gln Pro Ala Val Gln Ala Ser Trp Pro Lys
1745                1750                1755                1760

Met Glu Gln Phe Trp Ala Lys His Met Trp Asn Phe Ile Ser Gly Ile
            1765                1770                1775

Gln Tyr Leu Ala Gly Leu Ser Thr Leu Pro Gly Asn Pro Ala Val Ala
                1780                1785                1790

Ser Met Met Ala Phe Ser Ala Ala Leu Thr Ser Pro Leu Ser Thr Ser
        1795                1800                1805

Thr Thr Ile Leu Leu Asn Ile Leu Gly Gly Trp Leu Ala Ser Gln Ile
    1810                1815                1820

Ala Pro Pro Ala Gly Ala Thr Gly Phe Val Val Ser Gly Leu Val Gly
1825                1830                1835                1840

Ala Ala Val Gly Ser Ile Gly Leu Gly Lys Val Leu Val Asp Ile Leu
            1845                1850                1855

Ala Gly Tyr Gly Ala Gly Ile Ser Gly Ala Leu Val Ala Phe Lys Ile
                1860                1865                1870

Met Ser Gly Glu Lys Pro Ser Met Glu Asp Val Ile Asn Leu Leu Pro
        1875                1880                1885

Gly Ile Leu Ser Pro Gly Ala Leu Val Val Gly Val Ile Cys Ala Ala
    1890                1895                1900

Ile Leu Arg Arg His Val Gly Pro Gly Glu Gly Ala Val Gln Trp Met
1905                1910                1915                1920

Asn Arg Leu Ile Ala Phe Ala Ser Arg Gly Asn His Val Ala Pro Thr
            1925                1930                1935

His Tyr Val Thr Glu Ser Asp Ala Ser Gln Arg Val Thr Gln Leu Leu
                1940                1945                1950

Gly Ser Leu Thr Ile Thr Ser Leu Leu Arg Arg Leu His Asn Trp Ile
        1955                1960                1965

Thr Glu Asp Cys Pro Ile Pro Cys Ala Gly Ser Trp Leu Arg Asp Val
    1970                1975                1980

Trp Asp Trp Val Cys Thr Ile Leu Thr Asp Phe Lys Asn Trp Leu Thr
1985                1990                1995                2000

Ser Lys Leu Phe Pro Lys Met Pro Gly Leu Pro Phe Ile Ser Cys Gln
            2005                2010                2015

Lys Gly Tyr Lys Gly Val Trp Ala Gly Thr Gly Ile Met Thr Thr Arg
                2020                2025                2030

Cys Pro Cys Gly Ala Asn Ile Ser Gly Asn Val Arg Leu Gly Ser Met
        2035                2040                2045

Arg Ile Thr Gly Pro Lys Thr Cys Met Asn Thr Trp Gln Gly Thr Phe
    2050                2055                2060
```

-continued

Pro Ile Asn Cys Tyr Thr Glu Gly Gln Cys Leu Pro Lys Pro Ala Leu
2065                2070                2075                2080

Asn Phe Lys Thr Ala Ile Trp Arg Val Ala Ala Ser Glu Tyr Ala Glu
            2085                2090                2095

Val Thr Gln His Gly Ser Tyr Ala Tyr Ile Thr Gly Leu Thr Thr Asp
        2100                2105                2110

Asn Leu Lys Val Pro Cys Gln Leu Pro Ser Pro Glu Phe Phe Ser Trp
    2115                2120                2125

Val Asp Gly Val Gln Ile His Arg Ser Ala Pro Thr Pro Lys Pro Phe
2130                2135                2140

Phe Arg Asp Glu Val Ser Phe Ser Val Gly Leu Asn Ser Phe Val Val
2145                2150                2155                2160

Gly Ser Gln Leu Pro Cys Asp Pro Glu Pro Asp Thr Glu Val Val Met
            2165                2170                2175

Ser Met Leu Thr Asp Pro Ser His Ile Thr Ala Glu Ala Ala Ala Arg
        2180                2185                2190

Arg Leu Ala Arg Gly Ser Pro Pro Ser Glu Ala Ser Ser Ser Ala Ser
    2195                2200                2205

Gln Leu Ser Ala Pro Ser Leu Arg Ala Thr Cys Thr Thr His Gly Arg
2210                2215                2220

Thr Tyr Asp Val Asp Met Val Asp Ala Asn Leu Phe Met Gly Gly Gly
2225                2230                2235                2240

Val Ile Arg Ile Glu Ser Glu Ser Lys Val Val Leu Asp Ser Leu
            2245                2250                2255

Asp Ser Met Thr Glu Glu Gly Asp Leu Glu Pro Ser Val Pro Ser
        2260                2265                2270

Glu Tyr Met Leu Pro Arg Lys Arg Phe Pro Pro Ala Leu Pro Ala Trp
    2275                2280                2285

Ala Arg Pro Asp Tyr Asn Pro Pro Leu Val Glu Ser Trp Lys Arg Pro
2290                2295                2300

Asp Tyr Gln Pro Pro Thr Val Ala Gly Cys Ala Leu Pro Pro Pro Lys
2305                2310                2315                2320

Lys Thr Pro Thr Pro Pro Arg Arg Arg Arg Thr Val Gly Leu Ser
            2325                2330                2335

Glu Ser Thr Ile Gly Asp Ala Leu Gln Gln Leu Ala Ile Lys Ser Phe
        2340                2345                2350

Gly Gln Pro Pro Pro Ser Gly Asp Ser Gly Leu Ser Thr Gly Ala Asp
    2355                2360                2365

Ala Ala Asp Ser Gly Asp Arg Thr Pro Pro Asp Glu Leu Ala Leu Ser
2370                2375                2380

Glu Thr Gly Ser Thr Ser Ser Met Pro Pro Leu Glu Gly Glu Pro Gly
2385                2390                2395                2400

Asp Pro Asp Leu Glu Pro Glu Gln Val Glu Leu Gln Pro Pro Gln
            2405                2410                2415

Gly Gly Glu Ala Ala Pro Gly Ser Asp Ser Gly Ser Trp Ser Thr Cys
        2420                2425                2430

Ser Glu Glu Asp Asp Ser Val Val Cys Cys Ser Met Ser Tyr Ser Trp
    2435                2440                2445

Thr Gly Ala Leu Ile Thr Pro Cys Ser Pro Glu Glu Glu Lys Leu Pro
2450                2455                2460

Ile Asn Ser Leu Ser Asn Ser Leu Leu Arg Tyr His Asn Lys Val Tyr
2465                2470                2475                2480

Cys Thr Thr Ser Lys Ser Ala Ser Leu Arg Ala Lys Lys Val Thr Phe

```
                    2485                2490                2495
Asp Arg Met Gln Val Leu Asp Ala Tyr Tyr Asp Ser Val Leu Lys Asp
        2500                2505                2510

Ile Lys Leu Ala Ala Ser Lys Val Ser Ala Arg Leu Leu Thr Leu Glu
        2515                2520                2525

Glu Ala Cys Gln Leu Thr Pro Pro His Ser Ala Arg Ser Lys Tyr Gly
        2530                2535                2540

Phe Gly Ala Lys Glu Val Arg Ser Leu Ser Gly Arg Ala Val Asn His
2545                2550                2555                2560

Ile Lys Ser Val Trp Lys Asp Leu Leu Glu Asp Ser Gln Thr Pro Ile
        2565                2570                2575

Pro Thr Thr Ile Met Ala Lys Asn Glu Val Phe Cys Val Asp Pro Ala
        2580                2585                2590

Lys Gly Gly Lys Lys Pro Ala Arg Leu Ile Val Tyr Pro Asp Leu Gly
        2595                2600                2605

Val Arg Val Cys Glu Lys Met Ala Leu Tyr Asp Val Thr Gln Lys Leu
        2610                2615                2620

Pro Gln Ala Val Met Gly Ala Ser Tyr Gly Phe Gln Tyr Ser Pro Ala
2625                2630                2635                2640

Gln Arg Val Glu Phe Leu Leu Lys Ala Trp Ala Glu Lys Arg Asp Pro
        2645                2650                2655

Met Gly Phe Ser Tyr Asp Thr Arg Cys Phe Asp Ser Thr Val Thr Glu
        2660                2665                2670

Arg Asp Ile Arg Thr Glu Glu Ser Ile Tyr Gln Ala Cys Ser Leu Pro
        2675                2680                2685

Glu Glu Ala Arg Thr Ala Ile His Ser Leu Thr Glu Arg Leu Tyr Val
        2690                2695                2700

Gly Gly Pro Met Phe Asn Ser Lys Gly Gln Ser Cys Gly Tyr Arg Arg
2705                2710                2715                2720

Cys Arg Ala Ser Gly Val Leu Thr Thr Ser Met Gly Asn Thr Ile Thr
        2725                2730                2735

Cys Tyr Val Lys Ala Leu Ala Ala Cys Lys Ala Ala Gly Ile Ile Ala
        2740                2745                2750

Pro Thr Met Leu Val Cys Gly Asp Asp Leu Val Val Ile Ser Glu Ser
        2755                2760                2765

Gln Gly Thr Glu Glu Asp Glu Arg Asn Leu Arg Ala Phe Thr Glu Ala
        2770                2775                2780

Met Thr Arg Tyr Ser Ala Pro Pro Gly Asp Pro Pro Arg Pro Glu Tyr
2785                2790                2795                2800

Asp Leu Glu Leu Ile Thr Ser Cys Ser Ser Asn Val Ser Val Ala Leu
        2805                2810                2815

Gly Pro Gln Gly Arg Arg Arg Tyr Tyr Leu Thr Arg Asp Pro Thr Thr
        2820                2825                2830

Ser Ile Ala Arg Ala Ala Trp Glu Thr Val Arg His Ser Pro Val Asn
        2835                2840                2845

Ser Trp Leu Gly Asn Ile Ile Gln Tyr Ala Pro Thr Ile Trp Val Arg
        2850                2855                2860

Met Val Leu Met Thr His Phe Phe Ser Ile Leu Met Ala Gln Asp Thr
2865                2870                2875                2880

Leu Asp Gln Asn Leu Asn Phe Glu Met Tyr Gly Ser Val Tyr Ser Val
        2885                2890                2895

Ser Pro Leu Asp Leu Pro Ala Ile Ile Glu Arg Leu His Gly Leu Asp
        2900                2905                2910
```

-continued

```
Ala Phe Ser Leu His Thr Tyr Thr Pro His Glu Leu Thr Arg Val Ala
        2915                2920                2925

Ser Ala Leu Arg Lys Leu Gly Ala Pro Pro Leu Arg Ala Trp Lys Ser
2930                2935                2940

Arg Ala Arg Ala Val Arg Ala Ser Leu Ile Ser Arg Gly Gly Arg Ala
2945                2950                2955                2960

Ala Val Cys Gly Arg Tyr Leu Phe Asn Trp Ala Val Lys Thr Lys Leu
            2965                2970                2975

Lys Leu Thr Pro Leu Pro Glu Ala Arg Leu Leu Asp Leu Ser Ser Trp
        2980                2985                2990

Phe Thr Val Gly Ala Gly Gly Gly Asp Ile Tyr His Ser Val Ser Arg
    2995                3000                3005

Ala Arg Pro Arg Leu Leu Leu Leu Ser Leu Leu Leu Leu Ser Val Gly
    3010                3015                3020

Val Gly Leu Phe Leu Leu Pro Ala Arg
3025                3030
```

<210> SEQ ID NO 7
<211> LENGTH: 8024
<212> TYPE: RNA
<213> ORGANISM: Artificial Sequence
<220> FEATURE:
<223> OTHER INFORMATION: HCV-derived synthetically created replicon RNA rSGREP-JFH1/GND

<400> SEQUENCE: 7

| | | |
|---|---|---|
| accugcccu aauagggcg acacuccgcc augaaucacu ccccugugag gaacuacugu | 60 |
| cuucacgcag aaagcgccua gccauggcgu uaguaugagu gucguacagc cuccaggccc | 120 |
| ccccucccg ggagagccau aguggucugc ggaaccggug aguacaccgg aauugccggg | 180 |
| aagacugggu ccuuucuugg auaaacccac ucuaugcccg gccauuuggg cgugcccccg | 240 |
| caagacugcu agccgaguag cguugggug cgaaaggccu ugguacacug ccugauaggg | 300 |
| cgcuugcgag ugccccggga ggucucguag accgugcacc augagcacaa auccuaaacc | 360 |
| ucaaagaaaa accaaaagaa acaccaaccg ucgcccaaug auugaacaag auggauugca | 420 |
| cgcagguucu ccggccgcuu ggguggagag gcuauucggc uaugacuggg cacaacagac | 480 |
| aaucggcugc ucugaugccg ccguguuccg gcugucagcg caggggcgcc cgguucuuuu | 540 |
| ugucaagacc gaccugcccg gugcccugaa ugaacugcag gacgaggcag cgcggcuauc | 600 |
| guggcuggcc acgacgggcg uuccuugcgc agcugugcuc gacguuguca cugaagcggg | 660 |
| aagggacugg cugcuauugg gcgaagugcc ggggcaggau cuccugucau cucaccuugc | 720 |
| uccugccgag aaaguaucca ucauggcuga ugcaaugcgg cggcugcaua cgcuugaucc | 780 |
| ggcuaccugc ccauucgacc accaagcgaa acaucgcauc gagcgagcac guacuccggau | 840 |
| ggaagccggu cuugucgauc aggaugaucu ggacgaagag caucagggc ucgcgccagc | 900 |
| cgaacuguuc gccaggcuca aggcgcgcau gcccgacggc gaggaucucg ucugacccca | 960 |
| uggcgaugcc ugcuugccga auaucauggu ggaaaauggc cgcuuuucug gauucaucga | 1020 |
| cuguggccgg cugggugugg cggaccgcua ucaggacaua gcguuggcua cccgugauau | 1080 |
| ugcugaagag cuuggcggcg aaugggcuga ccgcuuccuc gugcuuuacg uaucgccgc | 1140 |
| ucccgauucg cagcgcaucg ccuucuaucc ccuucugac gaguucuucu gaguuuaaac | 1200 |
| ccucucccuc ccccccccu aacguuacug gccgaagccg cuuggaauaa ggccggugug | 1260 |
| cguuugcua uauguauuu uccaccauau ugccgucuuu uggcaaugug agggcccgga | 1320 |
| aaccuggccc ugucuucuug acgagcauuc cuagggguc uuccccucuc gccaaaggaa | 1380 |

-continued

```
ugcaaggucu guugaauguc gugaaggaag caguucccucu ggaagcuucu ugaagacaaa    1440
caacgucugu agcgacccuu ugcaggcagc ggaaccccccc accuggcgac aggugccucu    1500
gcggccaaaa gccacgugua aagauacac cugcaaaggc ggcacaaccc cagugccacg      1560
uugugaguug gauaguugug gaaagaguca aauggcucuc ucaagcgua uucaacaagg      1620 ggcugaagga ugcccagaag guaccccauu guaugggauc ugaucugggg ccucggugca    1680
caugcuuuac auguguuuag ucgagguuaa aaaaacgucu aggccccccg aaccacgggg    1740
acguggauuu ccuuugaaaa acacgaugau accauggcuc ccaucacugc uuaugcccag    1800
caaacacgag gccuccuggg cgccauagu gugaguauga cggggcguga caggacagaa      1860
caggccgggg aaguccaaau ccuguccaca gucucucagu ccuuccucgg aacaaccauc    1920
ucggggguuu uguggacugu uuaccaccgga gcuggcaaca agacucuagc cggcuuacgg    1980
gguccgguca cgcagaugua ucgagugcuc gagggggacu ugguaggcug gcccagcccc    2040
ccugggacca agucuuugga gccgugcaag uguggagccg ucgaccuaua ucggucacg     2100 cggaacgcug augucauccc ggcucggaga cgcggggaca agcggggagc auugcucucc    2160
ccgagaccca uuucgaccuu gaaggggucc ucggggggc cggugcucug cccuaggggc      2220
cacgucguug ggcucuuccg agcagcugug ugcucucggg gcguggccaa auccaucgau    2280
uucauccccg uugagacacu cgacguuguu acaaggucuc ccacuuucag ugacaacagc    2340
acgccaccgg cugugcccca gaccuaucag gucggguacu ugcaugcucc aacuggcagu    2400
ggaaagagca ccaaggcccc ugucgcguau gccgcccagg gguacaaagu acuagugcuu    2460
aaccccucgg uagcugccac ccuggggguuu ggggcguacc uauccaaggc acauggcauc    2520
aaucccaaca uuaggacugg agucaggacc gugaugaccg gggaggccau cacguacucc    2580
acauauggca aauuucucgc cgauggggggc ugcgcuagcg gcgccauga caucaucaua    2640 ugcgaugaau gccacgcgu ggaugcuacc uccauucucg gcaucggaac gguccuugau      2700
caagcagaga cagccggggu cagacuaacu gugcuggcua cggccacacc ccccgggguca    2760 gugacaaccc cccauccccga uauagaaaag guaggccucg ggcgggagg ugagaucccc     2820 uucuauggga gggcgauucc ccuauccugc aucaaggag ggagacaccu gauuuucugc     2880
cacucaaaga aaaagugugua cgagcucgcg gcggcccuuc ggggcauggg cuugaaugcc    2940
guggcauacu auagagggu ggacgucccc auaauaccag cucagggaga guggugguc       3000 gucgccaccg acgcccucau gacggguac acuggagacu uugacuccgu gaucgacugc     3060 aaugagcgg ucacccaagc ugucgacuuc agccuggacc ccaccuucac uauaaccaca    3120 cagacuguccc cacaagacgc ugucucacgu agucagcgcc gcgggcgcac agguagagga    3180
agacagggca cuuauaggua uguuccacu ggugaacgag ccucaggaau guuugacagu    3240
guagugcuuu ugagugcua cgacgcaggg gcugcguggu acgaucucac accagcggag    3300
accaccguca ggcuuagagc guauuucaac acgcccggcc uacccgugug ucaagaccau    3360
cuugaauuuu gggaggcagu uuucaccggc ucacacaca uagacgccca cuucccucuc     3420
caaacaaagc aagcggggga gaacuucgcg uaccuaguag ccuaccaagc uacgugugc     3480 gccagagcca aggcccuccc ccgucccugg gacgccaugu ggaagugccu ggcccgacuc    3540
aagccuacgc uugcgggccc cacaccucuc cuguaccguu ugggcccuau uaccaaugag    3600
gucacccuca cacacccugg gacgaaguac aucgccacau gcaugcaagc ugaccuugag    3660
gucaugacca gcacguggu ccuagcugga ggagucccugg cagccgucgc cgcauauugc    3720
cuggcgacug gaugcguuuc caucaucggc cgcuugcacg ucaaccagcg agucgucguu    3780
```

```
gcgccggaua aggaggnccu guaugaggcu uuugaugaga uggaggaaug cgccucuagg   3840
gcggcucuca ucgaagaggg gcagcggaua gccgagaugu ugaagnccaa gauccaaggc   3900
uugcugcagc aggccucuaa gcaggcccag gacauacaac ccgcuaugca ggcuucaugg   3960
cccaaagugg aacaauuuug gggccagacac auguggaacu cauuagcgg cauccaauac   4020 cucgcaggau ugucaacacu gccagggaac ccgcgguggg cuuccaugau ggcauucagu   4080
gccgcccuca ccagnccguu gucgaccagn accaccaucc uucucaacau caugggaggc   4140
ugguuagcgu cccagaucgc accacccgcg ggggccaccg gcuuugucgu cagnggccug   4200
gugggggcug ccgugggcag cauaggccug gguaaggugc ugguggacau ccuggcagga   4260
uauggugcgg gcauuucggg ggcccucguc gcauucaaga ucaugncugg cgagaagccc   4320
ucuauggaag augucaucaa ucuacugccu ggauccugu uccgggagc ccuggnggug   4380 ggggucaucu gcgcggccau ucugcgccgc cacgugggac cggggagggg cgcggnccaa   4440
uggaugaaca ggcuuauugc cuugcuucc agaggaaacc acgucgcccc uacucacuac   4500 gugacgagu cggaugcguc gcagcgngug acccaacuac uggcucucu uacuauaacc   4560 agccuacuca gaagacncca caauuggaua acugaggacu gccccauccc augcuccgga   4620
uccuggcucc gcgacgugug ggacugggnu ugcaccaucu ugacagacuu caaaaauugg   4680
cugaccucua aauuguccc caagcugccc ggccuccccu ucaucucunug ucaaaagggg   4740 uacaagggug uggggccgg cacuggcauc augaccacgc gcugcccuug cggcgccaac   4800
aucucuggca auguccgccu gggcucuaug aggaucacag ggccuaaaac cugcaugaac   4860
accuggcagg ggaccuuucc uaucaauugc uacacggagg ccagugcgc gccgaaaccc   4920 cccacgaacu acaagaccgc caucuggagg guggcggccu cggaguacgc ggagugacg   4980 cagcaugggu cguacuccua uguaacagga cugaccacug acaaucugaa aauuccuugc   5040
caacuaccuu cuccagaguu uuucuccugg guggacggug ugcagauccna uagguuugca   5100 cccacaccaa agccgunuuu ccgggaugag ucucguucu gcguugggcu uaauuccuau   5160
gcugucgggu cccagcuucc cugugaaccu gagcccgacg cagacguauu gaggnccaug   5220
cuaacagauc cgccccacau cacggcggag acucggcgc ggcgcuuggc acggggauca   5280
ccuccaucug aggcgagcuc ucagngagc cagcuaucag caccgucgcu gcgggccacc   5340 ugcaccacccc acagcaacac cuaugacgng gacauggucg augccaaccu gcucauggag   5400
ggcggugngg cucagacaga gccugagncc agggngcccg uucgggacuu ucucgagcca   5460
auggccgagg aagagagcga ccuugagccc ucaauaccau cggagugcau gccccccagg   5520 agcgggnuuuc cacgggccuu accgcuuugg gcacggccug acuacaaccc gccgcucgug   5580
gaaucgugga ggaggccaga uuaccaaccg cccaccguug cuggnugugc cuccccccc   5640 cccaagaagg ccccgacgcc ucccccaagg agacgccgga cagngggucu gagcgagagc   5700
accauaucag aagcccucca gcaacuggcc aucaagaccu uggccagcc ccccucgagc   5760 ggugaugcag gcucguccac ggggcgggc gccgccgaau ccggcggucc gacgucccu   5820 ggugaccggg cccccucaga cagguuccg gccuccucua ugcccccccu cgaggggggag   5880 ccuggagauc cggaccugga gucugaucag guagagcuuc aaccucccc cagggggggg   5940 ggguuagcuc ccgguucggg ucggggucu ugguucnacuu gcuccgagga ggacganacc   6000 accgugucgcu gccccaugic auacuccugg accgggcuc uaauaacucc cuguagcccc   6060
gaagaggaaa aguugccnau caaccccuunug aguaacucgc guugcgauia ccauiaacaag   6120 guguacugua caacaucaaa gagcgcccuca cagagggcua aaaagguaac uuuugacagg   6180
```

```
acgcaagugc ucgacgccca uuaugacuca gucuuaaagg acaucaagcu agcggcuucc    6240
aaggucagcg caaggcuccu caccuuggag gaggcgugcc aguugacucc accccauucu    6300
gcaagaucca aguauggauu cggggccaag gaggucagca gcuugccggg agggccguu    6360
aaccacauca aguccgugug aaggaccuc cuggaagacc acaaacacc aauucccaca      6420
accaucaugg ccaaaaauga ggguucugc guggaccccg ccaagggggg uaagaaacca     6480
gcucgccuca ucguuuaccc ugaccucggc guccgggucu gcgagaaaau ggcccucuau    6540
gacauuacac aaaagcuucc ucaggcggua auggggagcuu ccuauggcuu ccaguacucc   6600
ccugcccaac ggguggagua ucucuugaaa gcaugggcgg aaaagaagga ccccaugggu    6660
uuucguaug auacccgaug cuucgacuca accgucacug agagagacau caggaccgag     6720
gagucauau accaggccug cucccugccc gaggaggccc gcacgccau acacucgcug      6780
acugagagac uuuacguagg agggcccau uucaacagca agggucaaac cugcgguuac     6840
agacguugcc gcgccagcgg ggugcuaacc acuagcaugg guaacaccau cacaugcuau    6900
gugaaagccc uagcggccug caaggcgcg gggauaguug cgcccacaau gcugguaugc     6960
ggcaaugacc uaguagucau cucagaaagc cagggacug aggaggacga gcggaaccug     7020
agagccuuca cggaggccau gaccagguac ucugcccuc cuggugaucc ccccagaccg    7080
gaauaugacc uggagcuaau aacauccugu uccucaaaug ugucuggc guugggcccg      7140
cggggccgcc gcagauacua ccugaccaga gacccaacca uccacucgc ccgggcugcc    7200
ugggaaacag uuagcacuc cccuaucaau ucauggcugg gaaacaucau ccaguaugcu    7260
ccaaccauau ggguucgcau ggccuaaug acacacuucu ucuccauucu caugguccaa   7320
gacacccugg accagaaccu caacuuugag auguauggau caguauacuc cgugaauccu  7380
uuggaccuuc cagccauaau ugagagguua cacgggcuug acgccuuuuc uaugcacaca  7440
uacucucacc acgaacugac gcggguggcu ucagcccuca gaaaacuugg ggcgccaccc   7500
cucaggugu ggaagagucg ggcucgcgca gucagggcgu cccucaucuc ccguggaggg   7560
aaagcggccg uuugcggccg auaucucuuc aauugggcgg ugaagaccaa gcucaaacuc  7620
acuccauugc cggaggcgcg ccuacuggac uuauccaguu gguucaccgu cggcgccggc  7680
gggggcgaca uuuucacag cgugucgcgc gcccgacccc gcucauuacu cuucggccua   7740
cucccuacuuu ucguagggu aggccucuuc cuacuccccg cucgguagag cggcacacac    7800
uagguacacu ccauagcuaa cuguccuuu uuuuuuuuu uuuuuuuuuu uuuuuuuuu      7860
uuuuuuuuuu cuuuuuuuuu uuuuucccuc uuucuucccu ucucaucuua uucuacuuuc   7920
uuucuugguq gcuccaucuu agcccuagcu acgcuagcu ugaaaggguc cgugagccgc   7980
augacugcag agagugccgu aacggcucuc ucugcagauc augu                  8024
```

<210> SEQ ID NO 8
<211> LENGTH: 7994
<212> TYPE: RNA
<213> ORGANISM: Artificial Sequence
<220> FEATURE:
<223> OTHER INFORMATION: HCV-derived synthetically created replicon RNA
      rSGREP-JFH1/dGDD

<400> SEQUENCE: 8

```
accugcccu aauaggggcg acacuccgcc augaaucacu ccccugugag gaacuacugu      60
cuucacgcag aaagcgccua gccauggcgu uaguaugagu gucguacagc cuccaggccc    120
ccccucccg ggagagccau aguggucugc ggaaccggug aguacaccgg aauugccggg    180
```

```
aagacuggguccuuucuuggauaaacccacucuaugcccggccauuugggcgugcccccg      240 caagacugcuagccgaguagcguuggguugcgaaaggccuuguggacugccugauaggg       300 cgcuugcgagugccccgggaggucucguagaccgugcaccaugagcacaaauccuaaacc     360 ucaaagaaaaaccaaagaaacaccaaccgucgcccaaugauugaacaaguggauugca       420 cgcagguucuccggccgcuuggguggagagcauuucggcuaugacugggcacaacagac     480 aaucggcugcucugaugccgccguguuccgcugucagcgcaggggcgccgguucuuuu      540 ugucaagaccgaccugucggugcccugaaugaacugcaggacgaggcagcgcggcuauc    600 guggcuggccacgacgggcguuccuugcgcagcugugcucgacguugucacugaagcggg   660 aagggacuggcugcuauuggcgcgaaagugccggggcaggaucuccugucaucucaccuugc  720 uccugccgagaaaguauccaucauggcugaugcaaugcggcggcugcauacgcuugaucc   780 ggcuaccugcccauucgaccaccaagcgaaacaucgcaucgagcgagcacguacucggau   840 ggaagccgguccuugcgaucaggaugaucuggacgaagagcaucaggggcucgcgccagc   900 cgaacuguucgccaggcucaaggcgcgcaugcccgacggcgaggaucucgucugaccca    960 uggcgaugccugcuugccgauaucauggugggaaaauggccgcuuuucugauucaucga   1020 cuguggccggcugggugugcggaccgcuaucaggacauagcguuggcuacccgugauau   1080 ugcugaagagcuuggcggcgaaugggcugaccgcuuccucgugcuuuacguaucgccgc   1140 ucccgauucgcagcgcaucgccuucuaucgccuucuugacgaguucuucugaguuuaaac  1200 ccucuccccuccccccccuaacguuacggccgaagccgcuuggaauaaggccggugug    1260 cguuugucuauauguuauuuuccaccauaugccgucuuuuggcaaugugagggcccgga   1320 aaccuggcccugucuucuugacgagcauucuaggggcuuuccccucucgccaaaggaa    1380 ugcaaggucuguugaaugucgugaaggaagcaguccucuggaagcuucugaagacaaa    1440 caacgcucguagcgacccuugcaggcagcggaaccccccaccugcgacaggugccucu    1500 gcggccaaaagccacguguaaagauacacgcugcaaaggcggcacaaccccagugccacg   1560 uugugaguugauaguguguggaaagagucaaauggcucuccucaagcguauucaacaagg  1620 ggcugaaggaugcccagaaggguaccccauuguaugggaucugaucggggccucggugca  1680 caugcuuuacauguguuuagucgagguuaaaaaacgucuaggccccccgaaccacgggg   1740 acgugguuuuccuuugaaaaacacgaugauaccauggcuccaucacugcuuaugcccag   1800 caaacacgaggccuccugggcgccauaguggugaguaugacggggcgugacaggacagaa   1860 caggccgggaaguccaaauccuguccacagucucucaguccuuccucggaacaaccauc   1920 ucggggguuuuguggacuguuuaccacggagcuggcaacaagacucuagccggcuuacgg   1980 gguccgucacgcagauguacucgagugcugaggggacuugguaggcugcccagcccc     2040 ccugggaccaagucuuuggagccgugcaaguguggagccgucgaccauaucuggucacg   2100 cggaacgcugaugucaucccggcucggagacgcggggacaagcggggagcauugcucucc   2160 ccgagacccauuucgaccuugaaggggucucgggggccgguggcucugcccuagggggc    2220 cacgucguugggcucuuccgagcagcuguguggcucgggggcguggccaauauccaucgau  2280 uucauccccguugagacacucgacguuguuacaaggucucccacuuucagugacaacagc  2340 acgccaccggcugugccccagaccuaucaggucgggacugcaugcucccaacuggcagu   2400 ggaaagagccaaggucccguugcgcguaugccgcccaggaguacaaagaucuagugcuu  2460 aaccccucgguagcugccaccccuggggguuuggggcguaccuauccaaggcacauggcauc   2520 aaucccaacauuaggacugagucaggaccgugaugaccggggaggccaucacguacucc   2580
```

```
acauauggca aauuucucgc cgaugggggc ugcgcuagcg gcgccuauga caucaucaua   2640
ugcgaugaau gccacgcugu ggaugcuacc uccauucucg gcaucggaac gguccuugau   2700
caagcagaga cagccggggu cagacuaacu gugcuggcua cggccacacc ccccgggucu   2760
gugacaaccc cccaucccga uauagaagag guaggccucg ggcgggaggg ugagauccccc  2820 uucuauggga gggcgauucc ccuauccugc aucaaggag ggagacaccu gauuucugc    2880 cacucaaaga aaaagugga cgagcucgcg gcggcccuuc ggggcauggg cuugaaugcc   2940
guggcauacu auagagggu ggacgucucc auaauaccag cucagggaga gugguggu   3000 gucgccaccg acgcccucau gacggggauc acuggagacu uugacuccgu gaucgacugc   3060 aaauguagcgg ucacccaagc ugucgacuuc agccuggacc ccaccuucac uauaaccaca   3120 cagacuguc cacaagacgc ugucucacgc agucagcgcc gcgggcgcac agguagagga   3180
agacagggca cuuauaggua uguuccacu ggugaacgag ccucaggaau guuugacagu   3240
guagugcuuu gugagugcua cgacgcaggg gcugcggu acgaucucac accagcggag   3300
accaccguca ggcuuagagc guauuucaac acgcccggcc uacccgugug ucaagaccau   3360 cuugaauuu gggaggcagu uuucaccggc cucacacaca uagacgccca cuuccucucc   3420
caaacaaagc aagcgggga gaacuucgcg uaccuaguag ccuaccaagc uacggugugc   3480
gccagagcca aggcccccucc cccgugcugg gacgccaugu ggaagugccu ggcccgacuc   3540
aagccuacgc uugcgggccc cacaccucuc cuguaccguu ugggcccuau uaccaaugag   3600
gucacccuca cacaccuugg gacgaaguac aucgccacau gcaugcaagc ugaccuugag   3660
gucaugacca gcacgugggu ccuagcugga ggagucucug cagccgucgc cgcauauugc   3720
cuggcgacug gaugcguuuc caucaucggc cgcuugcacg ucaaccagcg agucgucguu   3780
gcgccggaua aggagguccu guaugaggcu uuugaugaga uggaggaaug cgccucuagg   3840
gcggcucuca ucgaagaggg gcagcggaua ccgagaugu ugaaguccaa gauccaaggc   3900
uugcugcagc aggccucuaa gcaggccag gacauacaac ccgcuaugca ggcuucaugg   3960
cccaaagugg aacaauuuug gccagacac auguggaacu caauagcgg cauccaauac   4020 cucgcaggau ugucaacacu gccagggaac cccgcgugg cuccaugau ggcauucagu   4080 gccgcccuca ccaguccguu gucgaccagu accaccaucc uucucaacau cauggggagc   4140
ugguuagcgu cccagaucgc caccacccgcg ggggccaccg gcuuugucgu caguggccug   4200
gugggggcug ccgugggcag cauaggcccug ggggaaggugc uguggacau ccuggcagga   4260 uaugugcgg gcauuucggg ggcccucguc gcauucaaga ucaugucugg cgagaagccc   4320
ucuauggaag augucaucaa ucuacugccu gggaucccugu cuccgggagc ccuggugug   4380 gggucaucu gcgcggccau ucugcgccgc cacgugggac cggggaggg cgcgguccaa   4440 uggaugaaca ggcuuauugc cuuugcuucc agaggaaacc acgucgcccc uacucacuac   4500
gugacggagu cggaugcguc gcagcgugug acccaacuac uuggcucucu acuauaaccc   4560
agccuacuca gaagacucca caauuggaua acgaggacu gccccauccc augcuccgga   4620 uccuggcuc cgcgacgugug ggacggguu ugcaccaucu ugacagacuu caaaaauugg   4680
cugaccucua aauuguccc caagcugccc ggccucccccu ucaucucuug ucaaagggg   4740 uacaagggug uugggccgg cacuggcauc augaccacgc gcugcccuug cggcgccaac   4800
aucucuggca augccgccu ggcucuaug aggaucacag ggccuaaaac cugcaugaac   4860
accuggcagg ggaccuuucc uaucaauugc uacacgagg gccagugcgc ccgaaacccc   4920
cccacgaacu acaagaccgc caucuggagg gugggcggccu cggaguacgc ggaggugacg   4980
```

```
cagcaugggu cguacuccua uguaacagga cugaccacug acaaucugaa aauuccuugc      5040
caacuaccuu cuccagaguu uuucuccugg guggacggug ugcagaucca uagguuugca      5100
cccacaccaa agccguuuuu ccgggaugag gucucguucu gcguugggcu aauuccuau       5160 gcugucgggu cccagcuucc cugugaaccu gagcccgacg cagacguauu gagguccaug      5220
cuaacagauc cgccccacau cacggcggag acugcggcgc ggcgcuuggc acggggauca      5280
ccuccaucug aggcgagcuc cucagugagc cagcuaucag caccgucgcu gcgggccacc      5340
ugcaccaccc acagcaacac cuaugacgug gacaugguug augccaaccu gcucauggag      5400 ggcgugugg cucagacaga gccugagucc agggugcccg uucuggacuu ucucgagcca       5460
auggccgagg aagagagcga ccuugagccc ucaauaccau cggagugcau gcuccccagg      5520 agcgg guuuc cacgggccuu accggcuugg gcacggccug acuacaaccc gccgcucgug      5580
gaaucgugga ggaggccaga uuaccaaccg cccaccguug cugguuguugc ucccccccc      5640 cccaagaagg ccccgacgcc uccccaagg agacgccgga cagugggucu gagcgagagc       5700
accauaucag aagcccucca gcaacuggcc aucaagaccu uggccagcc cccucgagc        5760 ggugaugcag gcucguccac gggggcgggc gccgccgaau ccggcggucc gacgucccu       5820 ggugagccgg cccccucaga gacagguucc gccuccucua ugcccccccu cgaggggag       5880 ccuggagauc cggaccugga gucugaucag guagagcuuc aaccucccc ccaggggggg       5940 gggguagcuc ccgguucggg cucgggucu uggucuacuu gcuccgagga ggacgauacc       6000
accgugugcu gcccauguc auacuccugg accggggcuc uaauaacucc cuguagcccc       6060
gaagaggaaa aguugccaau caaccccuuug aguaacucgc uguugcgaua ccauaacaag     6120
guguacugua caaucaaa gagcgccuca cagagggcua aaaggguaac uuugacagg         6180 acgcaagugc ucgacgccca uuaugacuca gucuuuaagg acaucaagcu agcggcuucc      6240
aaggucagcg caaggcuccu caccuuggag gaggcgugcc aguugacucc accccauucu      6300
gcaagaucca aguauggauu cggggccaag gaggucccgca gcuugccgg gagggccguu     6360 aaccacauca aguccgugug aaggacccuc cuggaagacc cacaaacacc aauucccaca      6420
accaucaugg ccaaaaauga ggu guucgc guggacccccg ccaaggggg uaagaaacca      6480 gcucgcccuca ucguuaccc ugaccucggc guccgggucu gcgagaaaau ggcccucuau       6540
gacauuacac aaaagcuucc ucaggcggua auggagcuu ccuauggcuu ccaguacucc       6600
ccugcccaac ggguggagua ucucuugaaa gcaugggcgg aaaagaagga ccccaugggu     6660 uuucguaug auacccgaug cuucgacuca ccgucacug agagagacau caggaccgag        6720
gaguccauau accaggccug cucccugccc gaggaggccc gcacugccau acacucgcug      6780
acugagagac uuuuacguagg agggcccaug uucaacagca agcgucaaac cugcgguuac     6840
agacguugcc gcgccagcgg ggugcuaacc acuagcaugg uaacaccau cacaugcuau       6900 gugaaagccc uagcggccug caaggcugcg gggauaguug cgcccacaau ucagaaaagc      6960
caggggacug aggaggacga gcgagaaccug agagccuuca cggaggccau gaccaggguac    7020 ucugcccuc cuggugaucc cccccagaccg gaaauugacc uggagcuaau aacauccugu     7080
uccucaaaug ugucugggc guuggggcccg cggggccgcc gcagauacua ccugaccaga      7140
gacccaacca cuccacucgc ccgggcugcc ugggaaacag uuagacacuc cccuaucaau      7200
ucauggcugg gaaacaucau ccaguaugcu ccaaccauau ggguucgcau ggccucaaug     7260
acacacuucu ucuccauucu cauggucaa gacacccugg accagaaccu caacuuugag      7320
auguauggau caguauacuc cguugaauccu uuggaccuuuc cagccauaau ugagagguua    7380
```

-continued

```
cacgggcuug acgccuuuuc uaugcacaca uacucucacc acgaacugac gcggguggcu    7440
ucagcccuca gaaaacuugg ggcgccaccc cucagggugu ggaagagucg ggcucgcgca    7500
gucagggcgu cccucaucuc ccguggaggg aaagcggccg uuugcggccg auaucucuuc    7560
aauugggcgg ugaagaccaa gcucaaacuc acuccauugc cggaggcgcg ccuacuggac    7620
uuauccaguu gguucaccgu cggcgccggc gggggcgaca uuuuucacag cgugucgcgc    7680
gcccgacccc gcucauuacu cuucggccua ccuacuuu ucguaggggu aggcucuuc      7740 cuacuccccg cucgguagag cggcacacac uagguacacu ccauagcuaa cguuccuuu    7800 uuuuuuuuuu uuuuuuuuuu uuuuuuuuuu uuuuuuuuuu cuuuuuuuuu uuuucccuc    7860 uuucuuccu ucucaucuua uucuacuuuc uuucuuggug gcuccaucuu agcccuaguc   7920
acggcuagcu gugaaaagguc cgugagccgc augacugcag agagugccgu aacuggucuc   7980
ucugcagauc augu                                                      7994

<210> SEQ ID NO 9
<211> LENGTH: 340
<212> TYPE: RNA
<213> ORGANISM: Artificial Sequence
<220> FEATURE:
<223> OTHER INFORMATION: Description of Artificial Sequence: synthetic
      RNA

<400> SEQUENCE: 9
accugccccu aauagggggcg acacuccgcc augaaucacu ccccgugag gaacuacugu     60 cuucacgcag aaagcgccua gccauggcgu uaguaugagu gucguacagc cuccaggccc    120
cccccucccg ggagagccau aguggucugc ggaaccggug aguacaccgg aauugccggg    180
aagacugggu ccuuucuugg auaaacccac ucuaugcccg gccauuuggg cgugccccg     240 caagacugcu agccgaguag cguuggguug cgaaaggccu uguggguacug ccugauaggg    300 cgcuugcgag ugccccggga ggucucguag accgugcacc                          340

<210> SEQ ID NO 10
<211> LENGTH: 340
<212> TYPE: RNA
<213> ORGANISM: Artificial Sequence
<220> FEATURE:
<223> OTHER INFORMATION: Description of Artificial Sequence: synthetic
      RNA

<400> SEQUENCE: 10
acccgccccu aauagggggcg acacuccgcc augaaucacu ccccgugag gaacuacugu     60 cuucacgcag aaagcgucua gccauggcgu uaguaugagu gucguacagc cuccaggccc    120
cccccucccg ggagagccau aguggucugc ggaaccggug aguacaccgg aauugccggg    180
aagacugggu ccuuucuugg auaaacccac ucuaugcccg gccauuuggg cgugccccg     240 caagacugcu agccgaguag cguuggguug cgaaaggccu uguggguacug ccugauaggg    300 ugcuugcgag ugccccggga ggucucguag accgugcacc                          340

<210> SEQ ID NO 11
<211> LENGTH: 236
<212> TYPE: RNA
<213> ORGANISM: Artificial Sequence
<220> FEATURE:
<223> OTHER INFORMATION: Description of Artificial Sequence: synthetic
      RNA

<400> SEQUENCE: 11
agcggcacac acuagguaca cuccauagcu aacuguuccu uuuuuuuuuu uuuuuuuuuu     60
```
uuuuuuuuuu uuuuuuuuuu uucuuuuuuu uuuuuuuccc ucuuucuucc cuucucaucu    120
uauucuacuu ucuuucuugg uggcuccauc uuagcccuag ucacggcuag cugugaaagg    180
uccgugagcc gcaugacugc agagagugcc guaacugguc ucucugcaga ucaugu        236

```
<210> SEQ ID NO 12
<211> LENGTH: 232
<212> TYPE: RNA
<213> ORGANISM: Artificial Sequence
<220> FEATURE:
<223> OTHER INFORMATION: Description of Artificial Sequence: synthetic
      RNA

<400> SEQUENCE: 12
```
agcggcacac auuagcuaca cuccauagcu aacuguuccu uuuuuuuuuu uuuuuuuuuu     60
uuuuuuuuuu uuuuuucuu uuuuuuuuuu uucccucuu ucuucccuuc ucaucuuauu    120
cuacuuucuu ucugguggc uccaucuuag cccuggucac ggcuagcugu gaaagguccg    180
ugagccgcau gacugcagag agugccguaa cugguccucuc ugcagaucau gu          232

```
<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 13
```
cgggagagcc atagtgg                                                   17

```
<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 14
```
agtaccacaa ggcctttcg                                                 19

```
<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 15
```
ctgcggaacc ggtgagtaca c                                              21

```
<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 16
```
aacaagatgg attgcacgca                                                20

```
<210> SEQ ID NO 17
```

```
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 17
cgtcaagaag gcgatagaag                                                     20

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 18
gcactctctg cagtcatgcg gctcacggac                                          30

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 19
cccctgtgag gaactactgt cttcacgc                                            28

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 20
ccgggagagc catagtggtc tgcg                                                24

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 21
ccactcaaag aaaaagtgtg acgagctcgc                                          30

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 22
ggcttgggca cggcctga                                                       18

<210> SEQ ID NO 23
<211> LENGTH: 30
<212> TYPE: DNA
```

```
<213> ORGANISM: Artificial Sequence
<220> FEATURE:
<223> OTHER INFORMATION: Description of Artificial Sequence: synthetic
      DNA

<400> SEQUENCE: 23
gcggtgaaga ccaagctcaa actcactcca                                        30

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 24
agaacctgcg tgcaatccat c                                                 21

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 25
cccgtcatga gggcgtcggt ggc                                               23

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 26
accagcaacg gtgggcggtt ggtaatc                                           27

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 27
ggcacgcgac acgctgtg                                                     18

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 28
agctagccgt gactagggct aagatggagc                                        30

<210> SEQ ID NO 29
<211> LENGTH: 20
<212> TYPE: DNA
<213> ORGANISM: Artificial Sequence
<220> FEATURE:
```

<223> OTHER INFORMATION: Description of Artificial Sequence: synthetic
      DNA(primer)

<400> SEQUENCE: 29
aacaagatgg attgcacgca                                                 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: synthetic
      DNA(primer)

<400> SEQUENCE: 30
cgtcaagaag gcgatagaag                                                 20

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 31
gcactctctg cagtcatgcg gctcacggac                                      30

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 32
cccctgtgag gaactactgt cttcacgc                                        28

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 33
ccgggagagc catagtggtc tgcg                                            24

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 34
ccactcaaag aaaaagtgtg acgagctcgc                                      30

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: synthetic
      DNA(primer)

```
<400> SEQUENCE: 35
ggcttgggca cggcctga                                          18

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 36
gcggtgaaga ccaagctcaa actcactcca                             30

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 37
agaacctgcg tgcaatccat c                                      21

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 38
cccgtcatga gggcgtcggt ggc                                    23

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 39
accagcaacg gtgggcggtt ggtaatc                                27

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 40
ggaacgcgac acgctgtg                                          18

<210> SEQ ID NO 41
<211> LENGTH: 30
<212> TYPE: DNA
```

```
<213> ORGANISM: Artificial Sequence
<220> FEATURE:
<223> OTHER INFORMATION: Description of Artificial Sequence: synthetic
      DNA

<400> SEQUENCE: 41
agctagccgt gactagggct aagatggagc                                              30
```

NUCLEIC ACID CONSTRUCT CONTAINING A NUCLEIC ACID DERIVED FROM THE GENOME OF HEPATITIS C VIRUS (HCV) OF GENOTYPE 2A, AND A CELL HAVING SUCH NUCLEIC ACID CONSTRUCT INTRODUCED THEREIN

This application is a Divisional of co-pending application Ser. No. 12/958,318 filed on Dec. 1, 2010 and for which priority is claimed under 35 U.S.C. §120. Application Ser. No. 12/958,318 is a Divisional of application Ser. No. 10/558,155, now U.S. Pat. No. 7,935,676, filed on Jan. 3, 2007. Application Ser. No. 10/558,155 is the national phase of PCT International Application No. PCT/JP2003/015038 filed on Nov. 25, 2003 under 35 U.S.C. §371 which claims priority under 35 USC §119(a)-(d) of Application No. 2003-148242 filed in Japan on May 26, 2003 and Application No. 2003-329115 filed in Japan on Sep. 19, 2003. The entire contents of each of the above-identified applications are hereby incorporated by reference.

TECHNICAL FIELD

The present invention relates to a replicon RNA of the hepatitis C virus of genotype 2a, a replicon-replicating cell wherein the replicon RNA is introduced, and a method of increasing the replication efficiency of the replicon RNA.

BACKGROUND ART

The hepatitis C virus (HCV) is a virus belonging to the family Flaviviridae. It has a single-stranded (+) strand sense RNA as its genome and is known to cause hepatitis C. Recent studies have revealed that Hepatitis C virus is classified into a number of types based on genotypes or serotypes. According to the phylogenetic analysis of Simmonds et al., using the nucleotide sequences of the HCV strains, which is currently a mainstream method of classifying HCV genotypes, HCV is classified into 6 genotypes: genotype 1a, genotype 1b, genotype 2a, genotype 2b, genotype 3a and genotype 3b (see Simmonds, P. et al, Hepatology, (1994) 10, pp. 1321-1324). Each of these types is further classified into several subtypes. The nucleotide sequences of the full-length genomes of a several number of genotypes of HCV have been determined to date (see JP Patent Publication (Kokai) No. 2002-171978 A; Choo et al., Science, (1989) 244, pp. 359-362; Kato et al., J. Med. Virol., (2001) 64(3) pp. 334-339; Okamoto, H et al, J. Gen. Virol., (1992) 73 pp. 673-679; and Mori, S. et al, Biochem. Biophis. Res. Commun., (1992) 183, pp. 334-342).

HCV causes chronic hepatitis by persistent infection. Currently, the main cause of chronic hepatitis observed worldwide is persistent HCV infection. Actually, around 50% of individuals with persistent infection develop chronic hepatitis. Chronic hepatitis in approximately 20% of these patients shifts to liver cirrhosis over the course of 10 to 20 years, and some of these patients further go on to advanced lethal pathological conditions such as hepatic cancer.

Hepatitis C is currently treated mainly by a therapy using interferon-α or interferon-β, or a therapy using in combination interferon-α and ribavirin, the purine-nucleoside derivative. However, even when these therapies are performed, the therapeutic effects are observed in only approximately 60% of all the treated patients. When the therapies are ceased after the exertion of the effects, the disease recrudesces in more than half of the patients. The therapeutic effect of interferones is known to relate to HCV genotypes, and is said to be lower against genotype 1b and higher against genotype 2a (see Yoshioka et al., Hepatology, (1992) 16(2): pp. 293-299).

It is an important goal to develop therapeutic agents or prophylactic agents effective against hepatitis C, the incidence rate of which is high in industrial countries, for which currently no causal treatment are present, and which finally bring about serious results. Hence, the development of HCV-specific chemotherapies and vaccine therapies are earnestly desired. A target for the development of an anti-HCV agent may be the suppression of HCV replication or the suppression of infection of cells with HCV.

Until recently, propagation of HCV in a cell culture system and infecting cultured cells with HCV have been difficult. Moreover, a chimpanzee has been the only animal that can be infected with HCV and can be used in experiments, so that it has been difficult to carry out studies on the replication mechanism of HCV and the infection mechanism of HCV. However, recently, HCV subgenomic RNA replicons have been prepared as HCV-derived autonomously replicable RNA (see JP Patent Publication (Kokai) No. 2001-17187 A; Lohmann et al., Science, (1999) 285, pp. 110-113; Blight et al., Science, (2000) 290, pp. 1972-1974; Friebe et al., J. Virol., (2001) 75(24): pp. 12047-12057; Ikeda et al., J. Virol., (2002) 76(6): pp. 2997-3006), which enables the analysis of the replication mechanism of HCV using cultured cells. These HCV subgenomic RNA replicons are each prepared by substituting structural proteins existing downstream of HCV IRES in the 5' untranslated region of the HCV genomic RNA of genotype 1b with a neomycin resistance gene and EMCV IRES that has been ligated downstream of the resistance gene. It has been demonstrated that this RNA replicon is autonomously replicated in human hepatic cancer cells, Huh7 cells, when introduced into the Huh7 cells followed by culture in the presence of neomycin.

However, regarding such intracellular RNA replication systems for HCV, only those using HCV genomic RNA of genotype 1b have been prepared so far. Since there has been a report that different genotypes of HCV differ also in viral proteins encoded, it may be difficult to sufficiently elucidate the replication mechanism of HCV only by analyzing the subgenomic RNA replicons derived from HCV of genotype 1b. Furthermore, based on the fact that the therapeutic effects of interferons differ depending on the HCV genotypes, it may be particularly difficult to develop an anti-HCV agent having an effect on various types of HCV by the use of only an HCV replication system containing the subgenomic RNA replicon of HCV of genotype 1b.

SUMMARY OF THE INVENTION

The contents of Japanese Patent Application Nos. 2003-148242 and 2003-329115, from which the present application claims priority, are incorporated herein.

An object of the present invention is to provide an HCV-derived replicon RNA of a HCV genotype for which replicon RNA has not yet been prepared.

As a result of intensive studies to achieve the above object, we have succeeded in preparing the replicon RNA of HCV genotype 2a.

That is, the present invention is as follows.

[1] A replicon RNA, comprising a nucleotide sequence containing at least the 5' untranslated region, the nucleotide sequence encoding NS3 protein, NS4A protein, NS4B protein, NS5A protein and NS5B protein and the 3' untranslated region on the genomic RNA of hepatitis C virus of genotype 2a. Preferably, this replicon RNA further contains at least one selection marker gene or a reporter gene, and at least one IRES sequence.

[2] A replicon RNA, comprising a nucleotide sequence containing the 5' untranslated region comprising the nucleotide sequence represented by either SEQ ID NO: 9 or 10; at least one selection marker gene or a reporter gene; an IRES sequence; the nucleotide sequence encoding NS3 protein, NS4A protein, NS4B protein, NS5A protein and NS5B protein on the genomic RNA of hepatitis C virus of genotype 2a; and the 3' untranslated region comprising the nucleotide sequence represented by either SEQ ID NO: 11 or 12.

[3] The replicon RNA of [1] or [2] above, wherein the genomic RNA of hepatitis C virus of genotype 2a is an RNA comprising the nucleotide sequence represented by SEQ ID NO: 3 or 5.

[4] A replicon RNA, comprising the following RNA (a) or (b):
(a) an RNA comprising the nucleotide sequence represented by SEQ ID NO: 1 or 2; and
(b) an RNA comprising a nucleotide sequence derived from the nucleotide sequence represented by SEQ ID NO: 1 or 2 by deletion, substitution or addition of 1 to 10 nucleotides, and being capable of autonomous replication.

[5] A replicon-replicating cell, which is prepared by introducing the replicon RNA of any one of [1] to [4] above into a cell. For this replicon-replicating cell, a cell into which the replicon RNA is introduced is preferably a eukaryotic cell, more preferably a human liver-derived cell, a human uterine cervix-derived cell or a human fetal kidney-derived cell, and further more preferably any one cell selected from the group consisting of an Huh7 cell, an HepG2 cell, an IMY-N9 cell, an HeLa cell and a 293 cell.

[6] The replicon RNA of [1] to [4] above, which is for producing or evaluating a therapeutic agent or a diagnostic agent against hepatitis C virus infection.

[7] The replicon-replicating cell of [5] above, which is for producing or evaluating a therapeutic agent or a diagnostic agent against hepatitis C virus infection.

[8] The replicon RNA of [1] to [4] above, which is for producing a vaccine against hepatitis C virus infection.

[9] The replicon-replicating cell of [5] above, which is for producing a vaccine against hepatitis C virus infection.

[10] A method of producing a replicon RNA of hepatitis C virus of genotype 2a, comprising extracting the replicon RNA from the replicon-replicating cell of [5] above.

[11] A method of producing a viral protein of hepatitis C virus of genotype 2a, comprising culturing the replicon-replicating cell of [5] above, and obtaining the viral protein from the resulting culture product.

[12] A method of screening for a substance promoting or suppressing the replication of hepatitis C virus, comprising culturing the replicon-replicating cell of [5] above in the presence of a test substance, and detecting the replication of a replicon RNA in the resulting culture product.

[13] A method of increasing the replication efficiency of the replicon RNA of hepatitis C virus of genotype 2a, comprising performing once or more the following: obtaining a replicated replicon RNA from the replicon-replicating cell of [5] above, and introducing the thus obtained replicated replicon RNA into a cell that is different from the replicon-replicating cell so as to prepare a new replicon-replicating cell. In this method, it is more preferred that the replication efficiency increases to become preferably at least two times greater than that of the replicon RNA that is introduced at the beginning into the replicon-replicating cell.

[14] A method of producing a replicon RNA of hepatitis C virus of genotype 2a having increased replication efficiency, comprising performing once or more the following: obtaining a replicated replicon RNA from the replicon-replicating cell of [5] above, and introducing the thus obtained replicated replicon RNA into a cell that is different from the replicon-replicating cell so as to prepare a new replicon-replicating cell; and obtaining a replicated replicon RNA from the finally obtained replicon-replicating cell.

[15] A method of producing a replicon RNA of hepatitis C virus of genotype 2a having increased replication efficiency, comprising detecting a nucleotide mutation or an amino acid mutation between the replicon RNA that is produced so as to have an increased replication efficiency by the method of [14] above and the replicon RNA that is introduced at the beginning into the replicon-replicating cell; and introducing the thus detected nucleotide mutation or amino acid mutation into a replicon RNA whose replication efficiency is to be increased.

[16] A replicon RNA, comprising a nucleotide sequence derived from the nucleotide sequence represented by SEQ ID NO: 1 by at least one mutation selected from the group consisting of the following (a) to (u):
(a) a mutation from A to G at nucleotide site 7157;
(b) a mutation from C to U at nucleotide site 4955;
(c) a mutation from A to G at nucleotide site 4936;
(d) a mutation from A to G at nucleotide site 5000;
(e) a mutation from A to G at nucleotide site 7288;
(f) a mutation from G to U at nucleotide site 5901;
(g) a mutation from A to U at nucleotide site 6113;
(h) a mutation from A to G at nucleotide site 2890;
(i) a mutation from C to A at nucleotide site 6826;
(j) a mutation from C to A at nucleotide site 6887;
(k) a mutation from U to A at nucleotide site 6580;
(l) a mutation from U to C at nucleotide site 7159;
(m) a mutation from U to A at nucleotide site 7230;
(n) a mutation from C to A at nucleotide site 6943;
(o) a mutation from G to A at nucleotide site 5687;
(p) a mutation from A to G at nucleotide site 6110;
(q) a mutation from U to C at nucleotide site 5550;
(r) a mutation from A to G at nucleotide site 7217;
(s) a mutation from A to G at nucleotide site 3643;
(t) a mutation from G to A at nucleotide site 5851; and
(u) a mutation from G to A at nucleotide site 5914.

According to the present invention, an HCV-RNA replicon derived from the genotype 2a strain of HCV has been provided for the first time. The replicon-replicating cell according to the present invention can be used as a culture system for the continuous production of RNA and HCV proteins derived from HCV of genotype 2a. Furthermore, the replicon-replicating cell according to the present invention is useful as a test system for screening for various substances that affect HCV replication and/or the translation of HCV proteins.

BRIEF DESCRIPTION OF THE DRAWINGS

The patent or application file contains at least one drawing executed in color. Copies of this patent or patent application publication with color drawings will be provided by the office upon request and payment of the necessary fee.

Figure 2A:
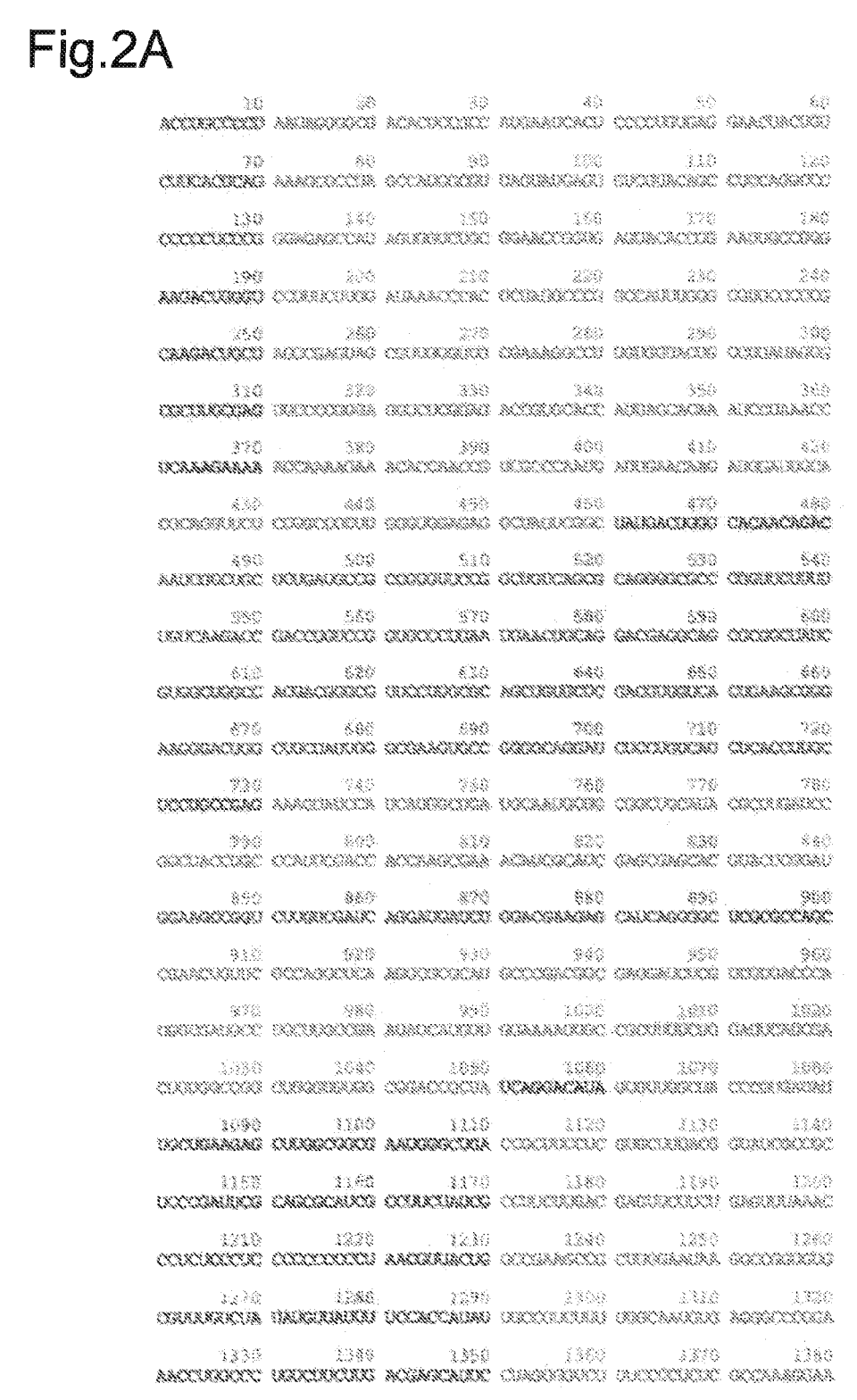
Figure 2B:
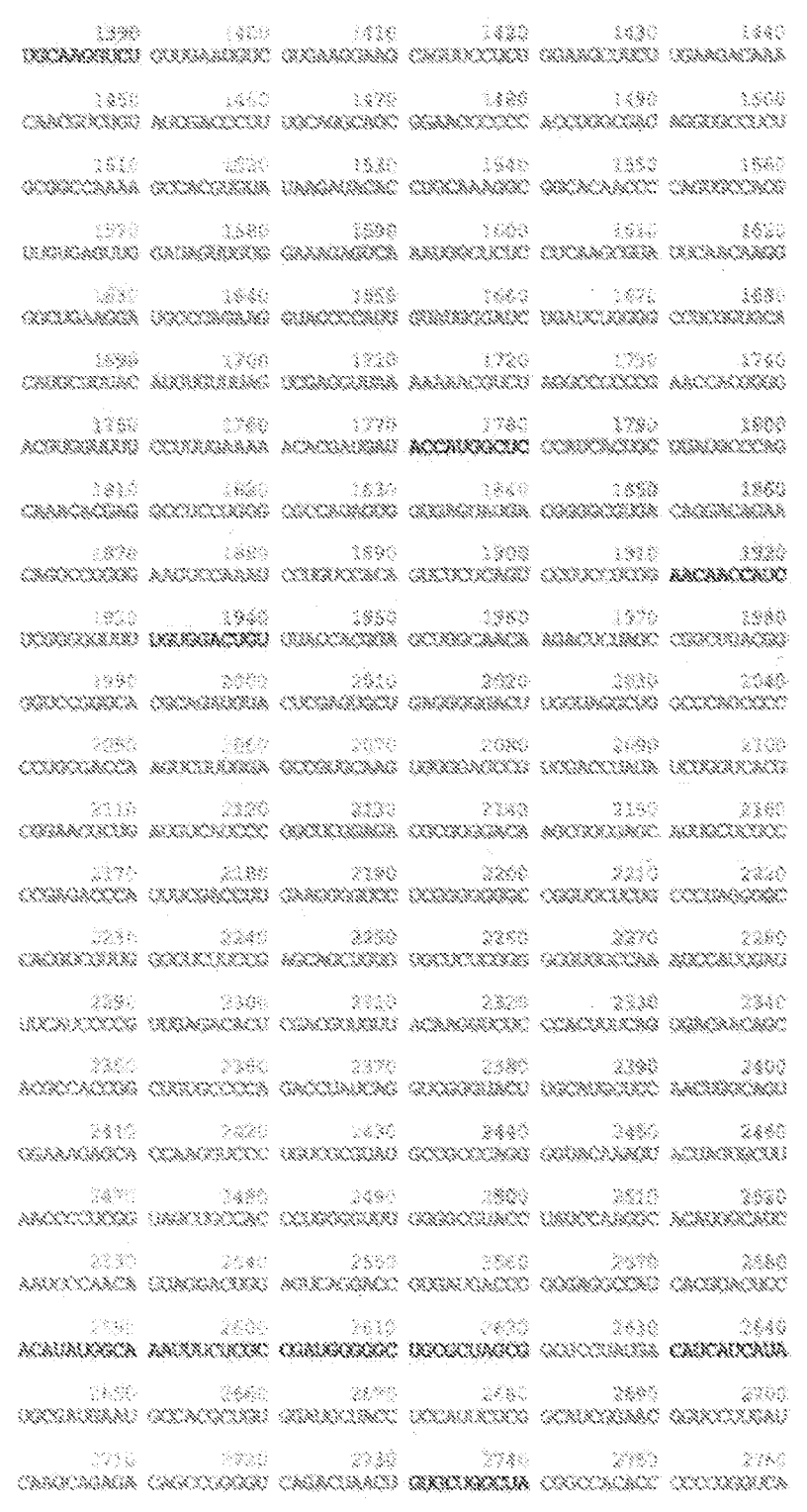
Figure 2C:
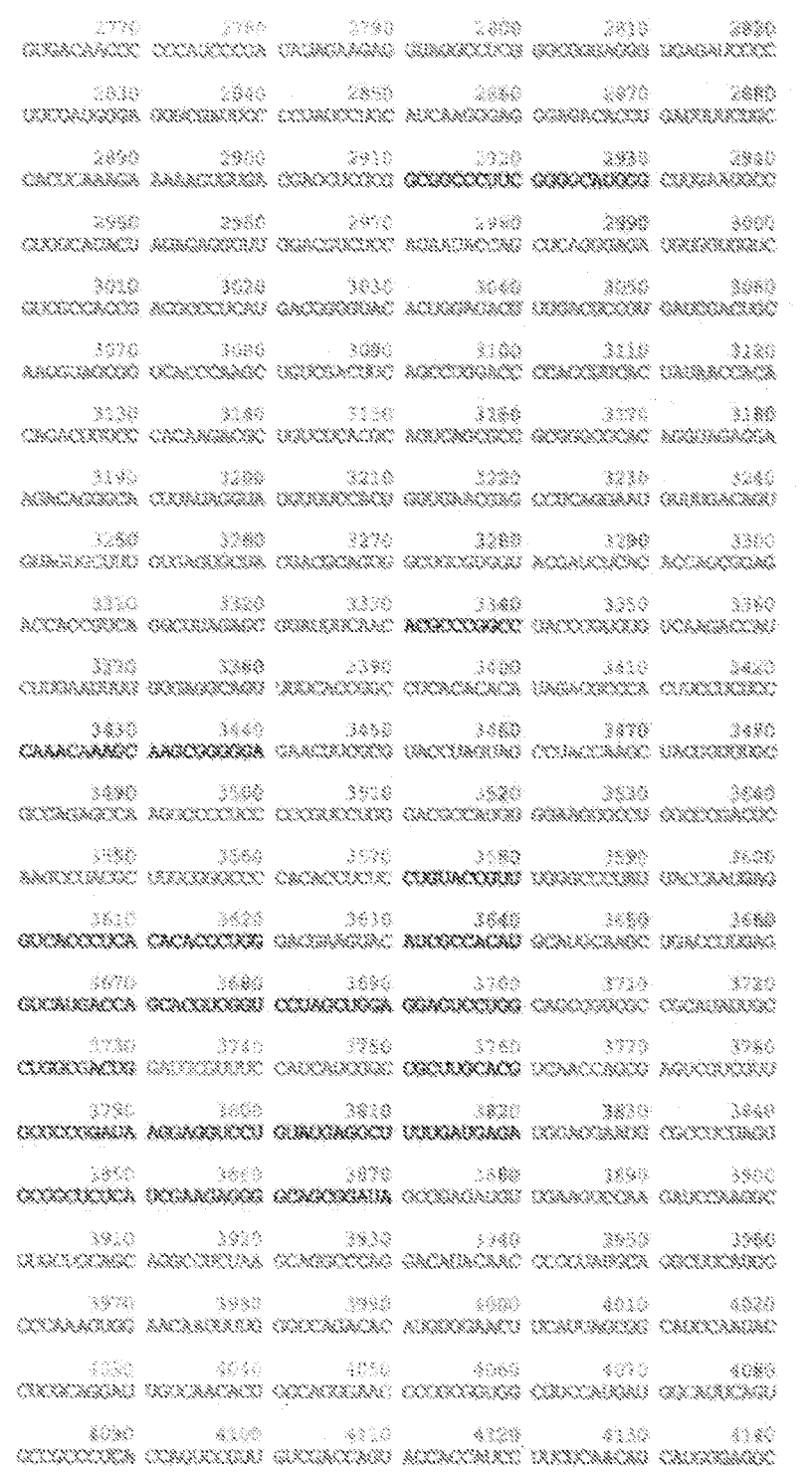
Figure 2D:
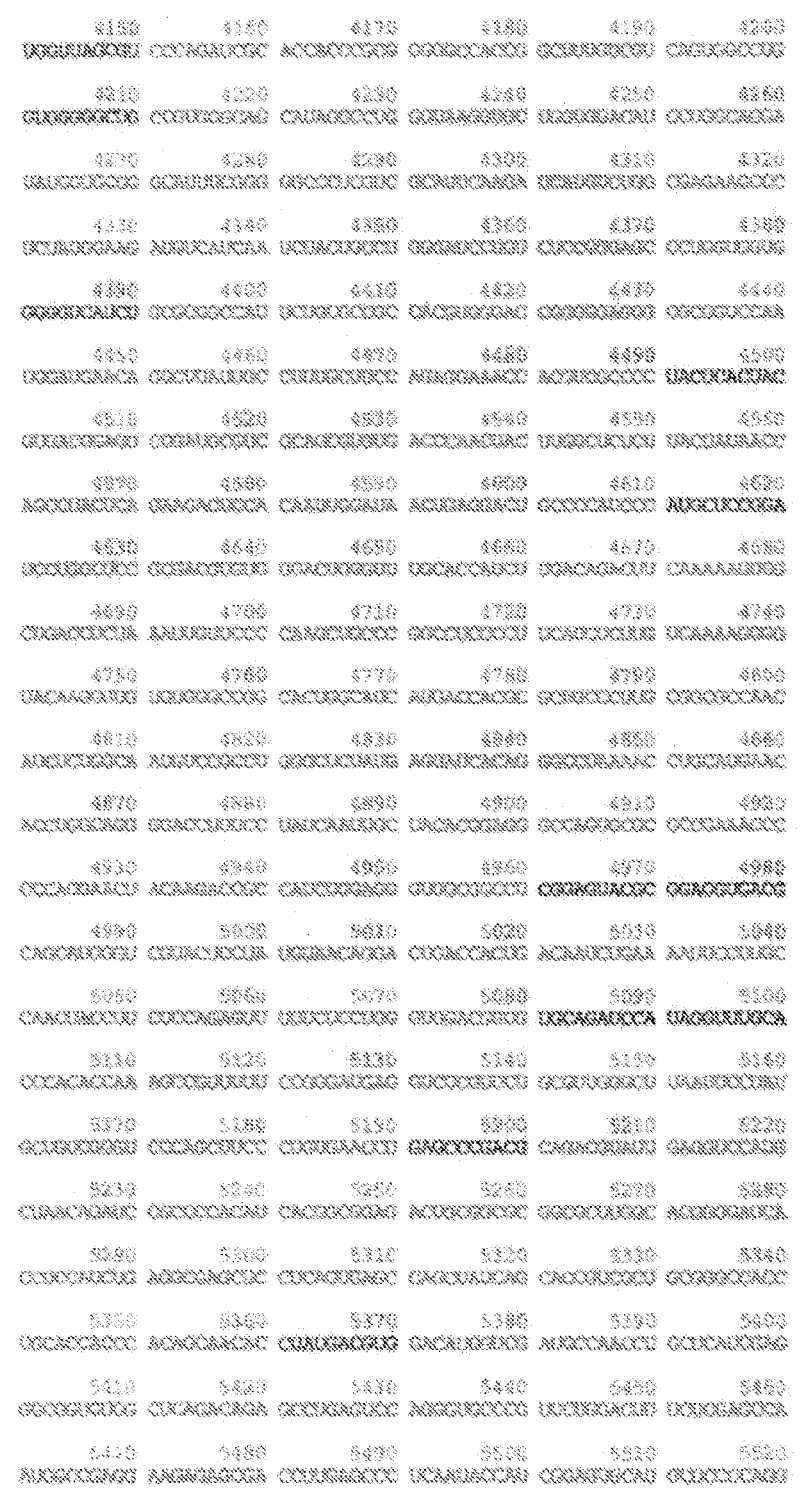
Figure 2E:
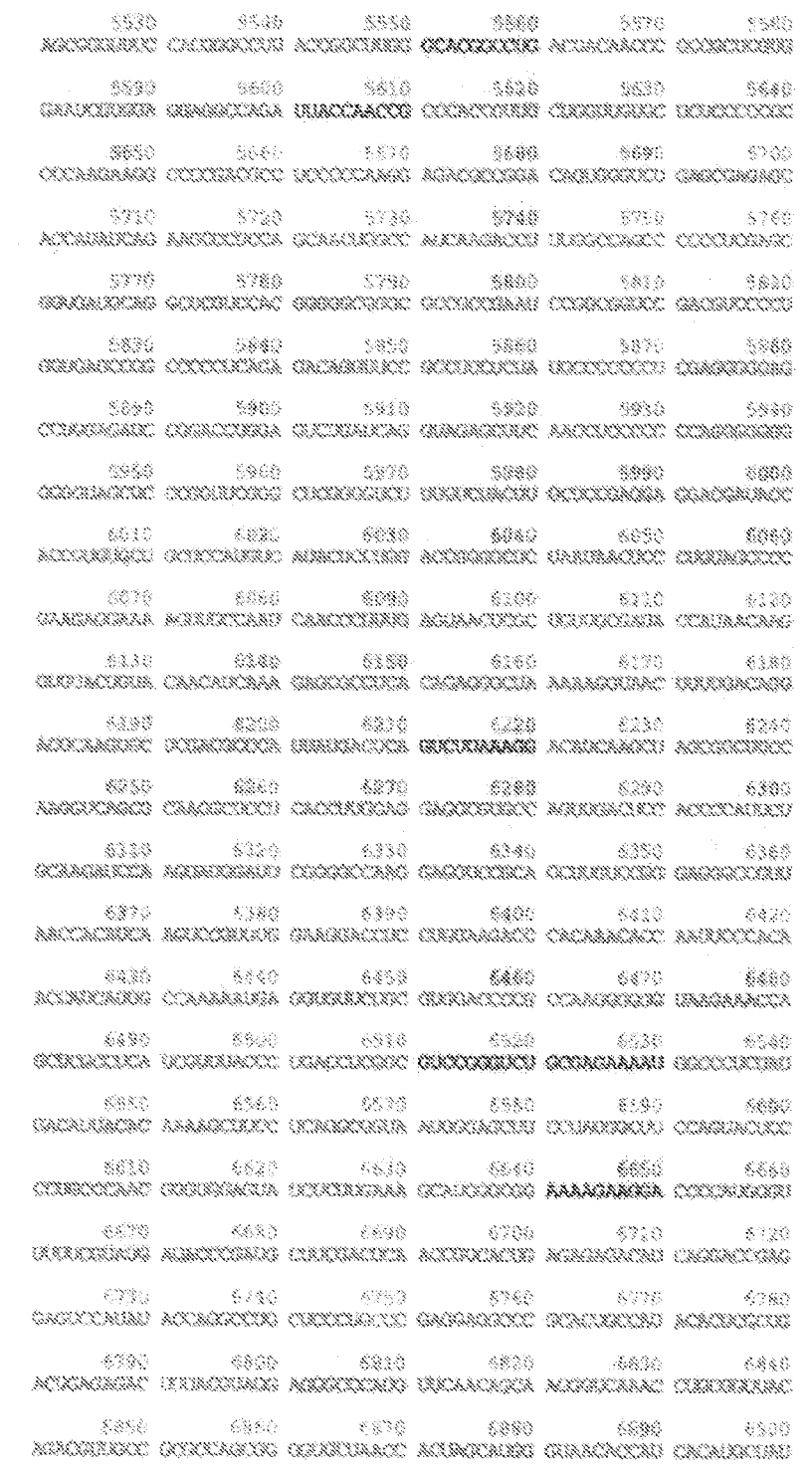
Figure 2F:
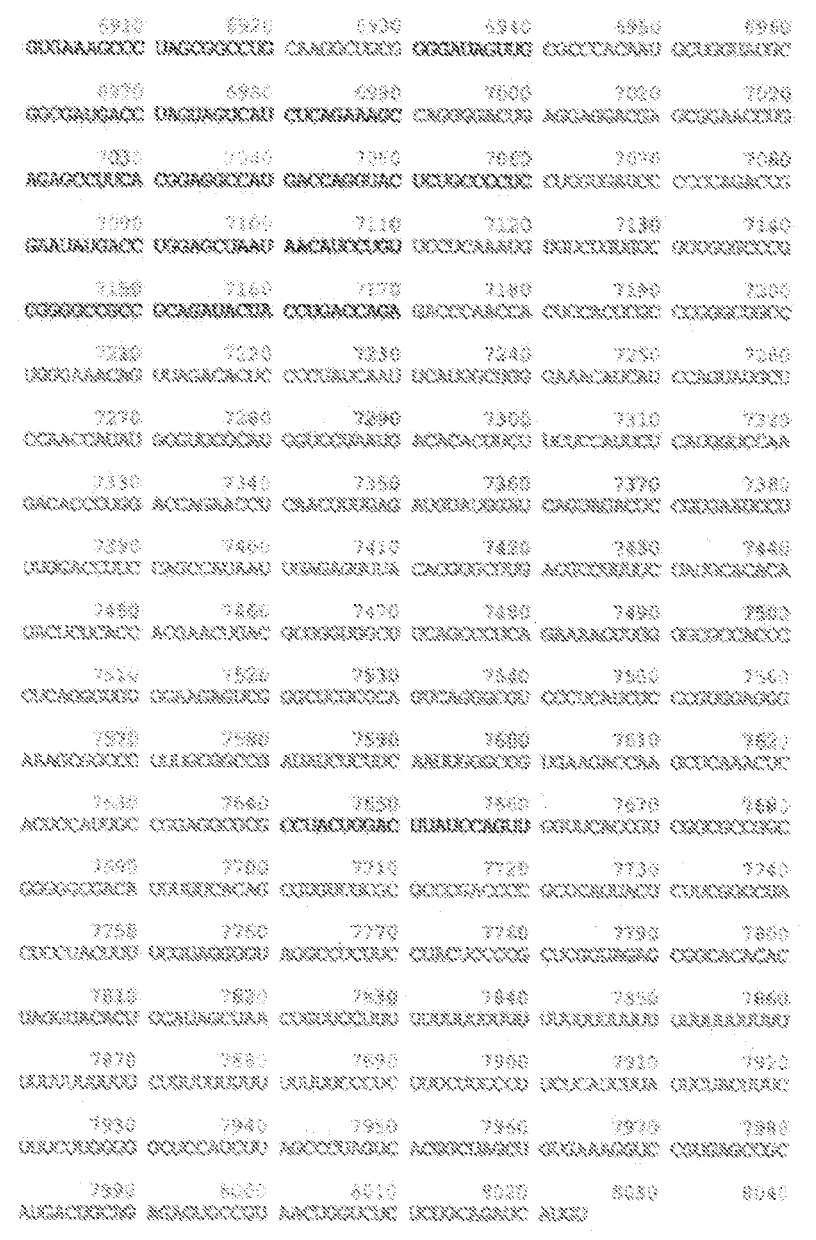

FIG. 2 A to F shows the nucleotide sequence of rSGREP-JFH1 (SEQ ID NO: 1).

Figure 3A:
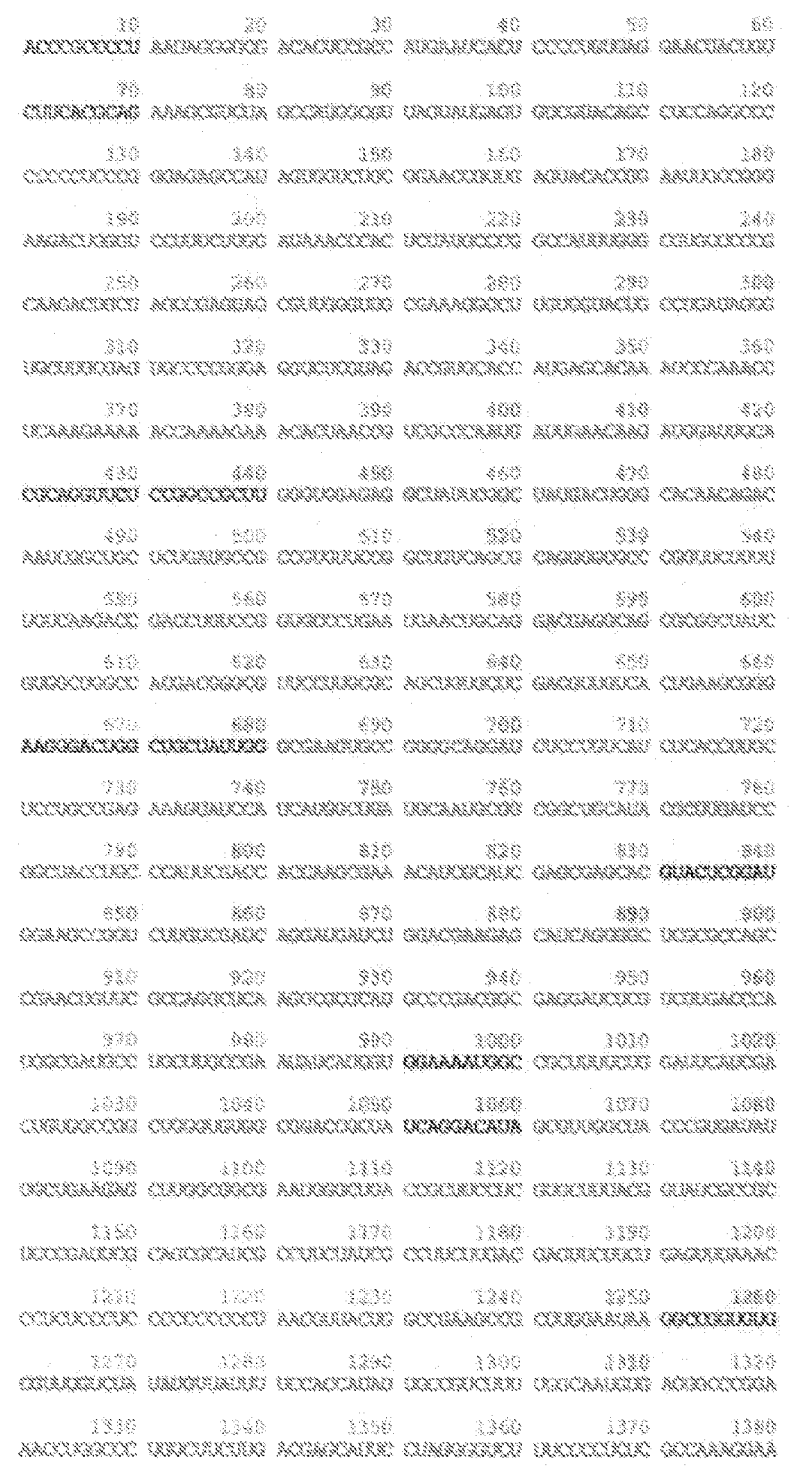
Figure 3B:
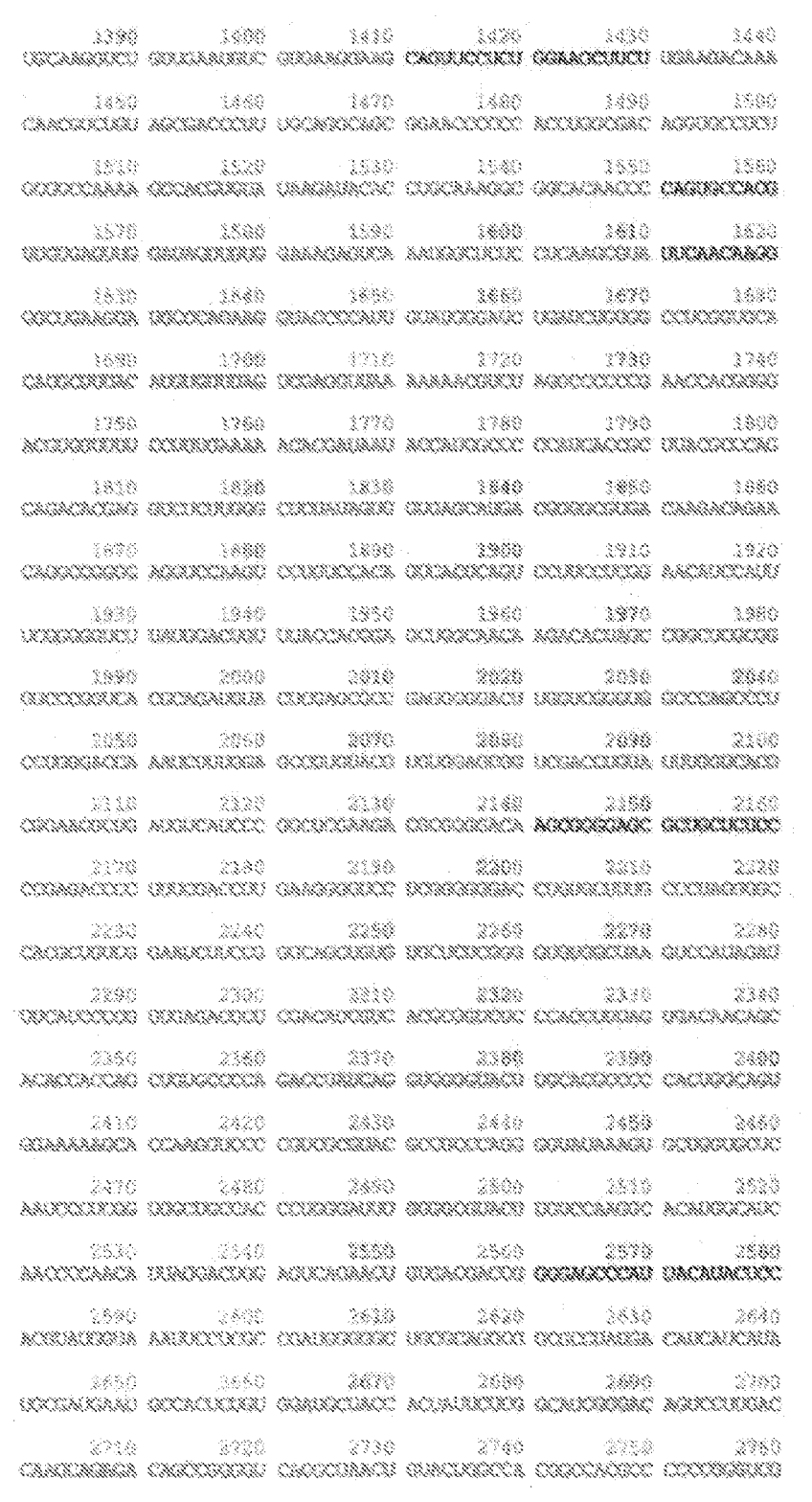
Figure 3C:
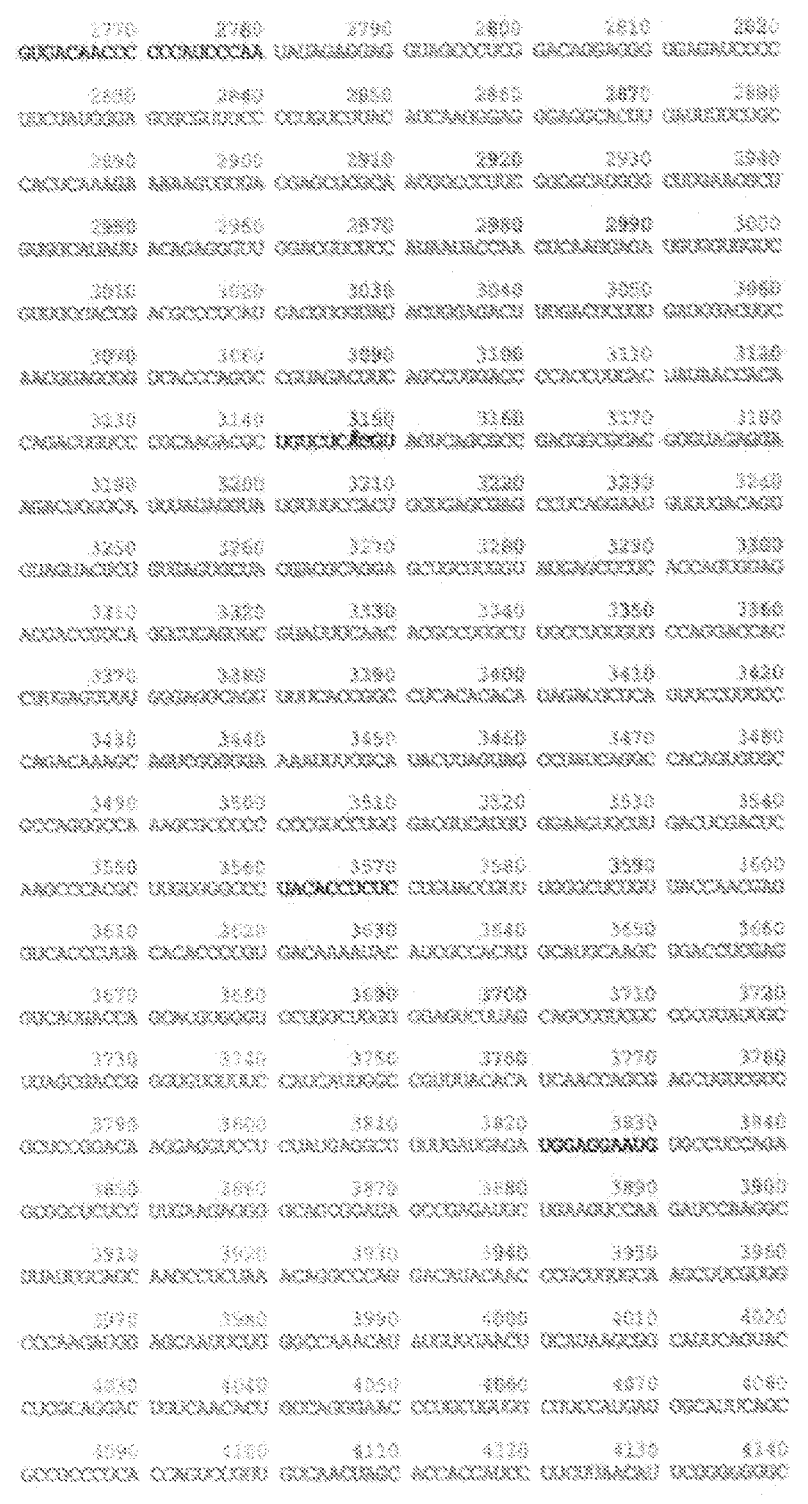
Figure 3D:
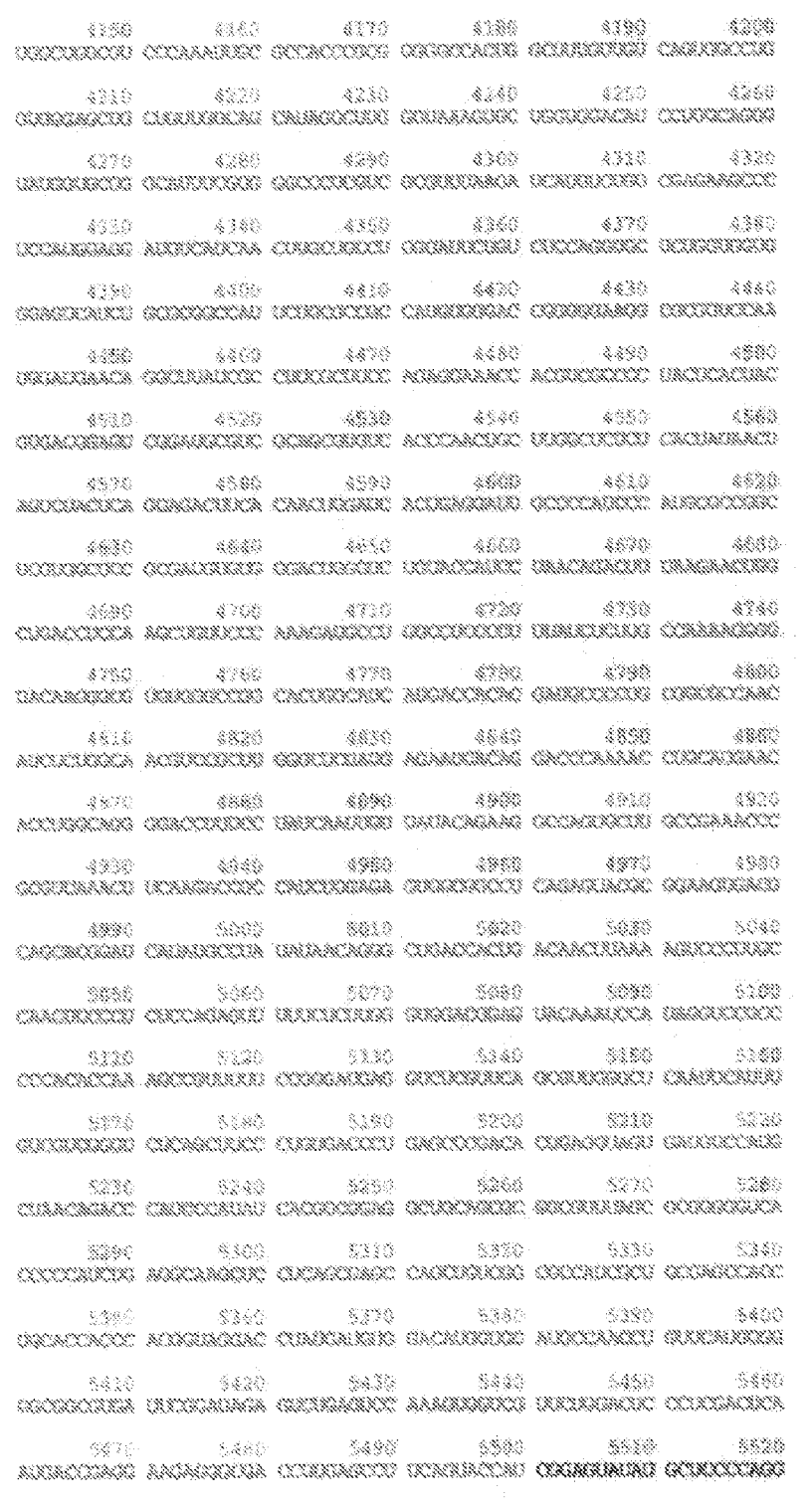
Figure 3E:
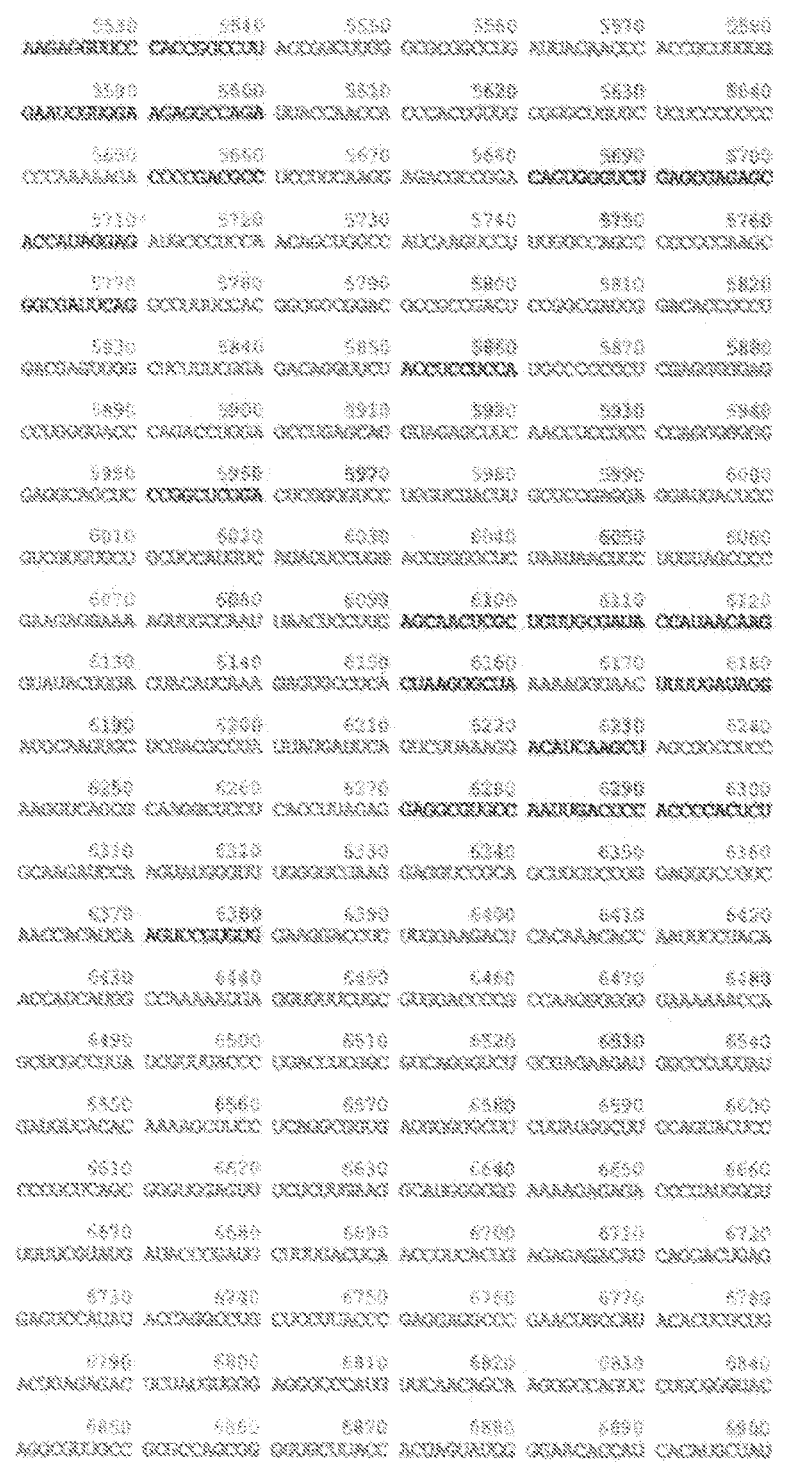
Figure 3F:
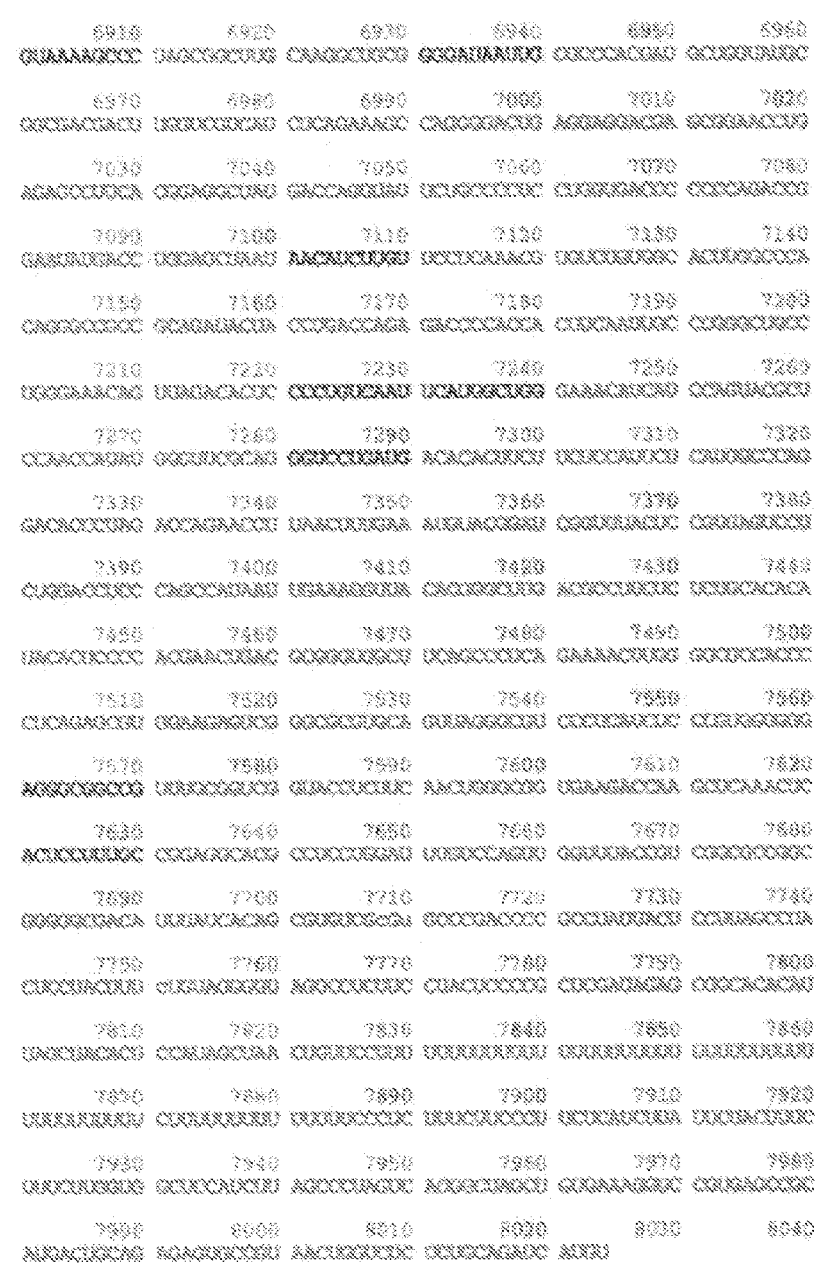

FIG. 3 A to F shows the nucleotide sequence of rSGREP-JCH1 (SEQ ID NO: 2).

FIG. 4 shows photographs showing the colony formation of Huh7 cells to which rSGREP-JFH1, rSGREP-JFH1/GND and rSGREP-JFH1/dGDD was transfected, respectively. The amount of each of three transfected RNAs in the upper section was 100 ng and that of three transfected RNAs in the lower section was 300 ng. 1.0 mg/ml G418 was added to each culture dish.

Figure 5:
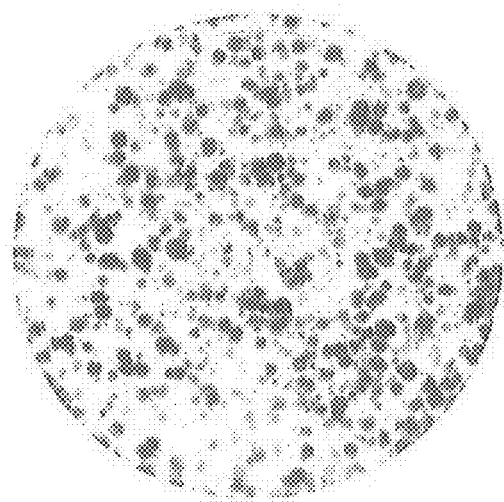

FIG. 5 shows photographs showing colony formation of Huh7 cells to which rSGREP-JFH1 and rSGREP-JCH1 respectively had been transfected when the concentration of G418 was 0.5 mg/ml of the medium. The amount of each of these RNAs transfected was 100 ng.

Figure 6:
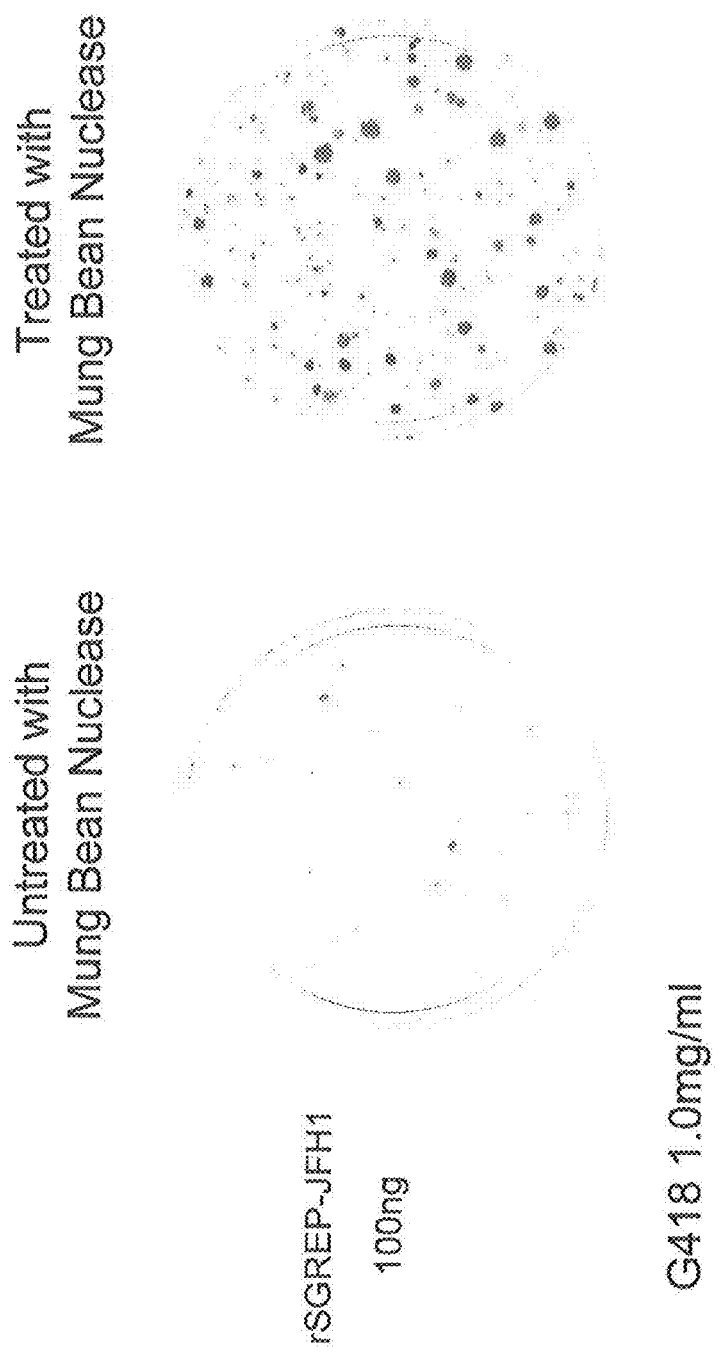

FIG. 6 shows photographs showing the effect of Mung Bean Nuclease treatment conducted on the colony-forming ability of the transfected cells. The amount of rSGREP-JFH1 RNA transfected was 100 ng for both cases. The concentration of G418 was 1.0 mg/ml in both media.

Figure 7:
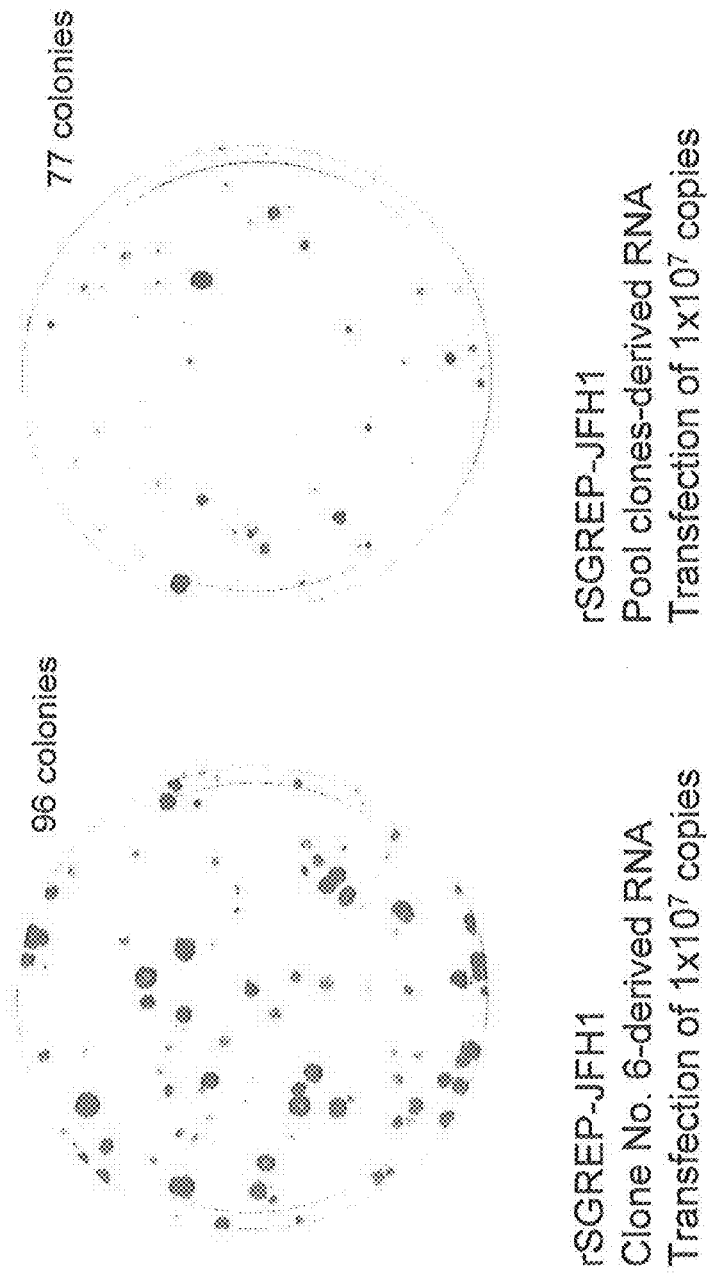

FIG. 7 shows photographs showing colony formation when total cellular RNA derived from the replicon-replicating cell clone, which had been established by transfection of rSGREP-JFH1, was retransfected to another Huh7 cells. The photograph on the left shows that the formation of 96 colonies was observed as a result, when using the total cellular RNA derived from the replicon-replicating cell clone No. 6. The photograph on the right shows that the formation of 77 colonies was observed as a result, when using the total cellular RNA derived from the pool clones. In both cases, RNA was retransfected in an amount containing $1 \times 10^7$ copies of the replicon RNA.

Figure 8:
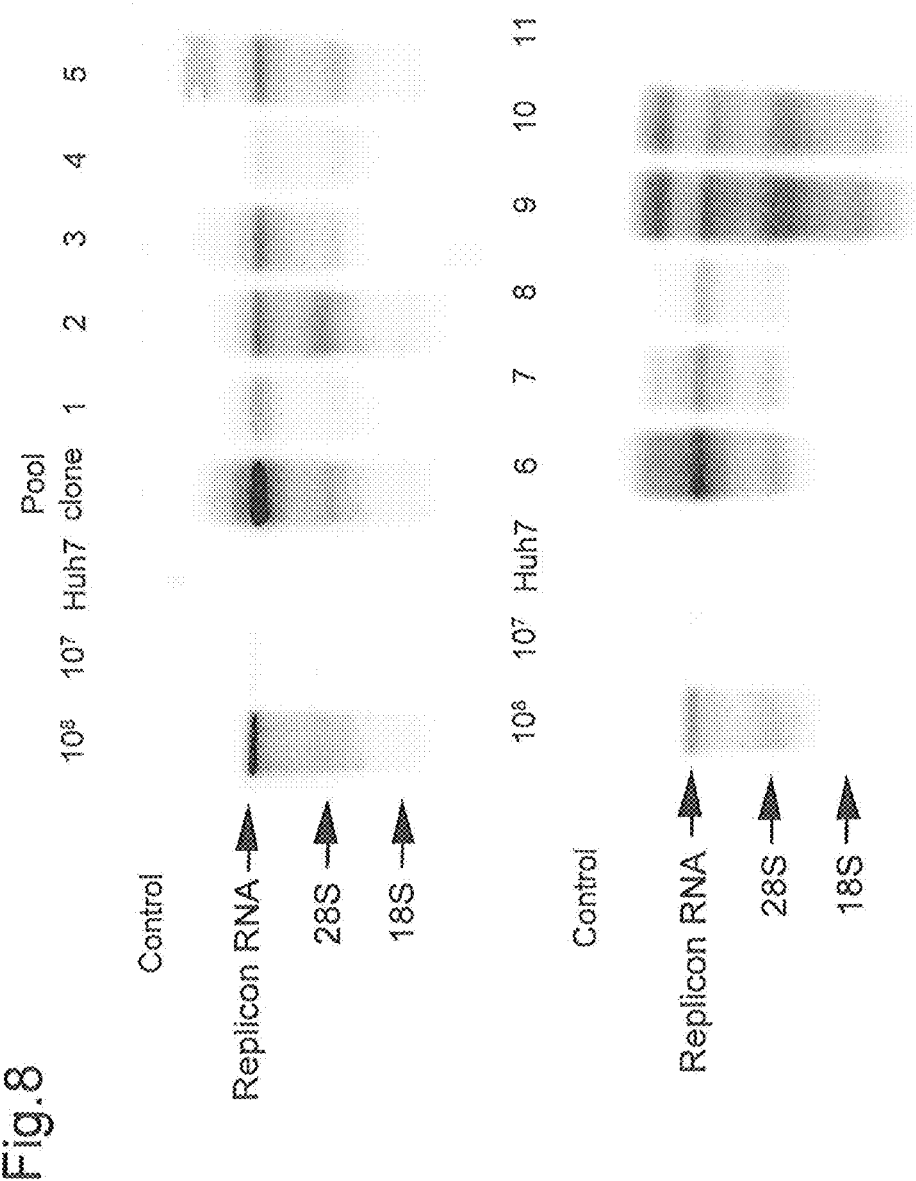

FIG. 8 shows photographs showing the results of detecting by the Northern blot method using an rSGREP-JFH1-specific probe for the total RNA derived from a cell clone that had been obtained by retransfecting the total cellular RNA (derived from the replicon-replicating cell clone established by transfection of rSGREP-JFH1) into another Huh7 cells. Explanation of the lanes is as follows. $10^8$ represents sample prepared by adding $10^8$ copies of the replicon RNA synthesized in vitro to total RNA extracted from Huh7 cells. $10^7$ represents sample prepared by adding $10^7$ copies of the replicon RNA synthesized in vitro to total RNA extracted from Huh7 cells. Huh7, total RNA extracted from untransfected Huh7 cells; pool clone, total RNA extracted from the pool clones; and 1-11, total RNA extracted from each of cell clones Nos. 1 to 11. "Replicon RNA" represents the electrophoresed position of a molecular weight marker indicating the size of rSGREP-JFH1, "28S" represents the same of a ribosomal RNA marker indicating the size of molecular weight of 4.5 kb, and "18S" represents the same of a ribosomal RNA marker indicating the size of molecular weight of 1.9 kb.

Figure 9:
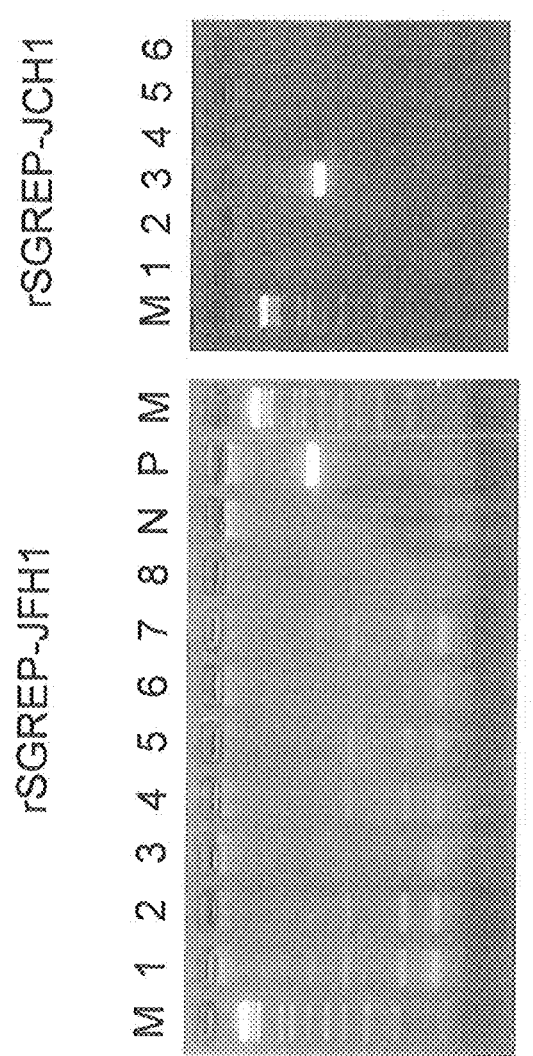

FIG. 9 shows photographs showing the presence or the absence of the incorporation of a neomycin resistance gene into the genomic DNA of a host cell in the cell clone to which rSGREP-JFH1- or rSGREP-JCH1-derived replicated replicon RNA was retransfected. Explanation of the lanes in the photograph on the left is as follows. M, DNA molecular weight marker; 1-8, rSGREP-JFH1-derived cell clones Nos. 1 to 8; N, untransfected Huh7 cells; and P, positive control (PCR amplification product of the neomycin resistance gene). Furthermore, explanation of the lanes in the photograph on the right is as follows. M, DNA molecular weight marker; and 1-6, rSGREP-JCH1-derived cell clones Nos. 1 to 6.

Figure 10:
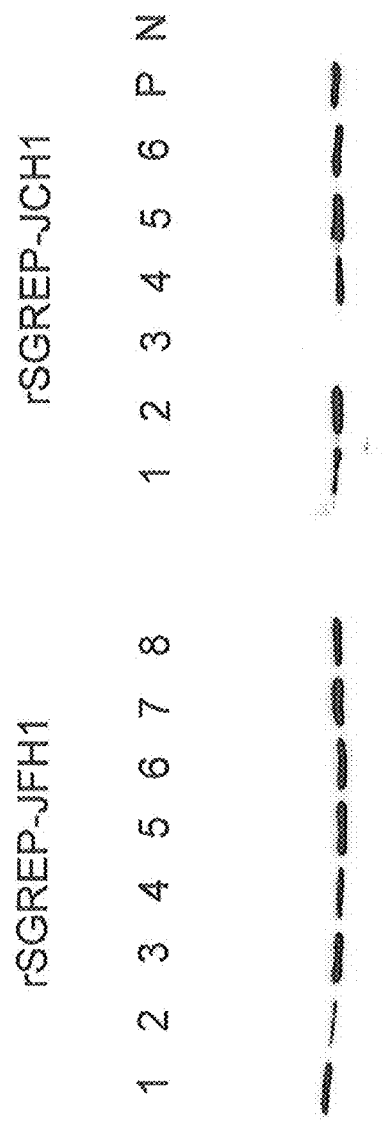

FIG. 10 shows photographs showing the results of detecting NS3 protein expressed in the cell clone that was retransfected with rSGREP-JFH1- or rSGREP-JCH1-derived replicated replicon RNA. Lanes 1 to 8 of the photograph on the left represent rSGREP-JFH1-derived cell clones Nos. 1 to 8. Lanes 1-6 of the photograph on the right represent rSGREP-JCH1-derived cell clones Nos. 1 to 6. Lane P of the photograph on the right represents NS3 protein (positive control) and N represents protein extracted from untransfected Huh7 cells (negative control).

Figure 11:
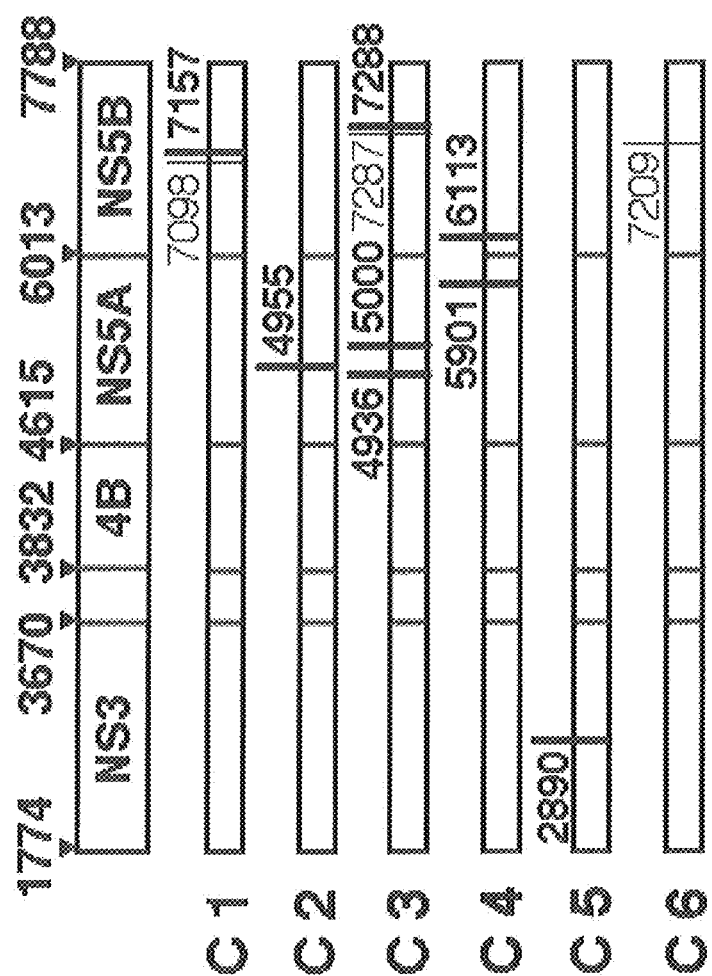

FIG. 11 shows the positions of nucleotide mutations in replicon RNAs obtained from 21 cell clones that were established through the re-transfection of rSGREP-JFH1-derived replicated replicon RNA into Huh7 cells. Mutation positions are indicated using bar lines shown with nucleotide numbers listed in Table 4. A thick bar line denotes nonsynonymous substitution and a thin bar line denotes synonymous substitution.

Figure 12:
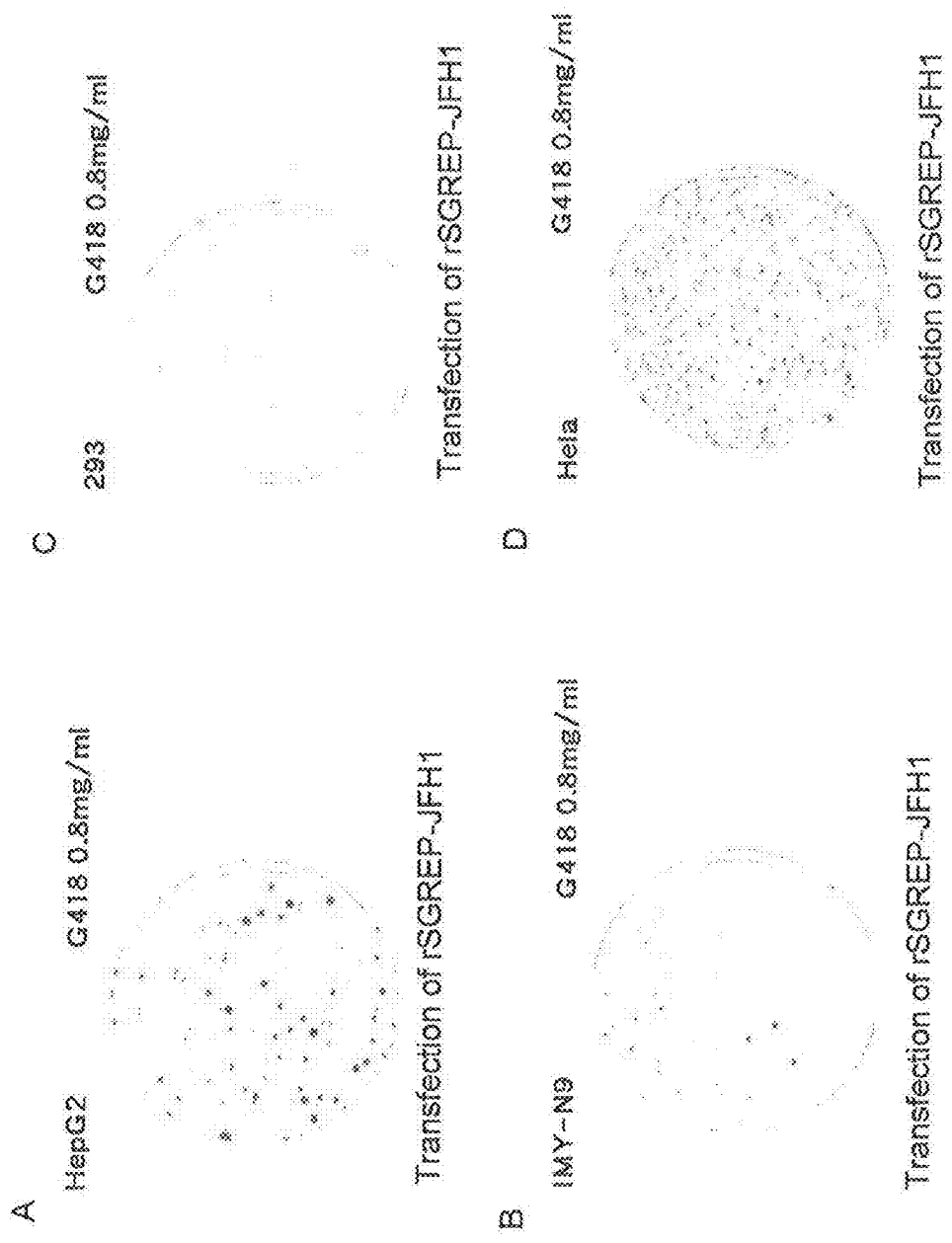

FIG. 12 shows photographs showing the results of transfection with rSGREP-JFH1 using A, HepG2 cells; B, IMY-N9 cells; C, 293 cells; or D, HeLa cells. 0.8 mg/ml G418 was added to each culture dish.

Figure 13:
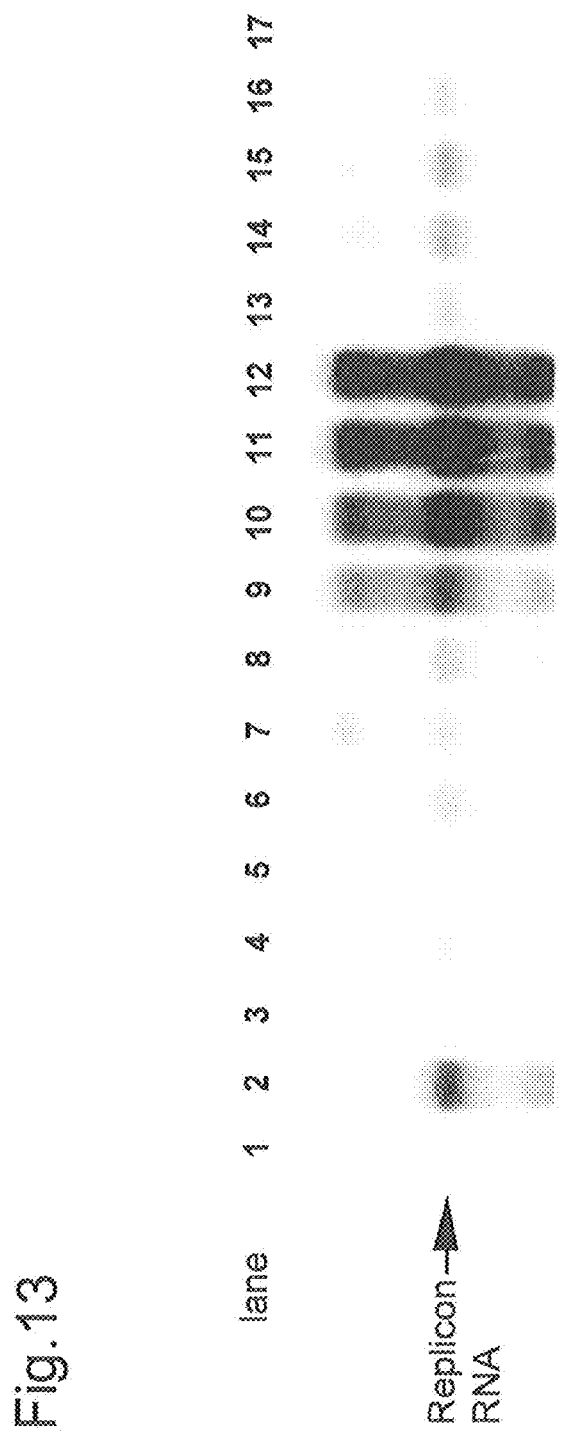

FIG. 13 shows photographs showing the results of performing Northern blotting for replicon-replicating cell clones. Lane 1, HepG2 (negative control); lane 2, $10^8$ copies of synthetic RNA; lane 3, $10^7$ copies of synthetic RNA; lane 4, Hep-IH-1 (derived from HepG2 cells); lane 5, Hep-IH-3 (derived from HepG2 cells); lane 6, Hep-IH-5 (derived from HepG2 cells); lane 7, Hep-IH-11 (derived from HepG2 cells); lane 8, Hep-IH-13 (derived from HepG2 cells); lane 9, IMY-IH-3 (derived from IMY-N9 cells); lane 10, IMY-IH-4 (derived from IMY-N9 cells); lane 11, IMY-IH-7 (derived from IMY-N9 cells); lane 12, IMY-IH-10 (derived from IMY-N9 cells); lane 13, cell pools containing 293-1H transfected therein (derived from 293 cells); lane 14, HeLa-IH-9 (derived from HeLa cells); lane 15, HeLa-IH-12 (derived from HeLa cells); lane 16, HeLa-IH-13 (derived from HeLa cells); and lane 17, HeLa (negative control).

Figure 14:
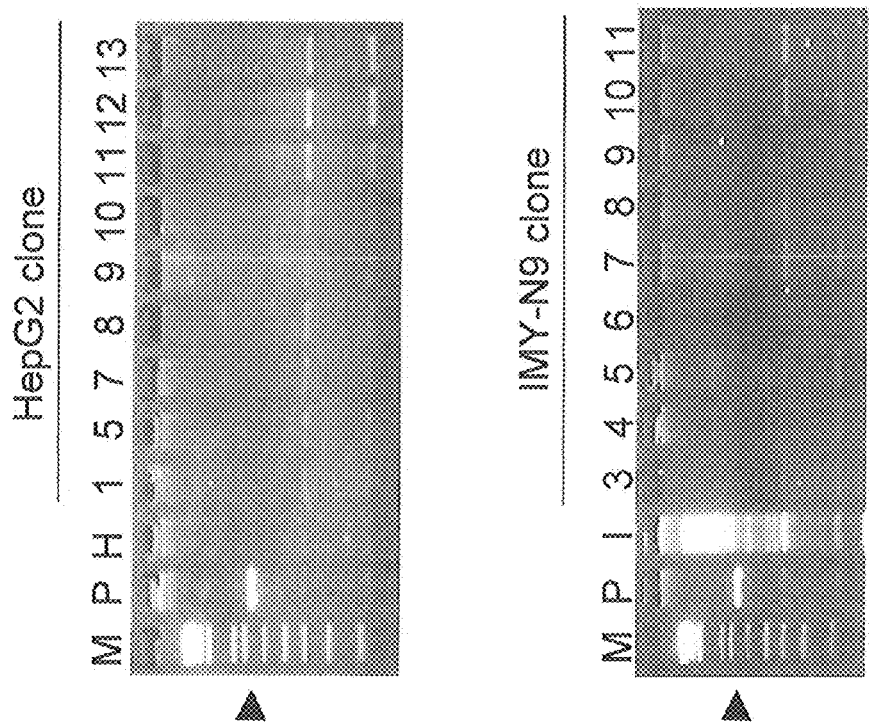

FIG. 14 shows photographs showing the results of electrophoresis performed for confirming the incorporation of the neomycin resistance gene into genomic DNA. For each genomic DNA of HepG2 replicon cells (upper section) and IMY-N9 replicon cells (lower section), detection of the neomycin resistance gene was performed by PCR analysis. M, DNA size marker; P, positive control; H, HepG2 cells; I, IMY-N9 cells; and ▶, PCR product.

Figure 15:
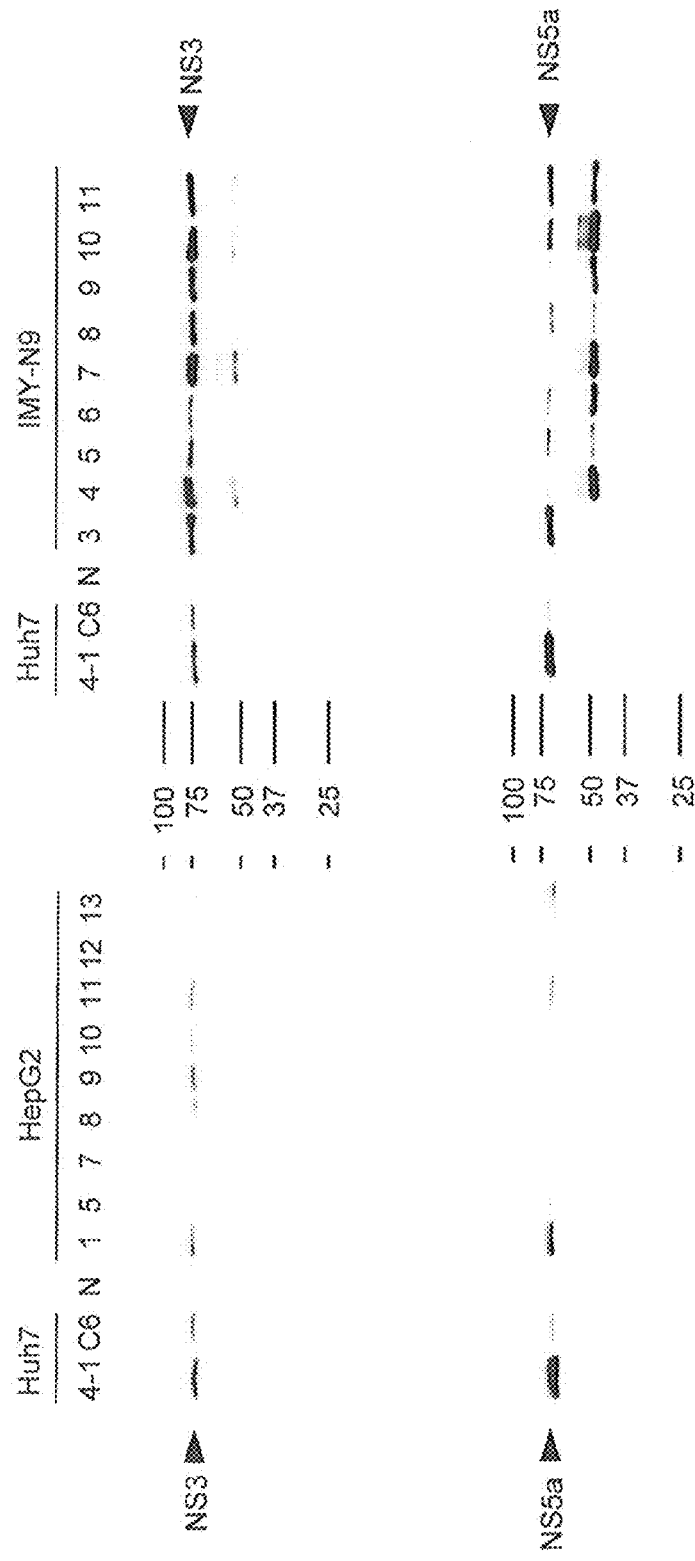

FIG. 15 shows photographs showing the results of analyzing by the Western blot method NS3 and NS5a proteins derived from the replicon-replicating cell clones.

BEST MODE OF CARRYING OUT THE INVENTION

The present invention is explained in detail as follows.

1. HCV-Derived Replicon RNA According to the Present Invention

The genome of hepatitis C virus (HCV) is a single-stranded (+) strand RNA comprising approximately 9600 nucleotides. This genomic RNA comprises the 5' untranslated region (also denoted as 5' NTR or 5' UTR), a translated region composed of a structural region and a non-structural region and the 3' untranslated region (also denoted as 3' NTR or 3' UTR). HCV structural proteins are encoded in the structural region, and a plurality of non-structural proteins are encoded in the non-structural region.

Such HCV structural proteins and non-structural proteins are generated through the translation into a continuous form thereof, a polyprotein, from the translated region, restricted degradation of the polyprotein by protease, and then the release of the structural proteins (Core, E1 and E2) and non-structural proteins (NS2, NS3, NS4A, NS4B, NS5A and NS5B), respectively. Among these structural proteins and non-structural proteins, that is, viral proteins of HCV, Core is a core protein, E1 and E2 are envelope proteins, and non-structural proteins (NS2, NS3, NS4A, NS4B, NS5A and NS5B) are proteins involved in virus's own replication. NS2 is known to have metalloprotease activity, and NS3 is known to have serine protease activity (at one-third of the N terminal side) and helicase activity (at two-thirds of the C-terminal side). Furthermore, NS4A is a cofactor for protease activity of NS3, and NS5B has been reported to have RNA-dependent RNA polymerase activity. Furthermore, the genome of HCV of genotype 2a has already been reported to have a similar gene structure (see JP Patent Publication (Kokai) No. 2002-171978 A).

We have constructed RNA capable of autonomous replication using such HCV genome of genotype 2a. Specifically, the HCV-derived replicon RNA of the present invention is an RNA construct, which contains the whole or partial RNA of the HCV genome of genotype 2a and is capable of autonomous replication.

In this specification, RNA that is prepared by altering the viral genome of HCV and is capable of autonomous replication is referred to as "replicon RNA" or "RNA replicon." RNA that is artificially prepared from HCV of genotype 2a and is capable of autonomous replication is referred to as "replicon RNA derived from HCV of genotype 2a." In this specification, the HCV-derived replicon RNA is also referred to as an HCV-RNA replicon.

In the present invention, "hepatitis C virus of genotype 2a" or "HCV of genotype 2a" means hepatitis C virus identified as genotype 2a according to the international classification of Simmonds et al. The "hepatitis C virus of genotype 2a" or the "HCV of genotype 2a" of the present invention encompasses not only a virus having naturally occurring HCV genomic RNA, but also a virus having genomic RNA prepared by artificially altering a naturally occurring HCV genomic sequence. Specific examples of HCV of genotype 2a include viruses of JFH-1 strain and the JCH-1 strain (see JP Patent Publication (Kokai) No. 2002-171978 A).

Furthermore, "the genomic RNA of hepatitis C virus of genotype 2a" means RNA that comprises the single-stranded (+) strand sense RNA of hepatitis C virus of genotype 2a and has the nucleotide sequence throughout the entire region of its genome. The genomic RNA of hepatitis C virus of genotype 2a is preferably RNA comprising the nucleotide sequence represented by SEQ ID NO: 3 or 5, but is not limited thereto.

In the specification of the present application, "5' untranslated region" (5'NTR or 5'UTR), "a sequence encoding NS3 protein, NS4A protein, NS4B protein, NS5A protein and NS5B protein," "a sequence encoding Core protein" (Core region or C region), "a sequence encoding E1 protein" (E1 region), "a sequence encoding E2 protein" (E2 region), "a sequence encoding N2 protein" (NS2 region), "a sequence encoding NS3 protein" (NS3 region), "a sequence encoding NS4A protein" (NS4A region), "a sequence encoding NS4B protein" (NS4B region), "a sequence encoding NS5A protein" (NS5A region), "a sequence encoding NS5B protein" (NS5B region) and "3' untranslated region" (3' NTR or 3' UTR), and other specific regions or sites are determined based on the nucleotide sequence of SEQ ID NO: 3 of the full-length cDNA (JFH-1 clone) encoding the entire region of the genome of the JFH-1 strain, which is HCV of genotype 2a. The nucleotide sequence of SEQ ID NO: 3 can be obtained from the International DNA Data Bank (DDBJ/EMBL/GenBank) by referring to the accession No. AB047639. Specifically, when a particular HCV RNA sequence is aligned with the nucleotide sequence represented by SEQ ID NO: 3, a sequence to be aligned with nucleotides 1 to 340 on the nucleotide sequence represented by SEQ ID NO: 3 is "5' untranslated region" of the RNA, a sequence to be aligned with the nucleotides 3431 to 9442 on the same are a sequence encoding NS3 protein, NS4A protein, NS4B protein, NS5A protein and NS5B protein, a sequence to be aligned with the nucleotides 3431 to 5323 on the same is "a sequence encoding NS3 protein," a sequence to be aligned with the nucleotides 5324 to 5485 on the same is "a sequence encoding NS4A protein," a sequence to be aligned with the nucleotides 5486 to 6268 on the same is a sequence encoding NS4B protein," a sequence to be aligned with the nucleotides 6269 to 7666 on the same is "a sequence encoding NS5A protein," a sequence to be aligned with the nucleotides 7667 to 9442 on the same is "a sequence encoding NS5B protein," and a sequence to be aligned with the nucleotides 9443 to 9678 on the same is "3' untranslated region." Furthermore, in this case, gaps, additions, deletions, substitutions or the like may be present in the "aligned" sequences. Furthermore, the above "particular HCV" is not limited thereto, and includes the JFH-1 strain or JCH-1 strain, or viral strains that are derivatives thereof.

One embodiment of the HCV RNA-replicon according to the present invention is a replicon RNA comprising a nucleotide sequence containing at least the 5' untranslated region, a sequence encoding NS3 protein, NS4A protein, NS4B protein, NS5A protein and NS5B protein, and the 3' untranslated region on the genomic RNA of hepatitis C virus of genotype 2a. The replicon RNA may further contain at least one selection marker gene or one reporter gene, and at least one IRES sequence. Furthermore, this replicon RNA may also contain a sequence encoding a viral protein other than NS3, NS4A, NS4B, NS5A and NS5B proteins on the genomic RNA of hepatitis C virus of genotype 2a.

Another preferred embodiment of HCV RNA-replicon according to the present invention is a replicon RNA comprising a nucleotide sequence containing the 5' untranslated region comprising the nucleotide sequence represented by SEQ ID NO: 9 or 10, at least one selection marker gene or reporter gene, the IRES sequence, a sequence encoding NS3 protein, NS4A protein, NS4B protein, NS5A protein and NS5B protein on the genomic RNA of hepatitis C virus of genotype 2a, and the 3' untranslated region comprising the nucleotide sequence represented by SEQ ID NO: 11 or 12. In this case the nucleotide sequences represented by SEQ ID NO: 9 and 10 are sequences of the 5' untranslated regions of rSGREP-JFH1 (SEQ ID NO: 1) and rSGREP-JCH1 (SEQ ID NO: 2), respectively, which are replicon RNAs according to the present invention. Furthermore, the nucleotide sequences represented by SEQ ID NO: 11 and 12 are sequences of the 3' untranslated regions of rSGREP-JFH1 (SEQ ID NO: 1) and rSGREP-JCH1 (SEQ ID NO: 2), respectively, which are replicon RNAs according to the present invention.

A more preferred embodiment of HCV RNA-replicon according to the present invention is a replicon RNA comprised of an RNA comprising the nucleotide sequence represented by SEQ ID NO: 1 or 2. Furthermore, a replicon RNA comprising a nucleotide sequence derived from the nucleotide sequence represented by SEQ ID NO: 1 or 2 by deletion, substitution or addition of 1 to 50, 1 to 30, 1 to 10, 1 to 6, or 1 to several (2 to 5) nucleotides, and being capable of autonomous replication is also included in the scope of the present invention as a preferred embodiment. In the present invention, "capable of autonomous replication" means that when replicon RNA is introduced into a cell, the replicon RNA allows its own full-length sequence to be replicated within the cell. For example, this ability of autonomous replication can be confirmed by transfecting replicon RNA into Huh7 cells, culturing the Huh7 cells, extracting RNA from the cells in the thus resulting culture product and conducting Northern blot hybridization for the extracted RNA using a probe that can specifically detect the transfected replicon RNA so as to detect the presence of the replicon RNA. However, examples of such a method are not limited thereto. Specific procedures for confirming the ability of autonomous replication can be conducted according to descriptions given in the Examples of this specification such as those for measuring the ability of colony formation, those for confirming the expression of HCV proteins or those for detecting replicon RNA.

In the present invention, a "selection marker gene" means a gene that can provide a cell with selectivity such that only the cell expressing the gene is selected. A general example of a selection marker gene is an antibiotic resistance gene. In the present invention, preferred examples of a selection marker gene include a neomycin resistance gene, a thymidine kinase gene, a kanamycin resistance gene, a pyrithiamine resistance gene, an adenylyl transferase gene, a Zeocin resistance gene and a puromycin resistance gene. The neomycin resistance gene and the thymidine kinase gene are preferred, and the neomycin resistance gene is more preferred. However, the selection marker gene in the present invention is not limited to these genes.

Furthermore in the present invention, a "reporter gene" means a marker gene encoding a gene product that is a marker for the expression of the gene. General examples of a reporter gene include structural genes of enzymes that catalyze light emitting reaction or color reaction. Preferred examples of the reporter gene in the present invention include a transposon Tn9-derived chloramphenicol acetyltransferase gene, an *Escherichia coli*-derived β glucuronidase or β galactosidase gene, a luciferase gene, a green fluorescence protein gene, an aequorin gene from jellyfish, and a secreted placental alkaline phosphatase (SEAP) gene. However, the reporter gene in the present invention is not limited to these genes.

Either only one or both of the above selection marker gene and reporter gene may be contained in replicon RNA.

In the present invention, "IRES sequence" means an internal ribosome entry site that allows translation to be initiated by binding ribosomes within the inside of RNA. Preferred examples of IRES sequence in the present invention include, but are not limited to, EMCV IRES (the internal ribosome entry site of encephalomyocarditis virus), FMDV IRES and HCV IRES. EMCV IRES and HCV IRES are more preferred, and EMCV IRES is the most preferred sequence.

The replicon RNA according to the present invention may further contain a sequence on the genomic RNA of another HCV strain or HCV of another genotype. For example, the replicon RNA may also contain a fragment of HCV genome of genotype 1b. Examples of another HCV strain include, but are not limited to, HCV-1, HCV-H, HC-J1, HCT-18, H77, DK-7, US11, S14, HCT23, HCV-Th, DR1, DR4, HCT27, S18, SW1, DK9, H90, TD-6E1, S9, HCV-BK, T10, DK1, HC-J4, HCV-J, HK3, HK8, HK5, HCV-G3, IND5, IND8, P10, D1, D3, SW2, T3, S45, SA10, US6, HCV-JK1, HCV-JK4, HCV-JK3, HCV-JK2, HCV-JT, HC-J2, HCV-T, HK4, HC-G9, Z1, Bi, S. I., Cho, J.M., HCV-J6, T4, T9, US10, HC-J5, T2, HC-J7, DK11, SW3, DK8, T8, HC-J8, S83, HK2, HC-J6, HC-J8, BEBE1, HCV-J6, HCV-J8, HD10-2, BR36-9, S52, S54, S2, BR33-1, HK10, DK12, HCV-TR, BA-1, BA-2, DK13, Z1, Z4, Z6, Z7, HK2, SA1, SA4, SA5, SA7, SA13, SA6, NZL1, SA30, EG-13, HCV-K3a/650, ED43, EUH1480, EUHK2, Th580, VN235, VN405, VN004, JK049, JK046, JFH-1, JCH-1, JCH-2, JCH-3, JCH-4, JCH-5, JCH-6, J6CF and H77.

The replicon RNA according to the present invention preferably has the 5' untranslated region on the genomic RNA of HCV of genotype 2a on the 5'-most side, and the 3' untranslated region on the genomic RNA of HCV of genotype 2a on the 3'-most side. A selection marker gene or a reporter gene may be ligated upstream of the IRES sequence, or upstream or downstream of "the sequence encoding NS3 protein, NS4A protein, NS4B protein, NS5A protein and NS5B protein," or inserted in the middle of "the sequence encoding NS3 protein, NS4A protein, NS4B protein, NS5A protein and NS5B protein."

The replicon RNA according to the present invention more preferably has the 5' untranslated region on the genomic RNA of HCV of genotype 2a on the 5'-most side, and a selection marker gene or a reporter gene, the IRES sequence and "the sequence encoding NS3 protein, NS4A protein, NS4B protein, NS5A protein and NS5B protein" downstream of the 5' untranslated region in this order, and the 3' untranslated region on the genomic RNA of HCV of genotype 2a on the 3'-most side.

Examples of the replicon RNA according to the present invention may include an RNA containing any foreign gene to be expressed within a cell into which the replicon RNA is introduced, in addition to the sequences as described above. A foreign gene may also be ligated downstream of the 5' untranslated region, or ligated upstream or downstream of a selection marker gene or a reporter gene, or ligated upstream or downstream of "the sequence encoding NS3 protein, NS4A protein, NS4B protein, NS5A protein and NS5B protein," or may be inserted in the middle of "the sequence encoding NS3 protein, NS4A protein, NS4B protein, NS5A protein and NS5B protein." A replicon RNA containing a foreign gene can express a protein encoded by the foreign gene when it is translated within a cell into which the RNA is introduced. Thus, the replicon RNA containing a foreign gene can be appropriately used also for gene therapy or the like, the purpose of which is to generate a particular gene product within a cell.

The replicon RNA according to the present invention may further contain a ribozyme. A ribozyme is inserted to ligate a selection marker gene, a reporter gene or a foreign gene on the 5' side in the replicon RNA to those located on the 3' side thereof including the IRES sequence and "the sequence encoding NS3 protein, NS4A protein, NS4B protein, NS5A protein and NS5B protein," so that it enables cleavage and separation of the two by the self-cleavage activity of the ribozyme.

In the replicon RNA according to the present invention, the above described selection marker gene, reporter gene, sequences encoding viral proteins on the genomic RNA of hepatitis C virus of genotype 2a, sequences encoding viral proteins of HCV of a genotype other than genotype 2a, a foreign gene or the like are ligated so that they are translated from the replicon RNA in the correct reading frame. Among these sequences, the protein-coding sequences may be ligated to each other via a protease cleavage site and the like, so that after the proteins are expressed as a fusion protein with the polyprotein that is translated from "the sequence encoding NS3 protein, NS4A protein, NS4B protein, NS5A protein and NS5B protein" of hepatitis C virus of genotype 2a, the fusion protein is separated by protease into each protein.

2. Preparation of Replicon RNA According to the Present Invention

The HCV RNA-replicon according to the present invention can be prepared using any genetic engineering techniques known by persons skilled in the art. The HCV RNA-replicon can be prepared by, for example, the following method, but the method of preparation is not limited thereto.

First, DNA corresponding to the entire region of the genomic RNA of hepatitis C virus of genotype 2a is ligated downstream of an RNA promoter according to a standard procedure so as to prepare a DNA clone. As used herein, "DNA corresponding to RNA" means a DNA having a nucleotide sequence derived from the nucleotide sequence of the RNA by substituting U (uracil) with T (thymine). The above RNA promoter is preferably an RNA promoter contained in a plasmid clone. An example of an RNA promoter is not limited, but T7 RNA promoter is particularly preferred.

Next, for the thus prepared DNA clone, for example, the structural region (Core sequence, E1 sequence and E2 sequence) located downstream of the 5' untranslated region and the sequence encoding NS2 protein are substituted with a DNA fragment containing a selection marker gene or a reporter gene and the IRES sequence ligated downstream thereof. In this substitution, portions other than the structural region, such as a fragment on the 3' terminal side of the 5' untranslated region or a part of the sequence encoding NS3 protein may be substituted with a sequence derived from HCV of another genotype.

Subsequently, using the DNA clone after the substitution as a template, RNA is synthesized using RNA polymerase. RNA synthesis can be initiated by a standard procedure from the 5' untranslated region and the IRES sequence. When a template DNA is a plasmid clone, the above DNA region ligated downstream of an RNA promoter is excised by a restriction enzyme from the plasmid clone, and then RNA can be synthesized using the DNA fragment as a template. In addition, preferably the 3' terminus of RNA to be synthesized agrees with the 3' untranslated region of the viral genomic RNA, and no other sequences are added or deleted. The thus synthesized RNA is the replicon RNA according to the present invention.

3. Preparation of Replicon-Replicating Cells into which Replicon RNA from HCV of Genotype 2a is Introduced The replicon RNA that is prepared as described above is introduced into cells in which the replicon RNA should be replicated, so that cells wherein the replicon RNA is continuously replicated can be obtained. In this specification, a cell wherein replicon RNA is continuously replicated is referred to as a "replicon-replicating cell."

As a cell into which replicon RNA is introduced, any cell can be used, as long as it can be subcultured. Such a cell is preferably a eukaryotic cell, more preferably a human liver-derived cell, a human uterine cervix-derived cell or a human fetal kidney-derived cell, and further preferably any cell selected from the group consisting of Huh7 cells, HepG2 cells, IMY-N9 cells, HeLa cells and 293 cells. As these cells, commercially available cells may be utilized, these cells may be obtained from cell depositories, or cell lines established from any cells (e.g., cancer cells or stem cells) may also be used.

As the above cells, cells that can be mass-cultured are preferably used for the purpose of the mass production of HCV proteins, such as in the case of vaccine production. From such a viewpoint, the cells are preferably those other than Huh7 cells.

Introduction of replicon RNA into cells can be performed using any technique known by persons skilled in the art. Examples of such an introduction method include electroporation, a particle gun method, a lipofection method, a calcium phosphate method, a microinjection method and a DEAE sepharose method. The method using electroporation is particularly preferred.

A replicon RNA of interest may be introduced alone, or may be introduced after it is mixed with other nucleic acids. To vary the quantity of replicon RNA while keeping RNA quantity to be introduced at a certain level, the replicon RNA of interest is mixed with total cellular RNA extracted from cells into which the RNA is introduced, and then the mixture is used for introduction into cells. The quantity of replicon RNA to be used for introduction into cells may be determined depending on the introduction method employed, and is preferably between 1 picogram and 100 micrograms, and more preferably between 10 picograms and 10 micrograms.

When replicon RNA containing a selection marker gene or a reporter gene is used for introduction into cells, cells wherein the replicon RNA is introduced and continuously replicated can be selected utilizing the expression of the selection marker gene or the reporter gene. Specifically, for example, such cells into which replicon RNA has been introduced may be cultured in media whereby the cells can be selected by the expression of the selection marker gene or the reporter gene. As an example, when replicon RNA contains a neomycin resistance gene as a selection marker gene, cells into which replicon RNA has been intracellularly introduced are seeded into a culture dish. After 16 to 24 hours of culture, G418 (neomycin) is added to the culture dish at a concentration of 0.05 milligrams/milliliter to 3.0 milligrams/milliliter. The cells are continuously cultured for preferably 10 days to 40 days and more preferably 14 days to 28 days after seeding, while exchanging the culture solution twice a week. Next, surviving cells are stained with crystal violet, so that cells into which the replicon RNA has been introduced and is being continuously replicated can be selected as formed colonies.

Cloned cells can be obtained from the formed colonies by cloning surviving cells by a standard procedure, and then continuing the culture of the cells. The thus obtained cell clone wherein the replicon RNA of interest is continuously replicated is referred to as "a replicon-replicating cell clone" in this specification.

Regarding the established cell clone, detection of a replicon RNA that has been replicated from the introduced replicon RNA in the cell clone, confirmation of the presence or the absence of the incorporation of a selection marker gene or a reporter gene in the introduced replicon RNA into a host genomic DNA, and confirmation of the expression of an HCV protein are preferably carried out to confirm the fact that a replicon RNA of interest is actually and continuously replicated.

A replicon RNA that has been replicated from the introduced replicon RNA in the cell clone (in this specification, hereinafter conveniently referred to as "replicated replicon RNA") may be detected according to any RNA detection method known by persons skilled in the art. For example, detection can be performed by conducting the Northern hybridization method for total RNA extracted from the cell clone using as a probe a DNA fragment specific to the introduced replicon RNA.

Furthermore, the presence or the absence of the incorporation of a selection marker gene or a reporter gene in the introduced replicon RNA into a host genomic DNA can be confirmed by, for example, performing PCR for the host genomic DNA extracted from the cell clone to amplify at least a part of the selection marker gene or the reporter gene, and then confirming the presence or the absence of the amplified product. However, examples of relevant methods are not limited thereto. A cell clone for which the amplified product is confirmed is considered to have a selection marker gene or a reporter gene incorporated in the host genome. Thus, regarding the cell clone, the replicon RNA itself may not be continuously replicated within the cell. In this case, whether or not the replicon RNA is continuously replicated can be confirmed by conducting an experiment to confirm the expression of an HCV protein, as described below.

The expression of an HCV protein can be confirmed by, for example, causing an antibody against an HCV protein to be expressed from the introduced replicon RNA and to react with a protein extracted from a cell clone. This method can be conducted by any protein detection method known by persons skilled in the art. Specifically, for example, a protein sample extracted from the cell clone is blotted onto a nitrocellulose membrane, with which an anti-HCV protein antibody (e.g., an anti-NS3-specific antibody or an antiserum collected from a hepatitis C patient) is reacted, and then the anti-HCV protein antibody is detected. If the HCV protein is detected among proteins extracted from the cell clone, it can be concluded that this cell clone continuously replicate HCV-derived replicon RNA to express the HCV protein.

As described above, cell clones confirmed to continuously replicate a replicon RNA of interest (replicon-replicating cell clones) can be obtained. Furthermore in the present invention, replicon RNA can be obtained by any method known by persons skilled in the art, for example, by extracting RNA from the replicon-replicating cell, and then separating replicon RNA from the RNA by an electrophoresis method. The present invention also relates to such a method of producing replicon RNA. Moreover, preferably, the replicon-replicating cell according to the present invention can be used for producing HCV proteins. Persons skilled in the art can obtain HCV proteins from the replicon-replicating cells according to any standard method. Specifically, for example, a viral protein of hepatitis C virus of genotype 2a can be produced by culturing replicon-replicating cells, collecting proteins from the resulting culture product (including cultured cells and culture media) by a standard procedure, and then selectively obtaining viral proteins from the proteins by detection or the like using an anti-HCV protein antibody.

Moreover, when the replicon-replicating cell according to the present invention continuously replicates replicon RNA containing a foreign gene, a protein encoded by the foreign gene can be obtained by the expression thereof using the replicon-replicating cell. Specifically, for example, the protein encoded by a foreign gene can be obtained by culturing replicon-replicating cells, collecting proteins from the resulting culture product (including cultured cells and culture media) by a standard procedure, and then selectively obtaining the protein from among the proteins by detection or the like using an antibody against the protein of interest.

4. Introduction of Mutation that Increases Replication Efficiency into Replicon RNA from HCV of Genotype 2a Mutation producing enhancement of replication efficiency frequently takes place in the replicon RNA that is replicated or generated in the replicon-replicating cell (replicated replicon RNA) according to the present invention. Such a mutation may be an adaptive mutation.

Utilizing this fact, introduction of a mutation enhancing replication efficiency into the replicon RNA according to the present invention can be promoted in the present invention.

Specifically, the step comprising obtaining a first replicated replicon RNA by extraction or the like from a first replicon-replicating cell (preferably, a replicon-replicating cell, wherein the replicon RNA according to the present invention has been introduced), and then re-introducing the first replicated replicon RNA into another cell to prepare a second replicon-replicating cell is performed repeatedly once or more, preferably 1 to 10 times, more preferably 1 to 5 times, and further preferably 1 to 2 times, so that the mutation increasing replication efficiency can be introduced at a high frequency into the replicon RNA within the replicon-replicating cells.

As a cell into which a replicated replicon RNA is re-introduced, any cell can be used. Such a cell is preferably derived from a biological species that is the same as that of a cell wherein replicon RNA is introduced at the beginning, more preferably derived from the same tissue derived from the same biological species as that of a cell wherein replicon RNA is introduced at the beginning, and further preferably of a cell line that is the same as that for a cell wherein replicon RNA is introduced at the beginning.

Therefore in the present invention, using the above method, replicon RNA wherein the mutation increasing replication efficiency is introduced can be produced. Specifically, the step comprising obtaining a first replicated replicon RNA by extraction or the like from a first replicon-replicating cell (preferably, a replicon-replicating cell, into which the replicon RNA according to the present invention has been introduced), and then re-introducing the first replicated replicon RNA into another cell so as to prepare a second replicon-replicating cell is performed repeatedly once or more, preferably 1 to 10 times, more preferably 1 to 5 times, and further preferably 1 to 2 times. Subsequently, the replicated replicon RNA is obtained by extraction or the like from the replicon-replicating cell finally obtained at the end of the repeated steps, so that replicon RNA with increased replication efficiency can be produced.

In the present invention, the replication efficiency of a replicon RNA can be increased at least 2 times, preferably 10 to 100 times, and more preferably 100 to 10000 times by the above method.

Regarding the replicon RNA that is produced by such a method so as to have increased replication efficiency, the nucleotide sequence is preferably determined by a known method, for example, by obtaining cDNA by reverse transcription PCR and subjecting such cDNA to sequencing.

Furthermore, the thus determined nucleotide sequence or the amino acid sequence encoded by the nucleotide sequence is compared with the nucleotide sequence of replicon RNA that had been introduced at the beginning into cells, so that adaptive mutation can be identified. As adaptive mutation increasing replication efficiency, in particular, nonsynonymous substitution that mutates an amino acid in a viral protein encoded by replicon RNA is preferred.

The present invention also provides a method whereby the replicon RNA of hepatitis C virus of genotype 2a having increased replication efficiency can be produced by introducing the thus identified adaptive mutation into replicon RNA, the replication efficiency of which is to be increased, by a standard procedure.

The replicon RNA that is produced as described above so as to have increased replication efficiency can be used for producing replicon RNA in large quantity within cells that have been used for the method.

The replication efficiency of the replicon RNA according to the present invention can be determined by a method known by persons skilled in the art. For example, it can be determined according to the following method. Replicon RNAs are transfected in quantities of 0.0001, 0.0003, 0.001, 0.003, 0.01, 0.03, 0.1, 0.3 and 1.0 micrograms, respectively, into Huh7 cells, selective culture with G418 is performed for 21 days in a method similar to the above experimental techniques, and then the number of colonies formed (number of colonies) is counted. The quantity of RNA introduced is compared with the number of colonies formed to determine the range of the quantity of the replicon RNA introduced, within which colony formation increases in a quantity-dependent manner. The number of colonies formed within the range is divided by the quantity of RNA introduced, and the resulting value is regarded as the colony forming activity per microgram. This equation is as follows.

Colony forming activity[(Colony Forming Unit, or CFU)/microgram]=Number of colonies formed [colony]/quantity of RNA introduced[microgram]

The thus calculated colony forming activity is regarded as a value representing the replication efficiency of replicon RNA introduced. Specifically, the higher the colony forming activity, the higher the replication efficiency of the replicon RNA. In addition, the replication efficiency of replicon RNA can also be shown via a colony-forming ability that is represented by the number of copies of the replicon RNA introduced per formed colony. That is, in this case, the ability can be calculated according to the following equation.

Colony forming ability=number of copies of replicon RNA introduced[copy]/number of formed colonies[colony]

5. Other Embodiments of the Present Invention

The replicon RNA-replicating cell according to the present invention can also be used as a test system for, for example, screening for a substance that promotes or suppresses the replication of hepatitis C virus. Specifically, for example, replicon replicating cells are cultured in the presence of a test substance, replication of the replicon RNA in the resulting culture product is detected, and then whether or not the test substance promotes or suppresses the replication of the replicon RNA is determined, so that a substance that promotes or suppresses the replication of hepatitis C virus can be screened for. In this case, detection of the replication of the replicon RNA in the resulting culture product may be conducted by detecting the quantity of, or the presence or the absence of, the replicon RNA in the RNAs extracted from the replicon RNA-replicating cell, or by detecting the quantity of, or the presence or the absence of, HCV protein contained in the proteins in the culture product or in the replicon RNA-replicating cells contained in the culture product.

Such a test cell system using the replicon RNA-replicating cells according to the present invention may be aimed at producing or evaluating a therapeutic agent or a diagnostic agent for treating hepatitis C virus infection. Specific examples of such purposes include the following examples.
(1) Search for a substance suppressing the proliferation of HCV of genotype 2a Examples of a substance suppressing the proliferation of HCV of genotype 2a include organic chemicals directly or indirectly affecting the proliferation of HCV of genotype 2a, and antisense oligonucleotides directly or indirectly affecting the proliferation of HCV or the translation of HCV proteins by hybridizing to a target sequence in the HCV genome of genotype 2a or a complementary strand thereof.
(2) Evaluation of various substances having antiviral action in cell culture Examples of the various substances include substances obtained through rational drug design or high throughput screening (e.g., an isolated and purified enzyme) and the like.
(3) Identification of a new target for attack for treating patients infected with HCV of genotype 2a To identify a host cellular protein that plays an important role in proliferation of HCV virus, for example, the replicon-replicating cell according to the present invention can be used.
(4) Evaluation of the ability of HCV virus to acquire resistance against a drug or the like and identification of mutation concerning such resistance
(5) Production of a viral protein as an antigen that can be used for developing, producing and evaluating a diagnostic agent or a therapeutic agent for hepatitis C virus infection
(6) Viral genome replication system for producing HCV virus or virus-like particles that can be used for developing, producing and evaluating a diagnostic agent or a therapeutic agent for hepatitis C virus infection
(7) Production of a vaccine antigen that can be used as a vaccine against HCV of genotype 2a
(8) Production of hepatic cell-directed genetic vector that is used after the incorporation of a foreign gene therein for gene therapy 6. Examples The present invention will be described more specifically based on the following examples and drawings. However, the technical scope of the present invention is not limited by these examples.

Example 1

Preparation of Replicon RNA (A) Construction of Expression Vector

DNA corresponding to the entire region of viral genome of hepatitis C virus JFH-1 strain (genotype 2a) that had been separated from patients with fulminant hepatic failure was obtained from a JFH-1 clone containing the full-length genomic cDNA of the virus strain. The DNA was inserted downstream of T7 RNA promoter sequence that had been inserted in pUC19 plasmid. The thus constructed plasmid DNA is hereinafter referred to as pJFH1. Similarly, DNA corresponding to the entire region of viral genome of hepatitis C virus JCH-1 strain (genotype 2a) that had been separated from patients with chronic hepatitis was obtained from a JCH-1 clone containing the full-length genomic cDNA of the virus strain. The DNA was inserted downstream of the T7 RNA promoter sequence that had been inserted in pUC19 plasmid. The thus constructed plasmid DNA is hereinafter referred to as pJCH1. In addition, the preparation of the above JFH1 clone and JCH-1 clone is described in JP Patent Publication (Kokai) No. 2002-171978 A and Kato et al., J. Med. Virol., (2001) 64(3) pp. 334-339. Moreover, the nucleotide sequence of the full-length cDNA of JFH-1 clone was registered at the International DNA Data Bank (DDBJ/EMBL/GenBank) under accession No. AB047639, and the nucleotide sequence of the full-length cDNA of the JCH-1 clone under accession No. AB047640.

Figure 1:
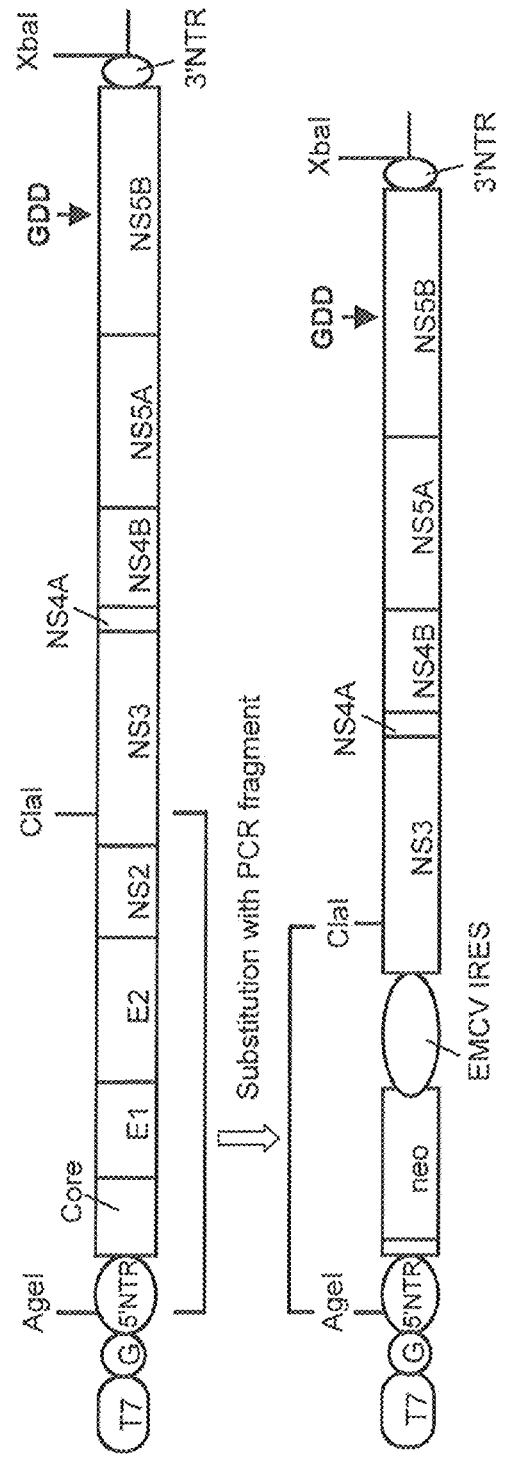
FIG. 1 is a schematic view showing procedures for constructing a template DNA for preparing the HCV-RNA replicon according to the present invention. The upper section of FIG. 1 shows the structure of the region within pJFH1 or pJCH1, with the viral genome inserted into it. The lower section of FIG. 1 shows the structure of the region within plasmid DNA pSGREP-JFH1 or pSGREP-JCH1, with the viral genome inserted into it, that had been constructed by substituting a part of viral genome-inserted region of pJFH1 or pJCH1 with a DNA fragment containing a neomycin resistance gene and EMCV IRES. Symbols in FIG. 1 are as described below. T7, T7 RNA promoter; G, dGTP that was inserted upstream of the 5' end of the inserted DNA derived from JFH-1 or JCH-1 and downstream of the 3' end of T7 RNA promoter sequence; 5' NTR, 5' untranslated region; Core, core protein; and 3' NTR, 3' untranslated region. E1 and E2 represent envelope proteins. NS2, NS3, NS4A, NS4B, NS5A and NS5B represent non-structural proteins. Age I, Cla I and Xba I represent cleavage sites of restriction enzymes Age I, Cla I and Xba I, respectively. GDD, the position of amino acid motif GDD corresponding to the active center of NS5B protein; neo, neomycin resistance gene; and EMCV IRES, internal ribosome entry site of encephalomyocarditis virus (EMCV IRES).

The structures of the thus constructed plasmid DNA pJFH1 and pJCH1 are shown in the upper section of FIG. 1. "T7" represents T7 RNA promoter, and "G" represents dGTP inserted upstream of the 5' end of the inserted JFH-1- or JCH-1-derived DNA and downstream of the 3' end of T7 RNA promoter sequence. A region from "5' NTR" to "3' NTR" is DNA corresponding to the entire genomic region of hepatitis C virus.

Next, the structural regions and a part of the non-structural regions of plasmid DNA pJFH1 and pJCH1 were substituted with a neomycin resistance gene (neo; also referred to as a neomycin phosphotransferase gene) and EMCV-IRES (internal ribosome entry site of encephalomyocarditis virus), thereby constructing plasmid DNA pSGREP-JFH1 and pSGREP-JCH1, respectively (lower section of FIG. 1). This construction procedure was conducted according to a previous report (Lohmann et al., Science, (1999) 285, pp. 110-113). Specifically, plasmid pJFH1 and pJCH1 were cleaved with restriction enzymes Age I and Cla I, and between the Age I and Cla I restriction sites, the following fragments were inserted to be ligated; a fragment was prepared by binding of a sequence ranging from 5' NTR to Core region derived from pJFH-1 with the neomycin resistance gene derived from pRSV5NEO by PCR amplification and then cleaving it with restriction enzymes Age I and Pme I, and, a fragment was prepared by binding of sequences ranging from EMCV IRES to NS3 region by PCR amplification and then cleaving it with restriction enzymes Pme I and Cla I.

Moreover, a mutation that mutates an amino acid motif GDD to GND, corresponding to the active center of RNA polymerase encoded by the NS5B region, was introduced into the NS5B region in pSGREP-JFH1, thereby preparing a mutant plasmid clone pSGREP-JFH1/GND.

Moreover, a mutation that results in the deletion of a sequence of 10 continuous amino acids containing an amino acid motif GDD corresponding to the active center of RNA polymerase encoded by the NS5B region was introduced into the NS5B region in pSGREP-JFH1, thereby preparing a mutant plasmid clone pSGREP-JFH1/dGDD.

The above-prepared mutant clones pSGREP-JFH1/GND and pSGREP-JFH1/dGDD cannot express active NS5B protein, which is required for the replication of replicon RNA, because the amino acid sequence of the active site of NS5B protein encoded by these clones has mutated.

(B) Preparation of Replicon RNA

To prepare template DNA for use in synthesis of replicon RNA, the above-constructed expression vectors pSGREP-JFH1, pSGREP-JCH1, pSGREP-JFH1/GND and pSGREP-JFH1/dGDD were each cleaved with a restriction enzyme Xba I.

Subsequently, 10 to 20 µg each of these Xba I-cleaved fragments was contained in 50 µl of a reaction solution, and then further treated by 30 minutes of incubation at 30° C. with 20 U of Mung Bean Nuclease. Mung Bean Nuclease is an enzyme catalyzing a reaction for selectively degrading a single-stranded portion of double-stranded DNA. Generally, when RNA synthesis is performed using directly the above Xba I-cleaved fragment as a template, a replicon RNA having four nucleotides of CUGA, a part of the recognition sequence of Xba I, excessively added to the 3' terminus would be synthesized. Hence, in this example, Xba I-cleaved fragments were treated with Mung Bean Nuclease, so as to remove the four nucleotides of CUGA from the fragments. The solutions containing Xba I-cleaved fragments, which had been treated with Mung Bean Nuclease, were treated to remove proteins according to a general method, so that Xba I-cleaved fragments, from which the four nucleotides of CUGA had been removed, were purified and used as template DNAs.

Next, from the template DNA, RNA was synthesized in vitro using T7 RNA polymerase. For this RNA synthesis, MEGAscript from Ambion, Inc. was used. Reaction was carried out using 20 µl of a reaction solution containing 0.5 to 1.0 micrograms of the template DNA according to the instructions of the manufacturer.

After completion of RNA synthesis, DNase (2 U) was added to the reaction solution to conduct reaction at 37° C. for 15 minutes. RNA extraction using acidic phenol was further performed to remove the template DNA. RNAs (replicon RNAs) synthesized in this manner from the above template DNAs derived from pSGREP-JFH1, pSGREP-JCH1, pSGREP-JFH1/GND and pSGREP-JFH1/dGDD were respectively named rSGREP-JFH1, rSGREP-JCH1, rSGREP-JFH1/GND and rSGREP-JFH1/dGDD. Regarding the nucleotide sequences of these replicon RNAs, the nucleotide sequence of rSGREP-JFH1 is shown in SEQ ID NO: 1 and FIG. 2A to F, that of rSGREP-JCH1 is shown in SEQ ID NO: 2 and FIG. 3A to F, that of rSGREP-JFH1/GND is shown in SEQ ID NO: 7, and that of rSGREP-JFH1/dGDD is shown in SEQ ID NO: 8.

Example 2

Establishment of Replicon-Replicating Cell Clone (C) Transfection of Replicon RNA, Determination of Colony-Forming Ability of Transfected Cells and Establishment of Cell Clones Each of the above-synthesized replicon RNAs (rSGREP-JFH1, rSGREP-JCH1, rSGREP-JFH1/GND and rSGREP-JFH1/dGDD) was mixed in different quantities with total cellular RNA extracted from Huh7 cells so as to have a total RNA quantity of 10 µg. Subsequently, the mixed RNA was introduced into Huh7 cells by the electroporation method. The Huh7 cells subjected to the electroporation treatment were seeded into culture dishes, and then cultured for 16 hours to 24 hours. G418 (neomycin) was then added to the culture dishes at different concentrations. Thereafter, culture was continued while exchanging the culture solutions twice a week. After 21 days of culture following seeding, surviving cells were stained with crystal violet. The number of stained colonies was counted, and then the number of colonies obtained per µg of the transfected replicon RNA was calculated.

For rSGREP-JFH1 or rSGREP-JCH1-transfected cells, for which colony formation had been observed, colonies of the surviving cells were further cloned from the above culture dishes after 21 days of culture, and were continuously cultured. By such cloning of colonies, several strains of cell clones could be established.

For the established cell clones, detection of the replicated replicon RNA, confirmation of the presence or the absence of the incorporation of the neomycin resistance gene into the host genomic DNA, and confirmation of the expression of HCV proteins were performed as described later, in Example 4. Cell clones for which the replication of the replicon had been confirmed in the cells were regarded as replicon-replicating cell clones.

(D) Colony-Forming Ability in Each Transfected Cell

As a result of the above transfection, for rSGREP-JFH1-transfected Huh7 cells, the colony-forming ability per μg of the transfected replicon RNA was 94700 CFU (Colony Forming Unit)/μg·RNA when G418 concentration was 1.0 mg/ml (the left column in FIG. 4). In contrast, colony formation was not observed in the Huh7 cells, into which rSGREP-JFH1/dGDD and rSGREP-JFH1/GND had each been transfected (the central column and the right column in FIG. 4). This suggests that the colony-forming ability confirmed for the Huh7 cells, into which rSGREP-JFH1 replicon RNA had been transfected, depends on the activity of NS5B (RNA polymerase) expressed by rSGREP-JFH1. Specifically, it was considered that in cells that had formed colonies, rSGREP-JFH1 replicon RNA autonomously replicated due to the action of NS5B expressed by rSGREP-JFH1, and the neomycin resistance gene was continuously expressed to maintain G418 resistance, so that cell growth was enabled.

On the other hand, in the Huh7 cells, into which rSGREP-JCH1 had been transfected, no colony formation was observed in the case of 1 to 0.5 mg/ml G418 concentrations (FIG. 5). When G418 concentration was lowered to 0.25 mg/ml, colony formation was observed in the Huh7 cells, into which rSGREP-JCH1 had been transfected as well.

Furthermore, Xba I-cleaved fragment of the expression vector pSGREP-JFH1 obtained in (B) above was used as a template DNA for RNA synthesis without treating the fragment with Mung Bean Nuclease, so as to synthesize replicon RNA. This replicon RNA was transfected to Huh7 cells in a manner similar to that in (C) above. The replicon RNA that had been prepared without performing Mung Bean Nuclease treatment had the four nucleotides of CUGA excessively added to the 3' terminus.

As a result, the colony-forming ability of the Huh7 cells, into which the replicon RNA prepared without treatment with Mung Bean Nuclease had been transfected, decreased to 512 CFU/μg·RNA (the left side in FIG. 6). This result revealed that the sequence on the 3' terminus of the replicon RNA affects the colony-forming ability of the transfected cells.

Example 3

(E) Re-Transfection of Replicated Replicon RNA Derived from Replicon-Replicating Cells From the replicon-replicating cell clones that had been established by transfection of rSGREP-JFH1 into Huh7 cells according to descriptions of Example 2, total RNA was extracted by a standard procedure. The number of copies of the replicated replicon RNA contained in the cellular RNA was determined by Northern blot analysis and a quantitative RT-PCR method.

Northern blot analysis was performed according to the description in Molecular Cloning, A laboratory Manual, $2^{nd}$ edition, J. Sambrook, E. F. Fritsch, T. Maniatis, Cold Spring Harbor Laboratory Press (1989). Specifically, RNA extracted from the cells was subjected to denaturing agarose electrophoresis. After electrophoresis, the RNA was transferred onto a positively charged nylon membrane. The $^{32}$P-labeled DNA or RNA probe prepared from pSGREP-JFH1 was hybridized to the RNA transferred to the membrane as described above. Next the membrane was washed, and then exposed to a film, so as to detect a replicon-specific RNA band.

Detection of the replicon RNA by quantitative RT-PCR was conducted by detecting the 5' untranslated region RNA within HCV RNA according to Takeuchi T, Katsume A, Tanaka T, Abe A, Inoue K, Tsukiyama-Kohara K, Kawaguchi R, Tanaka S and Kohara M., Real-time detection system for quantification of Hepatitis C virus genome, Gastroenterology 116: 636-642 (1999). Specifically, the replicon RNA contained in RNA extracted from the cells was amplified by PCR using synthetic primers: R6-130-S17, 5'-CGGGAGAGC-CATAGTGG-3' (SEQ ID NO: 13) and R6-290-R19, 5'-AG-TACCACAAGGCCTTTCG-3' (SEQ ID NO: 14); TaqMan Probe; R6-148-S21FT, 5'-CTGCGGAACCGGTGAGTA-CAC-3' (SEQ ID NO: 15) and an EZ rTth RNA PCR kit, and then detected using an ABI Prism 7700 sequence detector system.

Next, aliquots of total cellular RNAs extracted from clone 6 (among the above-mentioned replicon-replicating cell clones) and pool clones (prepared by collecting replicon-replicating cells that had formed colonies from whole one dish and culturing them) were each introduced into another Huh7 cells by retransfection. Total cellular RNA used for the transfection was prepared to contain $1 \times 10^7$ copies of replicon RNA based on the number of copies of the above-determined replicon RNA. Transfection was performed as described in (C) above, and then selective culture was performed under G418 concentration conditions of 1 mg/ml. Thus, the colony formation of the replicon-replicating cells was observed (FIG. 7). The colony-forming ability in this case was 1 colony or more per $1 \times 10^6$ copies of the replicon RNA used for transfection, when it was calculated from the number of colonies obtained.

On the other hand, the number of copies of in vitro synthetic RNA that had been synthesized in vitro using pSGREP-JFH1 as a template and T7 RNA polymerase was approximately $2 \times 10^{11}$ copies/μg·RNA, when calculated based on the weight and the length of the RNA. The colony-forming ability in the case of using the in vitro synthetic RNA for transfection in a manner similar to the above method was 1 colony per $5 \times 10^7$ copies. These results revealed that when RNA derived from cells extracted from replicon-replicating cells and in vitro synthetic RNA were each transfected to Huh7 cells as replicon RNA in the same number of copies, the use of the replicon RNA replicated within Huh7 cells resulted in colony-forming ability approximately 50 times higher than that of the in vitro synthetic RNA.

Example 4

(F) Detection of Replicon RNA

According to (E) above, cell clones [clones Nos. 1 to 11] were established by retransfection of total RNA that had been obtained from the replicon-replicating cell clone established by transfection of rSGREP-JFH1 to Huh7 cells to another Huh7 cells. From the established cell clones and pool clones (prepared by collecting cell clones that had formed colonies from whole one dish and then culturing them), respectively, total RNAs were extracted by an acidic phenol extraction method. Subsequently the total RNAs were analyzed by the Northern blot method using a pSGREP-JFH1-specific probe as a probe. As control, total RNA extracted similarly from untransfected Huh7 cells (in FIG. 8, denoted as "Huh7"), a sample prepared by adding $10^7$ copies of replicon RNA synthesized in vitro to the total RNA extracted from Huh7 cells (in FIG. 8, denoted as "$10^7$"), and a sample (in FIG. 8, denoted as "$10^8$") prepared by adding $10^8$ copies of replicon RNA synthesized in vitro to the total RNA extracted from Huh7 cells, were used. In FIG. 8, 1 to 11 represent cell clone Numbers.

As a result, RNA of approximately the same size as that of rSGREP-JFH1 was detected using a pSGREP-JFH1-specific probe (FIG. 8). Thus, it was confirmed that the replicon RNA from rSGREP-JFH1 that had been transfected at the beginning replicated and proliferated within the cell clones. In addition, it was shown that the cell clones differed from each other in the quantity of the replicated replicon RNA. In FIG. 8, for example, clones 2, 6, 9 and 10 contained high quantities of the replicated replicon RNA, and clones 4, 8 and 11 contained low quantities of the replicated replicon RNA.

(G) Confirmation of the Presence or the Absence of the Incorporation of a Neomycin Resistance Gene into Genomic DNA For the cell clones that had been obtained by retransfection of replicon RNA as described in Example 3, PCR amplification was performed using neomycin resistance gene-specific primers; sense primer, NEO-S3: 5'-AACAAGATGGATTG-CACGCA-3' (SEQ ID NO: 16) and antisense primer, NEO-R: 5'-CGTCAAGAAGGCGATAGAAG-3' (SEQ ID NO: 17), and the host cellular genomic DNA extracted from each of the cell clones as a template, in order to confirm that the resistance of each of the cell clones against G418 was not due to the incorporation of the neomycin resistance gene into the genome. The cell clones used herein were the cell clones Nos. 1 to 8 obtained by retransfection of rSGREP-JFH1-derived replicated replicon RNA (rSGREP-JFH1-derived cell clones Nos. 1 to 8), and cell clones Nos. 1 to 6 obtained by retransfection of rSGREP-JCH1-derived replicated replicon RNA (rSGREP-JCH1-derived cell clones Nos. 1 to 6). As a result, as shown in FIG. 9, in the eight examined rSGREP-JFH1-derived cell clones, positive clones showing the amplification of the neomycin resistance gene were not observed. For rSGREP-JCH1-derived cell clones, only 1 out of the 6 examined clones was positive (in FIG. 9, lane 3 in the right photograph). It was considered that this positive clone had acquired G418 resistance by the incorporation of the neomycin resistance gene in rSGREP-JCH1-derived replicated replicon RNA into the genomic DNA of the host cells. Thus, in the positive clone, unlike other clones, it was thought that the replicon RNA itself did not autonomously replicate within the cells. This was confirmed by the results of the experiment shown in the next (H) that no HCV proteins were detected from the positive clone.

(H) Detection of HCV Protein

Protein was extracted from rSGREP-JFH1- and rSGREP-JCH1-transfected cell clones by a standard procedure, and then analyzed by SDS-PAGE and Western blot method (FIG. 10). The examined cell clones were the same as those used in (G) above: rSGREP-JFH1-derived cell clones Nos. 1 to 8 and rSGREP-JCH1-derived cell clones Nos. 1 to 6. In addition, a cellular extract from the cell obtained by transiently transfecting expression plasmid DNA containing NS3 gene into Huh7 cells was regarded as a positive control (NS3 protein). Furthermore, a protein extracted from the untransfected Huh7 cells was used as a negative control. A protein sample extracted from each cell clone was blotted onto a PVDF membrane (Immobilon-P, Millipore), and then detection of NS3 protein encoded by replicated replicon RNA was performed using anti-NS3-specific antibody (provided by Dr. Moradpour; Wolk B, et al, J. Virology. 2000, 74: 2293-2304). As shown in FIG. 10, in rSGREP-JFH1-derived cell clones Nos. 1 to 8 and rSGREP-JCH1-derived cell clones Nos. 1, 2 and 4 to 6, proteins of the same size as those of the positive control were detected. In rSGREP-JCH1-derived cell clone No. 3 (the clone detected as a positive clone in (G) above), no expression of NS3 protein was detected. That is, in rSGREP-JCH1-derived cell clone No. 3, no replication of replicon RNA was confirmed. NS3 protein was not detected in the untransfected Huh7 cells, revealing that in cell clones wherein NS3 protein was detected, the transfected replicon RNA autonomously replicated so that NS3 protein was expressed.

Moreover, by the use of the serum of a hepatitis C patient as an antibody, the expression of NS5a protein from the replicon RNA was also confirmed in each cell clone for which the expression of NS3 protein had been confirmed as described above.

Based on the results of (G) and (H) above, it was confirmed that replicon RNAs were replicated in the cell clones established by transfection of the replicon RNA.

Example 5

(I) Analysis of Adaptive Mutation

According to descriptions of Example 3, total RNA obtained from the replicon-replicating cell clones established through the transfection of rSGREP-JFH1 into Huh7 cells was re-transfected to another Huh7 cells, thereby establishing 21 cell clones. Total RNA was extracted from each of these cell clones by a standard procedure. cDNA corresponding to the replicon RNA was synthesized using the total RNA as a template, reverse transcriptase Superscript II (Invitrogen) and primer 9641R-IH (5'-GCACTCTCTGCAGTCATGCGGCT-CACGGAC-3' (SEQ ID NO: 18)). The composition of a reaction solution for the synthesis of cDNA by reverse transcription reaction is as shown below.

| Composition of Reaction Solution | Fluid Volume (μl) |
|---|---|
| 5x 1st strand Buffer | 4 |
| 2 mM dNTP | 5 |
| 0.1M DTT | 1 |
| 9651R-IH primer (100 μM) | 1 |
| DW (distilled water) | 6.5 |
| Sample RNA (2 mg/mL) | 1 |
| RNasin (Promega) (40 U/μL) | 0.5 |
| Superscript II RT (Invitrogen) | 1 |
| Total | 20 μl |

In cDNA synthesis reaction, the above reagents other than RNasin and Superscript II were mixed to prepare a first reaction solution. The solution was heated at 90° C. for 3 minutes, and then cooled on ice. Subsequently, RNasin and Superscript II were added to this reaction solution, and then the solution was allowed to react at 42° C. for 1 hour, followed by another reaction at 70° C. for 15 minutes.

Furthermore, PCR amplification was performed using the thus obtained cDNA together with five primer sets by the following procedures, so that DNA amplification fragments covering almost all the regions of the replicon RNA were obtained. The primer sets used and regions amplified by each primer set are shown in Table 1 and Table 2 below.

TABLE 1

| Designation of amplified fragment | Primer set | | Amplified region |
|---|---|---|---|
| | Primer 1 | Primer 2 | |
| A/ | 42S-IH | 433R-neo | 41-470 |
| B/ | C/S17ssp | 4680R-IH | 28-3026 |
| C/ | 4534S-IH | 7279R-IH | 2880-5625 |
| D/ | 7198S-IH | 9367R-IH | 5544-7713 |
| E/ | 9247S-NF | 9576R-NF | 7597-7960 |

In Table 1, an amplified region is represented by nucleotide numbers in rSGREP-JFH1 (SEQ ID NO: 1) that the region corresponds to.

TABLE 2

| Primer designation | Nucleotide sequence (5'→3') | SEQ ID NO: |
|---|---|---|
| 42S-IH | CCCCTGTGAGGAACTACTGTCTTCACGC | SEQ ID NO: 19 |
| C/S17ssp | CCGGGAGAGCCATAGTGGTCTGCG | SEQ ID NO: 20 |
| 4534S-IH | CCACTCAAAGAAAAAGTGTGACGAGCTCGC | SEQ ID NO: 21 |
| 7198S-IH | GGCTTGGGCACGGCCTGA | SEQ ID NO: 22 |
| 9247S-NF | GCGGTGAAGACCAAGCTCAAACTCACTCCA | SEQ ID NO: 23 |
| 433R-neo | AGAACCTGCGTGCAATCCATC | SEQ ID NO: 24 |
| 4680R-IH | CCCGTCATGAGGGCGTCGGTGGC | SEQ ID NO: 25 |
| 7279R-IH | ACCAGCAACGGTGGGCGGTTGGTAATC | SEQ ID NO: 26 |
| 9367R-RI | GGCACGCGACACGCTGTG | SEQ ID NO: 27 |
| 9576R-NF | AGCTAGCCGTGACTAGGGCTAAGATGGAGC | SEQ ID NO: 28 |

The composition of a reaction solution in this PCR reaction is as follows.

| Composition of Reaction Solution | Fluid Volume (µl) |
|---|---|
| Primer 1 (10 µM) | 1.0 |
| Primer 2 (10 µM) | 1.0 |
| 2.5 mM dNTPs | 5.0 |
| 10x LA Buffer | 5.0 |
| MgCl$_2$ (25 mM) | 5.0 |
| LA Taq (TAKARA) (5 U/µl) | 0.3 |
| DW (distilled water) | 30.7 |
| Template cDNA | 2.0 |
| Total | 50 µl |

In addition, PCR reaction conditions are as follows: 95° C. for 2 minutes; 35 cycles of 98° C. for 10 seconds and then 68° C. for 8 minutes; and 72° C. for 7 minutes; after which the temperature is kept at 4° C.

The nucleotide sequence of each PCR product obtained as described above was determined, and then the RNA sequence corresponding to the DNA sequence was compared with the sequence of rSGREP-JFH1. The results are shown in Table 3.

TABLE 3

| Region | Synonymous substitution | Nonsynonymous substitution | Total number of mutations |
|---|---|---|---|
| NS3 | 0 | 5 | 5 |
| NS4A | 0 | 2 | 2 |
| NS4B | 0 | 3 | 3 |
| NS5A | 0 | 7 | 7 |
| NS5B | 3 | 5 | 8 |
| Total | 3 | 22 | 25 |

As shown in Table 3, total number of nucleotide mutations observed in 21 cell clones was 25. 22 of these mutations were nonsynonymous substitutions inducing amino acid mutation. Types of these mutations are as shown in Table 4. In addition, the positions of these mutations in the non-structural region are shown in FIG. 11.

TABLE 4

| Clone designation | Mutation site | | | |
|---|---|---|---|---|
| | Nucleotide No. | Nucleotide mutation | Amino acid mutation | Amino acid No. |
| C1 | 7098 | A⇒G | None | |
| | 7157 | A⇒G | Y⇒C | 2824 |
| C2 | 4955 | C⇒U | A⇒V | 2090 |
| C3 | 4936 | A⇒G | T⇒A | 2084 |
| | 5000 | A⇒G | Y⇒C | 2105 |
| | 7287 | A⇒G | None | |
| | 7288 | A⇒G | M⇒V | 2868 |
| C4 | 5901 | G⇒U | E⇒D | 2405 |
| | 6113 | A⇒U | H⇒L | 2476 |
| C5 | 2890 | A⇒G | K⇒E | 1402 |
| C6 | 7209 | A⇒G | None | |

In Table 4 and FIG. 11, "C1 to C6" represent replicon-replicating cell clones C1 to C6 having replicon RNA found to have mutations. "Nucleotide No." shows the corresponding nucleotide numbers within the nucleotide sequence of replicon RNA rSGREP-JFH1 (SEQ ID NO: 1). "Amino acid No." shows the corresponding amino acid numbers within the amino acid sequence encoded by the JFH-1 clone (SEQ ID NO: 4). The types of nucleotides and amino acids at mutation sites are described according to their general notations. As shown in Table 4, in clone C2, a nucleotide corresponding to nucleotide No. 4955 of SEQ ID NO: 1 on the replicon RNA mutated from C (cytosine) to U (uracil), which results in a mutation of an amino acid corresponding to amino acid No. 2090 of SEQ ID NO: 4 from A (alanine) to V (valine).

Furthermore, mutation positions shown in FIG. 11 are shown with bar lines with the nucleotide numbers shown in Table 4. A thick bar line represents nonsynonymous substitution, and a thin bar line represents synonymous substitution.

There were 2 clones having no nucleotide mutations at all that cause amino acid mutations. When Northern blot analysis was conducted for the 2 clones, it was shown that in these 2 clones, the quantity of replicon RNAs replicated was lower than those in the cell clones that had replicated replicon RNAs having a nucleotide mutation that causes an amino acid mutation. Hence, it was considered that the nucleotide mutation causing an amino acid mutation within the replicon RNA was an adaptive mutation for increasing the replication efficiency of the replicon RNA in Huh7 cells.

Example 6

(J) Establishment of Replicon-Replicating Cell Clone Using Cells Other than Huh7 Cells According to the method described in Example 1, rSGREP-JFH1 was transfected into some hepatic cancer cells other than Huh7 cells and non-liver-derived cells. The transfected cells were seeded into culture dishes and then cultured. Colony formation was observed and the number of colonies was counted. The cells used for transfection are as follows.
(1) HepG2 cells (representative hepatic cancer cells as well as Huh7 cells)
(2) IMY-N9 cells (established by Ito et al; fusion cells of HepG2 cells and human primary culture hepatic cells (Hepatology 2001, 34: 566-572))
(3) HeLa cells (human cervical cancer-derived cells (Can Cer Res. 1952, 12: 264-265))
(4) 293 cells (human fetal kidney-derived cells (Gen. Virol. 1977, 36: 59-72))

The results of transfection using HepG2 cells, IMY-N9 cells, HeLa cells or 293 cells, respectively, are shown in FIG. 12A to D. As shown in FIG. 12A to D, all HepG2 cells, IMY-N9 cells, HeLa cells, and 293 cells showed colony formation for rSGREP-JFH1-transfected cells.

For the established cell clones, detection of the replicated replicon RNA, confirmation of the presence or the absence of the incorporation of the neomycin resistance gene into host genomic DNA, and confirmation of the expression of HCV protein were performed as described later, (L) and (M). The cell clones, for which the replication of the replicon in the cells had been confirmed, were regarded as replicon-replicating cell clones. Specifically, it was demonstrated that the use of rSGREP-JFH1 also enables the preparation of HCV replicon-replicating cells using hepatic cancer cells other than Huh7 cells and non-hepatic cells with which the production of HCV replicon-replicating cells had previously been unsuccessful (Blight et al., Science, (2000) 290; 1972-1974).

(K) Detection of Replicon RNA in Replicon-Replicating Cells Using Cells Other than Huh7 Cells Northern blot analysis was conducted according to a description of Molecular Cloning, A laboratory Manual, 2nd edition, J. Sambrook, E. F. Fritsch, T. Maniatis, Cold Spring Harbor Laboratory Press (1989). In accordance with the descriptions of the previous section (J), total RNA was extracted by the acidic phenol extraction method from each of the replicon-replicating cell clones that had been established by transfection of rSGREP-JFH1 into HepG2, IMY-N9 or HeLa cells respectively, and from pool clones of the replicon-replicating cells that had been established through transfection of rSGREP-JFH1 into 239 cells (prepared by collecting cell clones that had formed colonies from whole one dish and culturing them). Next, the total RNAs were analyzed by the Northern blot method using a pSGREP-JFH1-specific probe as a probe. As controls, total RNAs (lanes 1 and 17 in FIG. 13) extracted similarly from untransfected Huh7 cells and HepG2 cells, and RNA (lanes 2 and 3 in FIG. 13) prepared by adding $10^7$ copies or $10^8$ copies of the replicon RNA synthesized in vitro to total RNA extracted from Huh7 cells were used. As a result, RNA of approximately the same size of that of rSGREP-JFH1 was detected using a pSGREP-JFH1-specific probe (FIG. 13). Accordingly, it was confirmed that the replicon RNA derived from rSGREP-JFH1 that had been transfected at the beginning was replicated and proliferated within the cell clone. Furthermore, it was also revealed that the quantities of replicated replicon RNAs differed depending on cell type, and IMY-N9 cells were found to replicate the replicon RNA particularly efficiently. Moreover, it was revealed that the clones differed from each other in the quantity of the replicated replicon RNA.

(L) Confirmation of the Presence or the Absence of the Incorporation of the Neomycin Resistance Gene into Genomic DNA For the thus established replicon RNA-replicating cell clone, PCR amplification was performed using neomycin resistance gene-specific primers (sense primer, NEO-S3: 5'-AACAAGATGGATTGCACGCA-3' (SEQ ID NO: 29), antisense primer, NEO-R: 5'-CGTCAAGAAGGCGATA-GAAG-3' (SEQ ID NO: 30)) and the host cellular genomic DNA extracted from each of the cell clones as a template, in order to confirm that the resistance of each of the cell clones against G418 was not due to the incorporation of the neomycin resistance gene into the genome. The cell clones used herein were the cell clones Nos. 1, 5, 7, 8, 9, 10, 11, 12 and 13 obtained by retransfection of rSGREP-JFH1-derived replicated replicon RNA into HepG2 cells, and the cell clones Nos. 3, 4, 5, 6, 7, 8, 9, 10 and 11 obtained by retransfection of rSGREP-JFH1-derived replicated replicon RNA into IMY-N9 cells. As a result, as shown in FIG. 14, in the nine examined cell clones obtained by introduction of rSGREP-JFH1 into HepG2 cells, a positive clone showing the amplification of the neomycin resistance gene was not observed. In the 9 examined cell clones obtained by introduction of rSGREP-JFH1 into IMY-N9 cells, a positive clone showing the amplification of the neomycin resistance gene was not observed.

A similar examination was performed for cell clones obtained by retransfection of rSGREP-JFH1-derived replicated replicon RNA into HeLa cells, and cell clones obtained by retransfection of rSGREP-JFH1-derived replicated replicon RNA into 293 cells. Then, a positive clone showing the amplification of the neomycin resistance gene was not observed.

(M) Detection of HCV Protein

Proteins were extracted from the established cell clones by a standard procedure, and then analyzed by SDS-PAGE and the Western blot method (FIG. 15). The cell clones examined in this case were the same as those used in the above section: the cell clones Nos. 1, 5, 7, 8, 9, 10, 11, 12 and 13 obtained by retransfection of rSGREP-JFH1-derived replicated replicon RNA into HepG2 cells, and the cell clones Nos. 3, 4, 5, 6, 7, 8, 9, 10 and 11 obtained by retransfection of rSGREP-JFH1- derived replicated replicon RNA into IMY-N9 cells. Furthermore, according to a previous report (Lehmann et. al., Science, (1999)), the HCV RNA replicon-replicating cell clone prepared by introducing rSGREP-JFH1 into HuH7 was regarded as a positive control (FIG. 15, lane 4-1, C6). Moreover, a protein extracted from untransfected cells was used as a negative control (FIG. 15, lane N). Protein samples extracted from each cell clone were blotted onto PVDF membranes (Immobilon-P, Millipore), and then detection of NS3 protein encoded by the replicated replicon RNA was performed using anti-NS3-specific antibody (provided by Dr. Moradpour; Wolk B, et al, J. Virology, 2000, 74: 2293-2304). As shown in the upper section in FIG. 15, a protein of the same size as that of the positive control was detected in the cell clones Nos. 1, 5, 7, 8, 9, 10, 11, 12 and 13 obtained by retransfection of rSGREP-JFH1-derived replicated replicon RNA, and in the cell clones Nos. 3, 4, 5, 6, 7, 8, 9, 10 and 11 obtained by retransfection of rSGREP-JFH1-derived replicated replicon RNA into IMY-N9 cells.

Moreover, by the use of the serum of a hepatitis C patient as an antibody, the confirmation of the expression of NS5a protein from the replicon RNA was performed for each cell clone that had been confirmed above to express NS3 protein. In this experiment, examination was performed in a manner similar to that in the case of the expression of NS3 protein, except using anti-NS5a antibody instead of the serum of the patient. As a result, as shown in the lower section in FIG. 15, a protein of the same size as that of the positive control was detected in the cell clones Nos. 1, 5, 7, 8, 9, 10, 11, 12 and 13 obtained by retransfection of rSGREP-JFH1-derived replicated replicon RNA, and the cell clones Nos. 3, 4, 5, 6, 7, 8, 9, 10 and 11 obtained by retransfection of rSGREP-JFH1-derived replicated replicon RNA into IMY-N9 cells.

When similar examination was performed for the cell clones obtained by retransfection of rSGREP-JFH1-derived replicated replicon RNA into HeLa cells, and the cell clones obtained by retransfection of rSGREP-JFH1-derived replicated replicon RNA into 293 cells, the expression of NS3 and that of NS5a proteins could be confirmed.

As described above, it was confirmed that the replicon RNA was replicated in the cell clones that had been established through transfection of the replicon RNA.

Example 7

(N) Analysis of Adaptive Mutation

According to the descriptions of Example 3, total RNAs obtained from the replicon-replicating cell clones established through the transfection of rSGREP-JFH1 into HepG2 and HeLa cells were re-transfected into another cells of the each cell line, respectively, so that 14 cell clones were established for HepG2 cells and 8 cell clones were established for HeLa cells. From each of these cell clones, total RNA was extracted by a standard procedure. cDNA corresponding to the replicon RNA was synthesized using the total RNA as a template, reverse transcriptase Superscript II (Invitrogen) and a primer 9641R-IH (5'-GCACTCTCTGCAGTCATGCGGCTCACG-GAC-3' (SEQ ID NO: 31)). The composition of a reaction solution for the synthesis of cDNA by reverse transcription reaction is as shown below.

| Composition of Reaction Solution | Fluid Volume (μl) |
|---|---|
| 5x 1st strand Buffer | 4 |
| 2 mM dNTP | 5 |
| 0.1M DTT | 1 |
| 9651R-IH primer (100 μM) | 1 |
| DW (distilled water) | 6.5 |
| Sample RNA (2 mg/mL) | 1 |
| RNAsin (Promega)(40 U/μL) | 0.5 |
| Superscript II RT (Invitrogen) | 1 |
| Total | 20 μl |

In cDNA synthesis reaction, the above reagents other than RNAsin and Superscript II were mixed to prepare a first reaction solution. The first reaction solution was heated at 90° C. for 3 minutes, and then cooled on ice. Subsequently, RNAsin and Superscript II were added to the reaction solution, and then the solution was allowed to react at 42° C. for 1 hour, followed by another reaction at 70° C. for 15 minutes.

Furthermore, PCR amplification was performed using the thus obtained cDNA together with five primer sets by the following procedures, so that DNA amplification fragments covering almost all the regions of replicon RNA were obtained. The primer sets used and regions amplified by each primer set are shown in Table 5 and Table 6 below.

TABLE 5

| Designation of amplified fragment | Primer set | | Amplified region |
|---|---|---|---|
| | Primer 1 | Primer 2 | |
| A | 42S-IH | 433R-neo | 41-470 |
| B | C/S17ssp | 4680R-IH | 28-3026 |
| C | 4534S-IH | 7279R-IH | 2280-5625 |
| D | 7198S-IH | 9367R-IH | 5544-7713 |
| E | 9247S-NF | 9576R-NF | 7597-7966 |

In this table, an amplified region is represented by nucleotide numbers in rSGREP-JFH1 (SEQ ID NO: 1) that the region corresponds to.

TABLE 6

| Primer Designation | Nucleotide Sequence (5' to 3') | SEQ ID NO: |
|---|---|---|
| 43S-IH | CCCCTGTGAGGAACTACTGTCTTCACGC | SEQ ID NO: 32 |
| C/S17ssp | CCGGGAGAGCCATAGTGGTCTGCG | SEQ ID NO: 33 |
| 4534S-IH | CCACTCAAAGAAAAAGTGTGACGAGCTCGC | SEQ ID NO: 34 |
| 7198S-IH | GGCTTGGGCACGGCCTGA | SEQ ID NO: 35 |
| 9247S-NF | GCGGTGAAGACCAAGCTCAAACTCACTCCA | SEQ ID NO: 36 |
| 433R-neo | AGAACCTGCGTGCAATCCATC | SEQ ID NO: 37 |
| 4680R-IH | CCCGTCATGAGGGCGTCGGTGGC | SEQ ID NO: 38 |
| 7279R-IH | ACCAGCAACGGTGGGCGGTTGGTAATC | SEQ ID NO: 39 |

TABLE 6-continued

| Primer Designation | Nucleotide Sequence (5' to 3') | SEQ ID NO: |
|---|---|---|
| 9367R-IH | GGAACGCGACACGCTGTG | SEQ ID NO: 40 |
| 9576R-NF | AGCTAGCCGTGACTAGGGCTAAGATGGAGC | SEQ ID NO: 41 |

The composition of a reaction solution in this PCR reaction is as follows.

| Composition of Reaction Solution | Fluid Volume (μl) |
|---|---|
| Primer 1 (10 μM) | 1.0 |
| Primer 2 (10 μM) | 1.0 |
| 2.5 mM dNTPs | 5.0 |
| 10x LA Buffer | 5.0 |
| MgCl$_2$ (25 mM) | 5.0 |
| LA Taq (TAKARA) (5 U/μl) | 0.3 |
| DW (distilled water) | 30.7 |
| Template cDNA | 2.0 |
| Total | 50 μl |

In addition, PCR reaction conditions are as follows: 95° C. for 2 minutes; 35 cycles of 98° C. for 10 seconds and then 68° C. for 8 minutes; followed by 72° C. for 7 minutes, after which the temperature is kept at 4° C.

The nucleotide sequence of each PCR product obtained as described above was determined, and then the RNA sequence corresponding to the DNA sequence was compared with the sequence of rSGREP-JFH1. The results are shown in Table 7 and Table 8.

TABLE 7

Analysis of adaptive mutation of JFH-1 replicon in HepG2 cells

| | Mutation site | | Mutation | |
|---|---|---|---|---|
| Clone | Nucleotide No. | Amino acid No. | Nucleotide | Amino acid |
| HepIH1 | 6826 | 2714 | C⇒A | Q⇒K |
| HepIH3 | 6887 | 2734 | C⇒A | T⇒N |
| HepIH5 | 6887 | | U⇒A | None |
| HepIH8 | 6580 | 2632 | U⇒A | S⇒T |
| | 7159 | 2825 | U⇒C | Y⇒H |
| HepIH9 | 3342 | | A⇒G | None |
| | 3594 | | C⇒A | None |
| | 7230 | 2848 | U⇒A | N⇒K |
| HepIH10 | 5052 | | U⇒C | None |
| | 6943 | 2753 | C⇒A | P⇒T |
| HepIH12 | None | | | |
| HepIH13 | 4302 | | C⇒U | None |
| | 5687 | 2334 | G⇒A | G⇒D |
| | 6110 | 2475 | A⇒G | Y⇒C |

As shown in Table 7, in the case of HepG2 cells, a total of 13 nucleotide mutations were observed in 8 cell clones, and 8 of these mutations were nonsynonymous substitutions that cause amino acid mutations. Types of these mutations are shown in Table 8. On the other hand, in the case of HeLa cells, a total of 7 nucleotide mutations were observed in 3 cell clones, and 5 of these mutations were nonsynonymous substitutions that cause amino acid mutations. Types of these mutations are shown in Table 8.

TABLE 8

Analysis of adaptive mutation of JFH-1 replicon in HeLa cells

| | Mutation site | | Mutation | |
|---|---|---|---|---|
| Clone | Nucleotide No. | Amino acid No. | Nucleotide | Amino acid |
| HeLaIH1 | None | | | |
| HeLaIH2 | 5550 | 2272 | U⇒C | S⇒P |
| | 6252 | | A⇒G | None |
| | 7182 | | U⇒C | None |
| | 7217 | 2844 | A⇒G | H⇒R |
| HeLaIH5 | 3643 | 1653 | A⇒G | M⇒V |
| | 5851 | 2389 | G⇒A | A⇒T |
| | 5914 | 2410 | G⇒A | E⇒K |

In Table 7, "HepIH No." represents clone numbers of replicon-replicating cell clones that have replicon RNA and have been cloned using HepG2 cells. "Nucleotide No." shows the corresponding nucleotide number in the nucleotide sequence (SEQ ID NO: 1) of replicon RNA rSGREP-JFH1. "Amino acid No." shows the corresponding amino acid number in the amino acid sequence (SEQ ID NO: 4) encoded by the JFH-1 clone. The types of nucleotides and amino acids at mutation sites are described according to their general notations. As shown in Table 7, for example, in clone HepIH1, a nucleotide corresponding to nucleotide No. 6826 of SEQ ID NO: on the replicon RNA mutated from C to A, so that an amino acid corresponding to amino acid No. 2714 of SEQ ID NO: mutated from Q to E. Similarly, in Table 8, "HeLaIH No." represents numbers of replicon-replicating cell clones that have replicon RNA and have been cloned using HeLa cells.

In addition, when Northern blot analysis was conducted for clones having no nucleotide mutations at all that cause amino acid mutations, it was shown that the quantity of replicon RNA replicated by the clones was lower than that of a cell clone replicating replicon RNA having a nucleotide mutation that causes an amino acid mutation. Hence, it was concluded that the nucleotide mutation in replicon RNA inducing an amino acid mutation was an adaptive mutation for increasing the replication efficiency of replicon RNA in cells.

INDUSTRIAL APPLICABILITY

The replicon-replicating cells according to the present invention can be utilized as a culture system for the continuous production of HCV genotype 2a-derived RNA and HCV protein. Moreover, the replicon-replicating cells according to the present invention are useful as a test system for screening for various substances affecting the replication of HCV and/or the translation into HCV protein.

All publications, patents and patent applications cited herein are incorporated herein by reference in their entirety.

SEQUENCE LISTING FREE TEXT

SEQ ID NO: 1. Explanation of artificial sequence: replicon
SEQ ID NO: 2. Explanation of artificial sequence: replicon
SEQ ID NO: 7. Explanation of artificial sequence: replicon
SEQ ID NOS: 8 to 12. Explanation of artificial sequences: synthetic RNA
SEQ ID NOS: 13 to 41. Explanation of artificial sequences: synthetic DNA

The invention claimed is:

1. A cell containing a replicon RNA comprising a nucleotide sequence containing at least the 5' untranslated region, the nucleotide sequence encoding NS3 protein, NS4A protein, NS4B protein, NS5A protein and NS5B protein and the 3' untranslated region of the genomic RNA of hepatitis C virus of genotype 2a strain JFH-1, and further containing a nucleotide sequence encoding a viral protein from the genomic RNA of an HCV strain or HCV genotype other than JFH-1, wherein said replicon is continuously replicated in the cell.

2. The cell of claim 1, said replicon further containing at least one internal ribosome entry site (IRES) and either one or both of a selection marker gene and/or a reporter gene.

3. The cell of claim 1, wherein said HCV strain or HCV genotype other than JFH-1 is HCV-1, HCV-H, HC-J1, HCT-18, DK-7, US11, S14, HCT23, HCV-Th, DR1, DR4, HCT27, S18, SW1, DK9, 1190, TD-6E1, S9, HCV-BK, T10, DK1, HC-J4, HCV-J, HK3, HK8, HK5, HCV-G3, IND5, IND8, P10, D1, D3, SW2, T3, S45, SA10, US6, HCV-JK1, HCV-JK4, HCV-JK3, HCV-JK2, HCV-JT, HC-J2, HCV-T, HK4, HC-G9, Z1, T4, T9, US10, HC-J5, T2, HC-J7, DK11, SW3, DK8, T8, HC-J8, S83, HK2, HC-J6, HC-J8, BEBE1, HCV-J6, HCV-J8, HD10-2, BR36-9; S52, S54, S2, BR33-1, HK10, DK12, HCV-TR, BA-1, BA-2, DK13, Z1, Z4, Z6, Z7, HK2, SA1, SA4, SA5, SA7, SA13, SA6, NZL1, SA30, EG-13, HCV-K3a/650, ED43, EUH1480, EUHK2, Th580, VN235, VN405, VN004, JK049, JK046, JCH-1, JCH-2, JCH-3, JCH-4, JCH-5, JCH-6, J6CF, or H77.

4. The cell of claim 1, wherein said cell is a human liver-derived cell, a human uterine cervix-derived cell or a human fetal kidney-derived cell.

5. The cell of claim 1, wherein said cell is selected from the group consisting of Huh7, HepG2, IMY-N9, HeLa, and a 293 cell.

6. The cell of claim 2, wherein the IRES is an EMCV IRES, FMDV IRES, or HCV IRES.

7. A replicon RNA comprising a nucleotide sequence containing at least the 5' untranslated region, the nucleotide sequence encoding NS3 protein, NS4A protein, NS4B protein, NS5A protein and NS5B protein, and the 3' untranslated region of the genomic RNA hepatitis C virus of genotype 2a strain JFH-1, wherein said replicon further contains a nucleotide sequence encoding a viral protein from the genomic RNA of an HCV strain or HCV genotype other than JFH-1, at least one internal ribosome entry site (IRES) and either one or both of a selection marker gene and/or a reporter gene.

8. The replicon RNA of claim 7, wherein said viral protein is a viral protein other than NS3, NS4A, NS4B, NS5A, and NS5B.

9. The replicon RNA of claim 7, wherein the IRES is an EMCV IRES, FMDV IRES, or HCV IRES.

10. The replicon RNA of claim 7, wherein said selection marker gene or reporter gene is ligated upstream of the IRES sequence, or upstream or downstream of the sequence encoding NS3 protein, NS4A protein, NS4B protein, NS5A protein or NS5B protein, or inserted in the sequence encoding NS3 protein, NS4A protein, NS4B protein, NS5A protein or NS5B protein.

11. A replicon-replicating cell, which is prepared by introducing the replicon RNA of claim 7 into a cell.

* * * * *